(12) United States Patent
Kapitan et al.

(10) Patent No.: US 11,311,314 B2
(45) Date of Patent: Apr. 26, 2022

(54) SPINAL SURGERY SYSTEMS AND METHODS

(71) Applicant: GetSet Surgical SA, Epalinges (CH)

(72) Inventors: John Kapitan, Leicester, NC (US); Ole Stoklund, Lausanne (CH); Lawrence Binder, Miami, FL (US)

(73) Assignee: GETSET SURGICAL SA, Epalinges (CH)

( * ) Notice: Subject to any disclaimer, the term of this patent is extended or adjusted under 35 U.S.C. 154(b) by 155 days.

(21) Appl. No.: 16/435,128

(22) Filed: Jun. 7, 2019

(65) Prior Publication Data

US 2020/0038201 A1 Feb. 6, 2020

Related U.S. Application Data

(60) Provisional application No. 62/712,938, filed on Jul. 31, 2018.

(51) Int. Cl.
*A61F 2/44* (2006.01)
*A61B 17/70* (2006.01)
*A61B 17/86* (2006.01)
*A61B 17/88* (2006.01)
(Continued)

(52) U.S. Cl.
CPC ...... *A61B 17/7032* (2013.01); *A61B 17/8615* (2013.01); *A61B 17/8685* (2013.01); *A61B 17/888* (2013.01); *A61F 2/442* (2013.01); *A61F 2/447* (2013.01); *A61F 2/4611* (2013.01); *A61B 17/7037* (2013.01); *A61B 2017/564* (2013.01); *A61F 2/4603* (2013.01); *A61F 2002/30112* (2013.01); *A61F 2002/30261* (2013.01);
(Continued)

(58) Field of Classification Search
CPC ............ A61F 2/44; A61F 2/442; A61F 2/447; A61F 2/46; A61F 2/4611
See application file for complete search history.

(56) References Cited

U.S. PATENT DOCUMENTS

| | | |
|---|---|---|
| 2,905,178 A | 9/1959 | Hilzinger |
| 3,681,840 A | 8/1972 | Pool |
| 3,703,843 A | 11/1972 | Laverty |
| RE28,111 E | 8/1974 | Laverty |
| 3,861,269 A | 1/1975 | Laverty |
| 4,268,253 A | 5/1981 | Gross et al. |

(Continued)

FOREIGN PATENT DOCUMENTS

| | | |
|---|---|---|
| CN | 204033456 U | 12/2014 |
| GB | 2348390 B | 10/2000 |
| WO | WO2007038654 | 4/2007 |

(Continued)

OTHER PUBLICATIONS

International Search Report dated Oct. 15, 2019 for corresponding International Application No. PCT/2019/044429.
(Continued)

*Primary Examiner* — Christopher J Beccia
(74) *Attorney, Agent, or Firm* — David Meibos; Maywood IP Law

(57) ABSTRACT

An intervertebral spacer may include a superior surface configured to engage a superior vertebral body, an inferior surface configured to engage an inferior vertebral body, and a peripheral wall extending from the superior surface to the inferior surface. A proximal end of the peripheral wall may include with a cam surface that is rotatable against a complementary cam surface of an inserter tool such that a first force causes the intervertebral spacer to pivot, relative to the inserter tool, about a pivot point associated with the cam surface.

24 Claims, 81 Drawing Sheets

(51) Int. Cl.
  *A61F 2/46* (2006.01)
  *A61B 17/56* (2006.01)
  *A61F 2/30* (2006.01)

(52) U.S. Cl.
  CPC .............. *A61F 2002/30593* (2013.01); *A61F 2002/4615* (2013.01); *A61F 2002/4627* (2013.01); *A61F 2002/4628* (2013.01)

(56) References Cited

U.S. PATENT DOCUMENTS

| | | |
|---|---|---|
| 5,246,442 A | 9/1993 | Ashman et al. |
| 5,259,398 A | 11/1993 | Vrespa |
| 5,269,686 A | 12/1993 | James |
| 5,368,594 A | 11/1994 | Martin et al. |
| 5,405,328 A | 4/1995 | Vidal et al. |
| 5,593,410 A | 1/1997 | Vrespa |
| 5,601,553 A | 2/1997 | Trebing et al. |
| 5,672,176 A | 9/1997 | Biedermann et al. |
| 5,697,929 A | 12/1997 | Mellinger |
| 5,728,098 A | 3/1998 | Sherman et al. |
| 5,797,911 A | 8/1998 | Sherman et al. |
| 5,879,350 A | 3/1999 | Sherman et al. |
| 5,885,286 A | 3/1999 | Sherman et al. |
| 5,989,250 A | 11/1999 | Wagner et al. |
| 6,010,503 A | 1/2000 | Richelsoph et al. |
| 6,045,312 A | 4/2000 | Hsing |
| 6,053,917 A | 4/2000 | Sherman et al. |
| 6,179,841 B1 | 1/2001 | Jackson |
| 6,187,005 B1 | 2/2001 | Brace et al. |
| 6,193,719 B1 | 2/2001 | Gournay et al. |
| 6,216,570 B1 | 4/2001 | Freed |
| 6,254,602 B1 | 7/2001 | Justis |
| 6,257,105 B1 | 7/2001 | Lin |
| 6,261,296 B1 | 7/2001 | Aebi et al. |
| 6,273,888 B1 | 8/2001 | Justis |
| 6,296,642 B1 | 10/2001 | Morrison et al. |
| 6,478,795 B1 | 11/2002 | Gournay et al. |
| 6,562,040 B1 | 5/2003 | Wagner |
| 6,660,006 B2 | 12/2003 | Markworth et al. |
| 6,712,825 B2 | 3/2004 | Aebi et al. |
| 6,743,233 B1 | 6/2004 | Baldwin et al. |
| 6,834,571 B1 | 12/2004 | Lowe et al. |
| 7,445,627 B2 | 11/2008 | Hawkes et al. |
| 7,476,226 B2 | 1/2009 | Weikel et al. |
| 7,476,239 B2 | 1/2009 | Jackson |
| 7,572,281 B2 | 8/2009 | Runco et al. |
| 7,677,891 B2 | 3/2010 | Niznick |
| 7,794,477 B2 | 9/2010 | Melkent et al. |
| 7,828,829 B2 | 11/2010 | Ensign |
| 8,029,285 B2 | 10/2011 | Holmen et al. |
| 8,043,293 B2 * | 10/2011 | Warnick ................ A61F 2/4611 606/86 A |
| 8,088,163 B1 | 1/2012 | Kleiner |
| 8,226,656 B2 | 7/2012 | McBride |
| 8,235,997 B2 | 8/2012 | Hoffman et al. |
| 8,241,294 B2 | 8/2012 | Sommerich et al. |
| 8,608,651 B2 | 12/2013 | Shluzas |
| 8,668,699 B2 | 3/2014 | Thomas et al. |
| 8,685,029 B2 | 4/2014 | Dziedzic et al. |
| 8,828,060 B2 | 9/2014 | Biedermann et al. |
| 8,858,637 B2 * | 10/2014 | Milz ................ A61F 2/4455 623/17.16 |
| 8,900,240 B2 | 12/2014 | White et al. |
| 8,920,424 B2 | 12/2014 | Boykin |
| D723,691 S | 3/2015 | McCormack et al. |
| 8,968,367 B2 | 3/2015 | Kretzer et al. |
| 8,986,307 B2 | 3/2015 | Kirschman |
| 9,050,062 B1 | 6/2015 | Gauthier et al. |
| 9,078,679 B2 | 7/2015 | Schuele et al. |
| 9,084,642 B2 | 7/2015 | Peultier |
| 9,168,058 B2 | 10/2015 | Duperier et al. |
| 9,198,695 B2 | 12/2015 | Shluzas et al. |
| 9,295,500 B2 | 3/2016 | Marigowda |
| 9,339,319 B2 | 5/2016 | Schmuck et al. |
| 9,345,587 B2 | 5/2016 | Mitchell |
| 9,393,039 B2 | 7/2016 | Lechner et al. |
| 9,446,507 B2 | 9/2016 | Nino et al. |
| 9,463,063 B2 | 10/2016 | Seddon et al. |
| 9,532,814 B2 | 1/2017 | Harper |
| 9,572,617 B1 | 2/2017 | Prado et al. |
| 9,622,879 B2 * | 4/2017 | Taylor ................ A61F 2/4611 |
| RE46,409 E | 5/2017 | Foley et al. |
| 9,649,140 B1 | 5/2017 | Doose et al. |
| 9,693,814 B2 | 7/2017 | Schaller et al. |
| 9,795,494 B2 * | 10/2017 | Flickinger ............ A61F 2/4465 |
| D841,165 S | 2/2019 | McCormack et al. |
| 10,206,787 B2 | 2/2019 | Voellmicke |
| 2002/0091386 A1 | 7/2002 | Martin et al. |
| 2002/0138076 A1 | 9/2002 | Biedermann et al. |
| 2003/0060714 A1 | 3/2003 | Henderson et al. |
| 2003/0125741 A1 | 7/2003 | Biedermann et al. |
| 2004/0082956 A1 | 4/2004 | Baldwin et al. |
| 2004/0181224 A1 | 9/2004 | Biedermann et al. |
| 2006/0149241 A1 | 7/2006 | Richelsoph et al. |
| 2006/0241599 A1 | 10/2006 | Konieczynski et al. |
| 2007/0213737 A1 | 9/2007 | Schermerhorn et al. |
| 2008/0015584 A1 | 1/2008 | Richelsoph |
| 2008/0027544 A1 * | 1/2008 | Melkent ................ A61F 2/4611 623/17.11 |
| 2008/0065219 A1 | 3/2008 | Dye |
| 2009/0018591 A1 | 1/2009 | Hawkes et al. |
| 2009/0054991 A1 | 2/2009 | Biyani et al. |
| 2009/0234395 A1 | 9/2009 | Hoffman et al. |
| 2009/0259234 A1 | 10/2009 | Waller |
| 2010/0137879 A1 | 6/2010 | Ko et al. |
| 2010/0241175 A1 | 9/2010 | Walker et al. |
| 2010/0286783 A1 | 11/2010 | Lechmann et al. |
| 2011/0046637 A1 | 2/2011 | Patel et al. |
| 2011/0077694 A1 | 3/2011 | Biedermann et al. |
| 2011/0208238 A1 | 8/2011 | Hoffman |
| 2011/0213424 A1 | 9/2011 | Biedermann et al. |
| 2011/0313471 A1 | 12/2011 | McLean et al. |
| 2012/0143224 A1 | 6/2012 | Chan |
| 2012/0143265 A1 | 6/2012 | Biedermann et al. |
| 2013/0096568 A1 | 4/2013 | Justis |
| 2013/0096618 A1 | 4/2013 | Chandanson et al. |
| 2013/0103102 A1 * | 4/2013 | Taylor ................ A61F 2/4465 606/86 A |
| 2013/0123923 A1 | 5/2013 | Pavlov et al. |
| 2013/0253517 A1 | 9/2013 | Mitchell et al. |
| 2013/0253518 A1 | 9/2013 | Mitchell et al. |
| 2013/0253519 A1 | 9/2013 | Mitchell et al. |
| 2013/0253594 A1 | 9/2013 | Zucherman et al. |
| 2013/0253595 A1 | 9/2013 | Zucherman et al. |
| 2013/0261626 A1 | 10/2013 | Chavarria et al. |
| 2014/0025119 A1 | 1/2014 | Biedermann et al. |
| 2014/0031880 A1 | 1/2014 | Biedermann et al. |
| 2014/0058465 A1 | 2/2014 | Nichols et al. |
| 2014/0100657 A1 | 4/2014 | McCormack et al. |
| 2014/0135930 A1 | 5/2014 | Georges |
| 2014/0172103 A1 | 6/2014 | O'Neil et al. |
| 2014/0277212 A1 | 9/2014 | Dauster |
| 2015/0148835 A1 | 5/2015 | Faller et al. |
| 2015/0265271 A1 | 9/2015 | Galligan et al. |
| 2015/0297357 A1 | 10/2015 | McCormack et al. |
| 2016/0030188 A1 | 2/2016 | Lynn et al. |
| 2016/0175060 A1 | 6/2016 | Park |
| 2016/0296344 A1 | 10/2016 | Greenhalgh et al. |

FOREIGN PATENT DOCUMENTS

| | | |
|---|---|---|
| WO | WO2009015100 | 1/2009 |
| WO | WO2009040840 | 4/2009 |
| WO | WO2016073912 | 5/2016 |

OTHER PUBLICATIONS

International Search Report dated Oct. 15, 2019 for corresponding International Application No. PCT/US2019/044456.

* cited by examiner

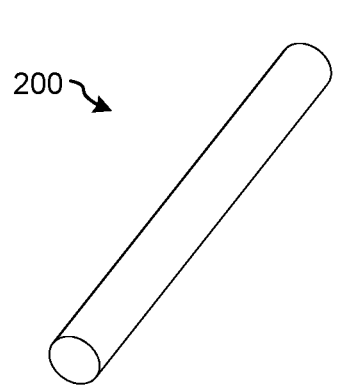
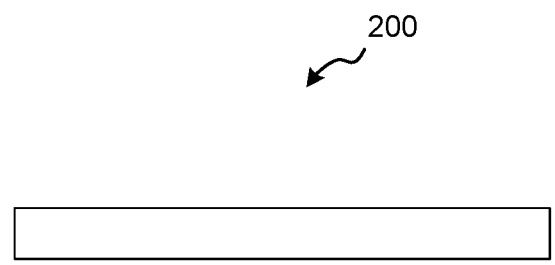
FIG. 2A      FIG. 2B
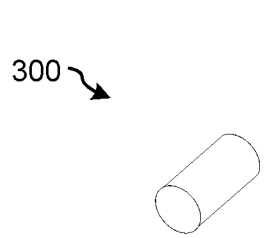
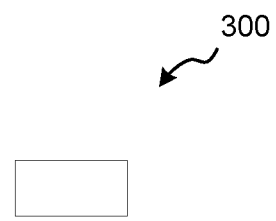
FIG. 3A      FIG. 3B

1400

1400

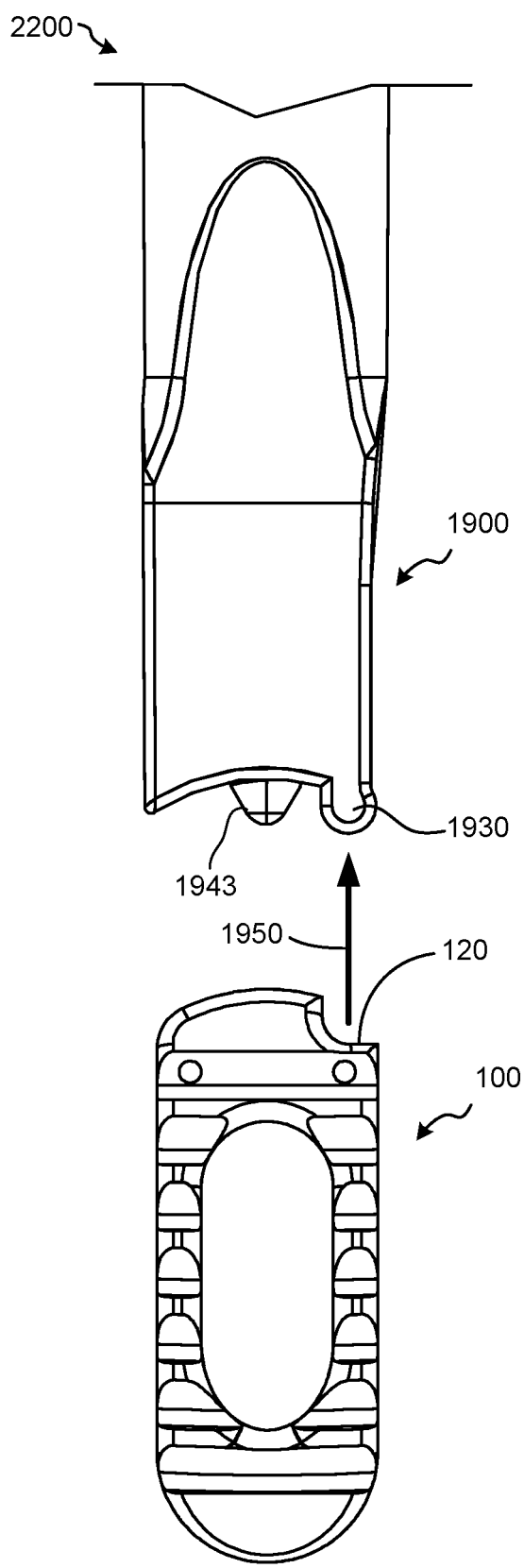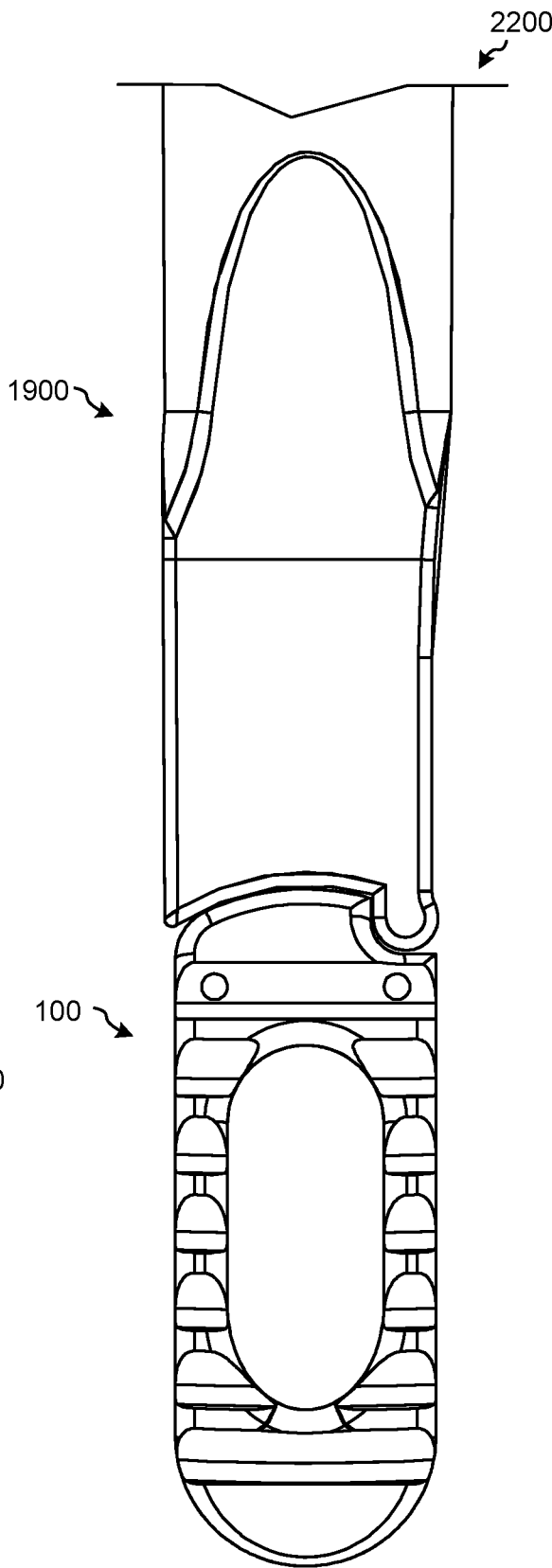
FIG. 22A  FIG. 22B

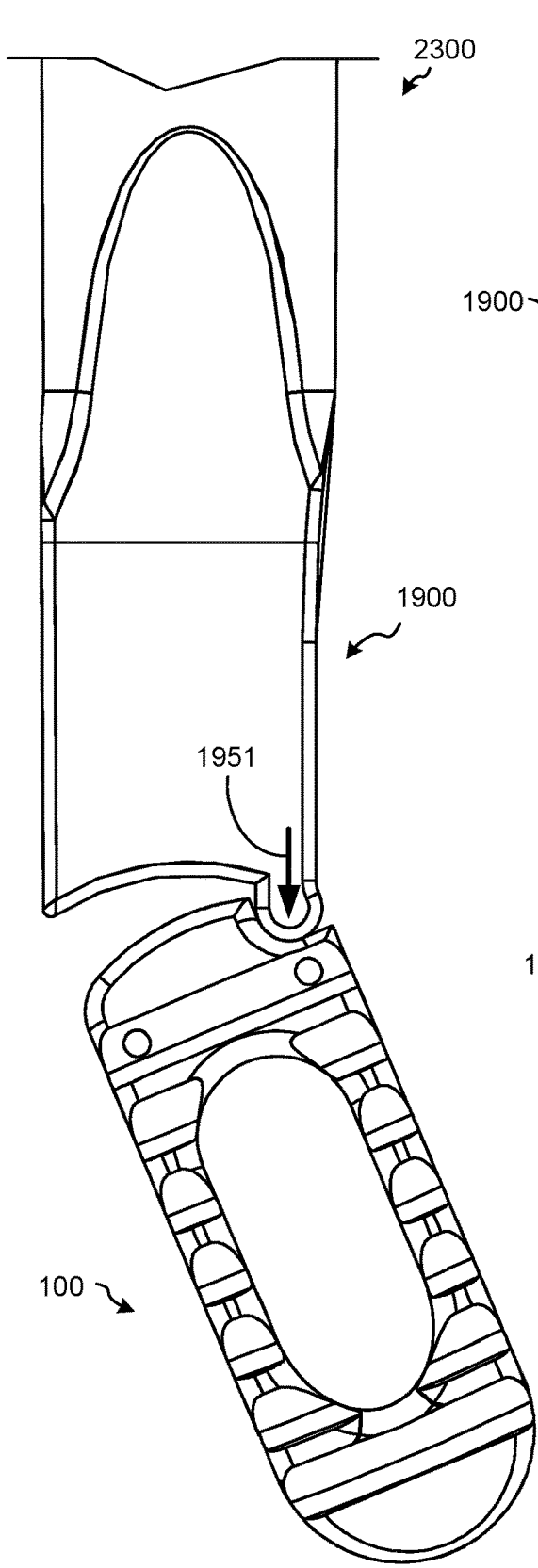 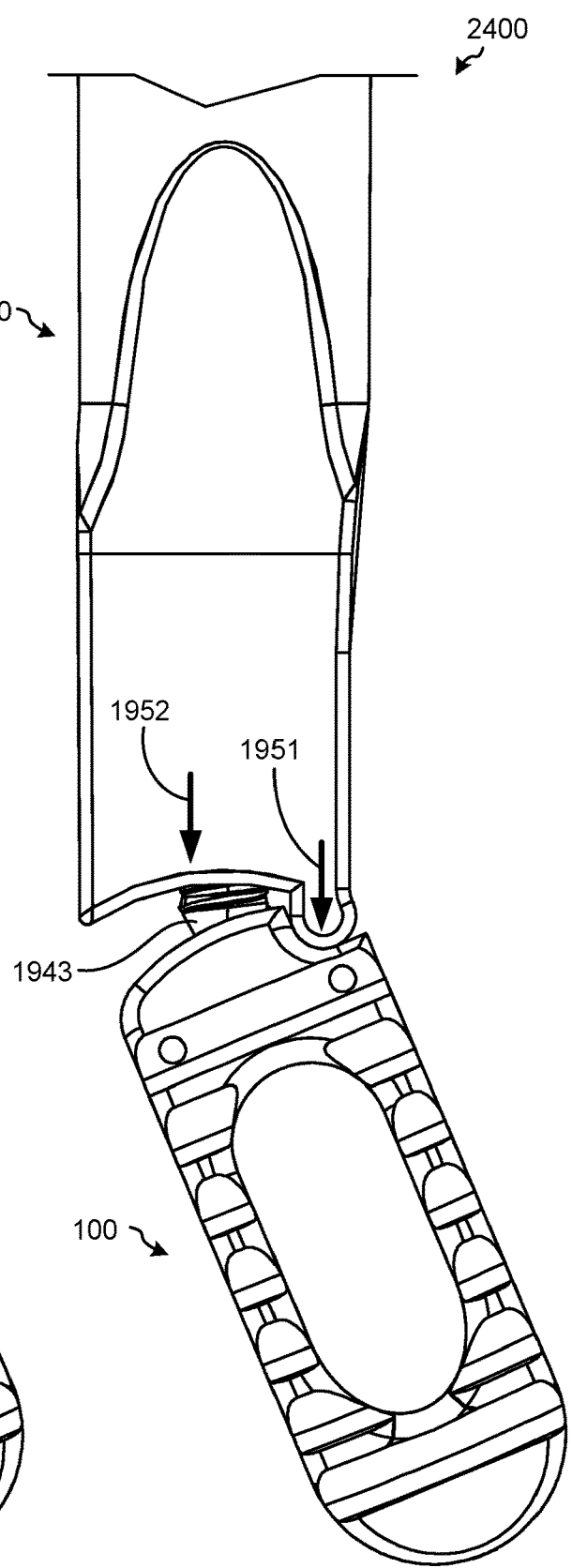
FIG. 23  FIG. 24

SPINAL SURGERY SYSTEMS AND METHODS

CROSS-REFERENCE TO RELATED APPLICATIONS

This application claims the benefit of U.S. Provisional Patent Application Ser. No. 62/712,938 filed on Jul. 31, 2018, entitled "SPINAL SURGERY SYSTEMS AND METHODS," the disclosure of which is incorporated herein by reference in its entirety.

TECHNICAL FIELD

The present disclosure relates to surgical systems, methods, instruments, and devices. More specifically, the present disclosure relates to improved surgical systems, methods, devices, and instruments for implanting intervertebral spacers between adjacent vertebral bodies in a patient.

BACKGROUND

Spinal fixation procedures utilizing intervertebral spacers can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an intervertebral spacer can be positioned within a space previously occupied by a disc between adjacent vertebral bodies. Such intervertebral spacers can help maintain a desired spacing between adjacent vertebrae and/or promote fusion between adjacent vertebrae. The use of bone graft and/or other materials within an intervertebral spacer can also facilitate the fusion of adjacent vertebral bodies. Accordingly, a need exists for improved intervertebral spacers and related surgical instrumentation, tools, systems and methods.

SUMMARY

The various systems and methods of the present disclosure have been developed in response to the present state of the art, and in particular, in response to the problems and needs in the art that have not yet been fully solved by currently available surgical devices, instruments, systems, and methods for implanting intervertebral spacers between vertebral bodies of a patient.

According to some embodiments, an intervertebral spacer may include a superior surface configured to engage a superior vertebral body, an inferior surface configured to engage an inferior vertebral body, and a peripheral wall extending from the superior surface to the inferior surface. The peripheral wall may have a distal end and a proximal end that includes a cam surface that is rotatable against a complementary cam surface of an inserter tool such that a first force causes the intervertebral spacer to pivot, relative to the inserter tool, about a pivot point associated with the cam surface.

In other embodiments, a spinal fusion system may include an intervertebral spacer and an inserter tool. The intervertebral spacer may include a superior surface configured to engage a superior vertebral body, an inferior surface configured to engage an inferior vertebral body, and a peripheral wall extending from the superior surface to the inferior surface. The peripheral wall may have a distal end and a proximal end comprising a cam surface that is rotatable against a complementary cam surface such that a first force causes the intervertebral spacer to pivot about a pivot point associated with the cam surface. The inserter tool may include a shroud having a proximal end and a distal end, a handle located toward the proximal end of the shroud, and a cam lobe located at the distal end of the shroud, with the shroud extending between the handle and the cam lobe. The cam lobe may be configured to impart the first force to the cam surface that causes the intervertebral spacer to pivot about the pivot point associated with the cam surface.

In yet other embodiments, a method for inserting an intervertebral spacer comprising a cam surface between two vertebral bodies of a patient through use of an inserter tool that comprises a complimentarily shaped cam lobe configured to engage the cam surface and permit selective rotation of the intervertebral spacer relative to the inserter tool may include aligning the cam surface of the intervertebral spacer with the complimentarily shaped cam lobe of the inserter tool. The method may also include moving the cam surface into engagement with the complimentarily shaped cam lobe and inserting the intervertebral spacer between the two vertebral bodies of the patient.

These and other features and advantages of the present disclosure will become more fully apparent from the following description and appended claims, or may be learned by the practice of the systems and methods set forth hereinafter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings in which:

FIG. 2A is a perspective view of a first radiopaque marker 200, according to an embodiment of the present disclosure;

FIG. 2B is a side view of the first radiopaque marker 200 of FIG. 2A;

FIG. 3A is a perspective view of a second radiopaque marker 300, according to an embodiment of the present disclosure;

FIG. 3B is a side view of the second radiopaque marker 300 of FIG. 3A;

FIG. 18B is a perspective top view of a distal end of the intervertebral spacer 1800 of FIG. 18A;

FIG. 18C is a top view of the intervertebral spacer 1800 of FIG. 18A;

FIG. 18D is a bottom view of the intervertebral spacer 1800 of FIG. 18A;

FIG. 18E illustrates a first side of the intervertebral spacer 1800 of FIG. 18A;

FIG. 18F illustrates a second side of the intervertebral spacer 1800 of FIG. 18A;

FIG. 18G illustrates the distal end of the intervertebral spacer 1800 of FIG. 18A;

FIG. 18H illustrates the proximal end of the intervertebral spacer 1800 of FIG. 18A;

FIG. 19A is a perspective top view of a proximal end of an inserter tool 1900, according to an embodiment of the present disclosure;

FIG. 19B is a perspective top view of a distal end of the inserter tool 1900 of FIG. 19A;

FIG. 19C is a top view of the inserter tool 1900 of FIG. 19A;

FIG. 19D is a bottom view of the inserter tool 1900 of FIG. 19A;

FIG. 19E is a right side view of the inserter tool 1900 of FIG. 19A;

Figure 19A:
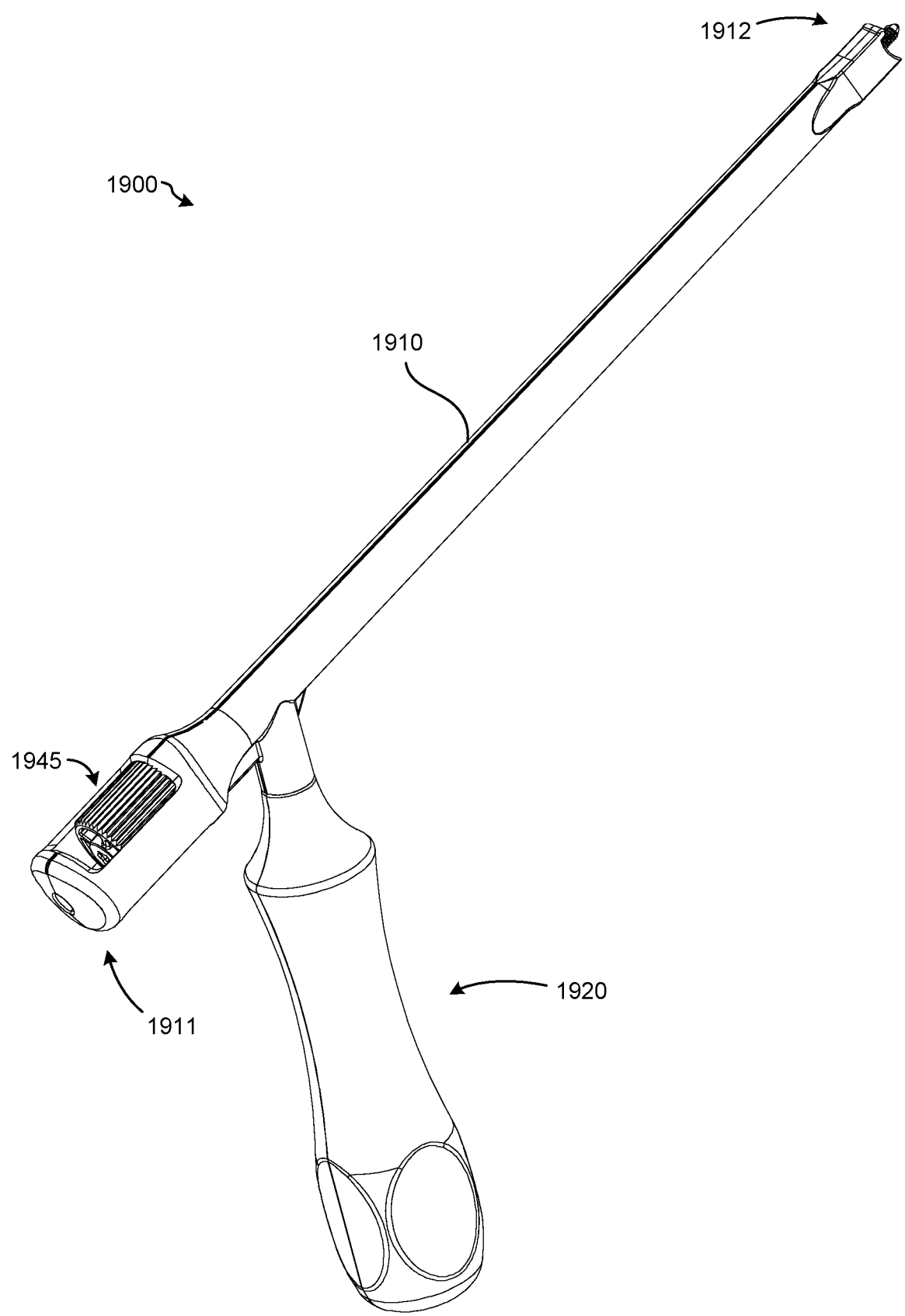
Figure 19B:
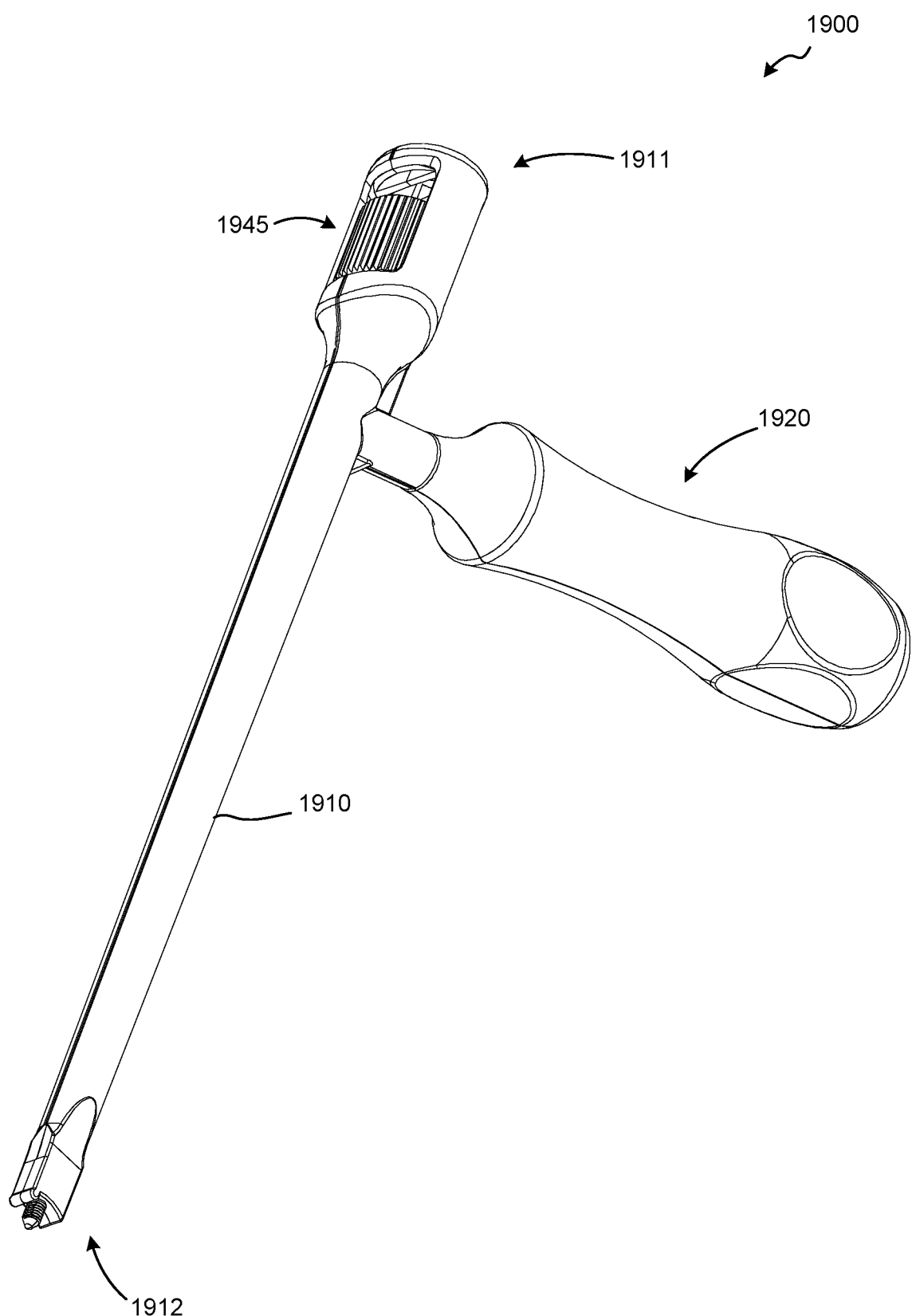
Figures 19C, 19D:
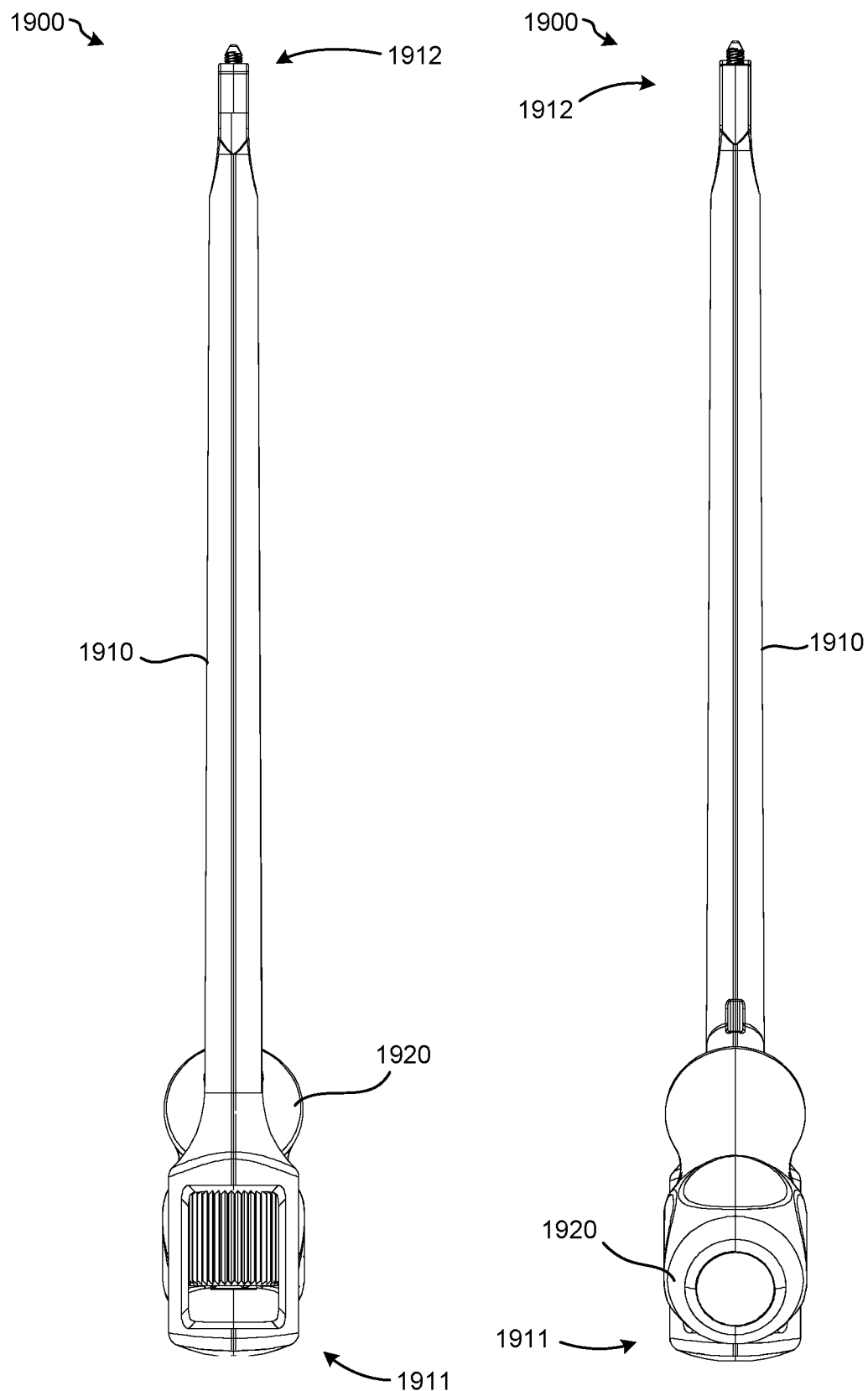
Figure 19E:
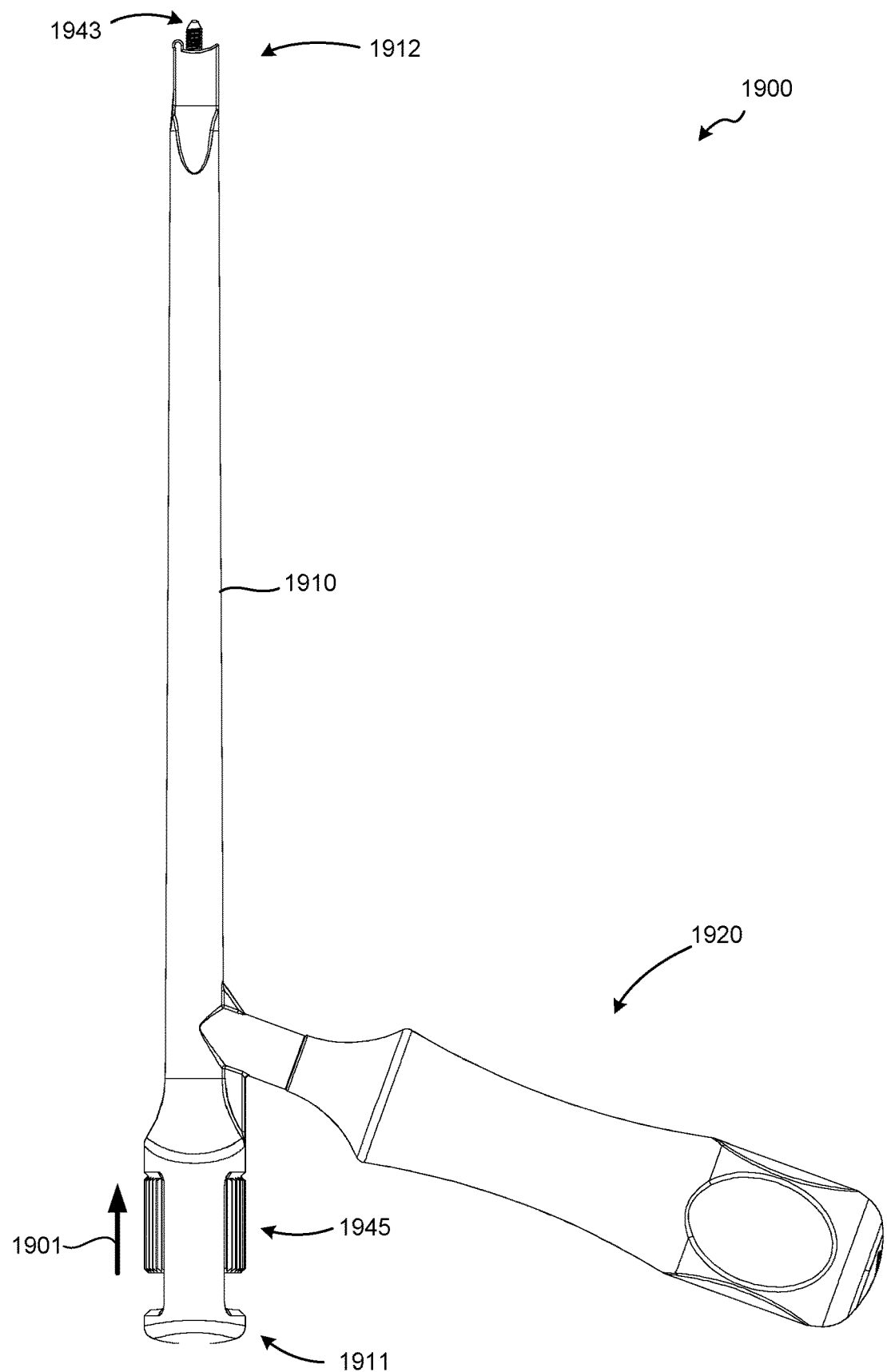
Figure 19F:
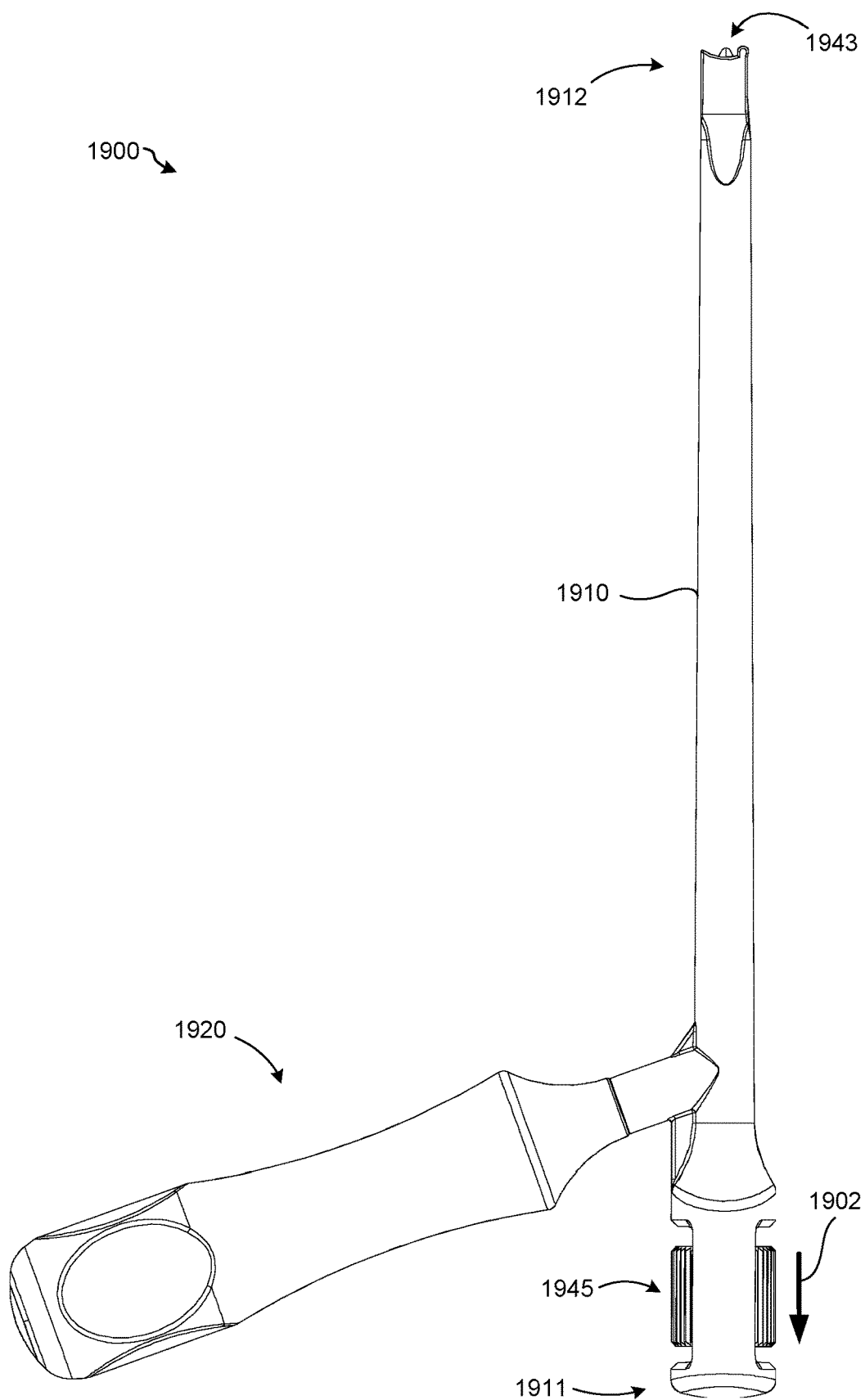
Figure 19G:
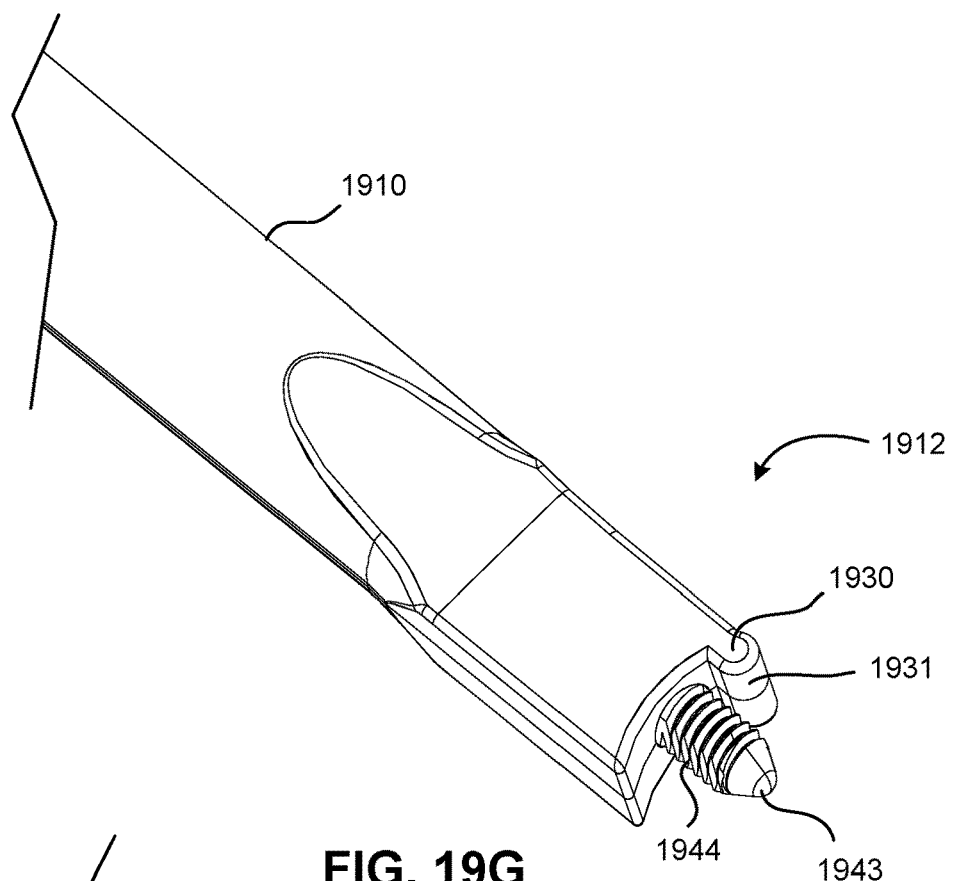
Figure 19H:
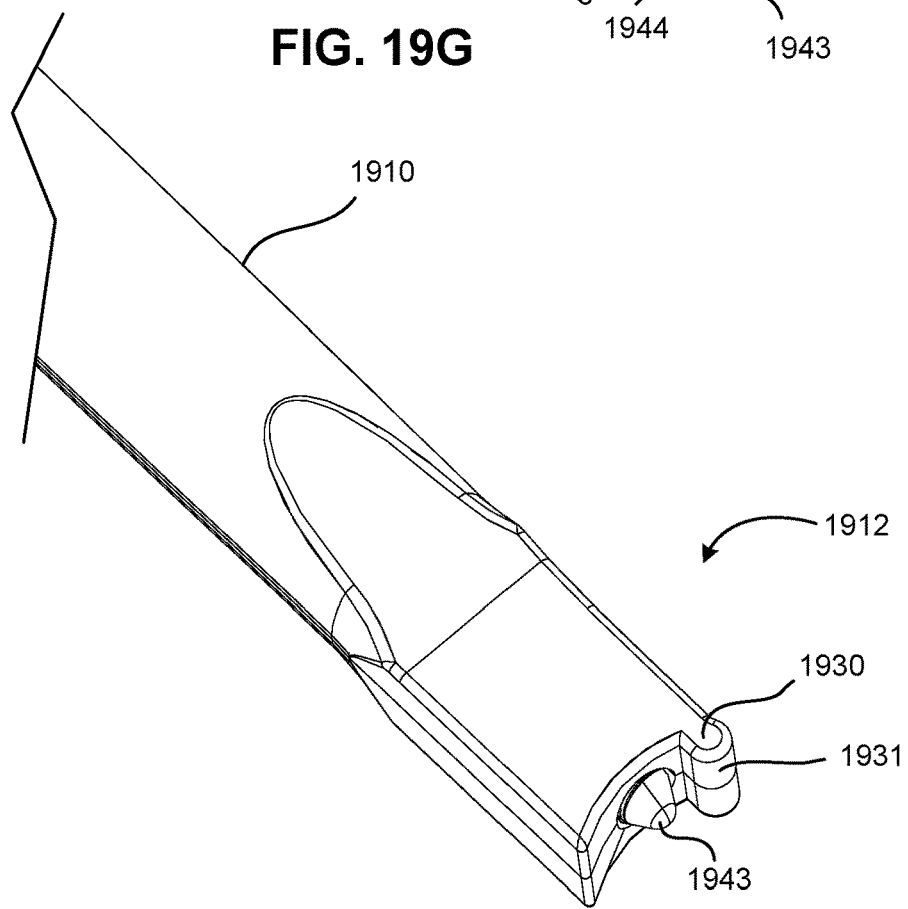
Figure 20A:
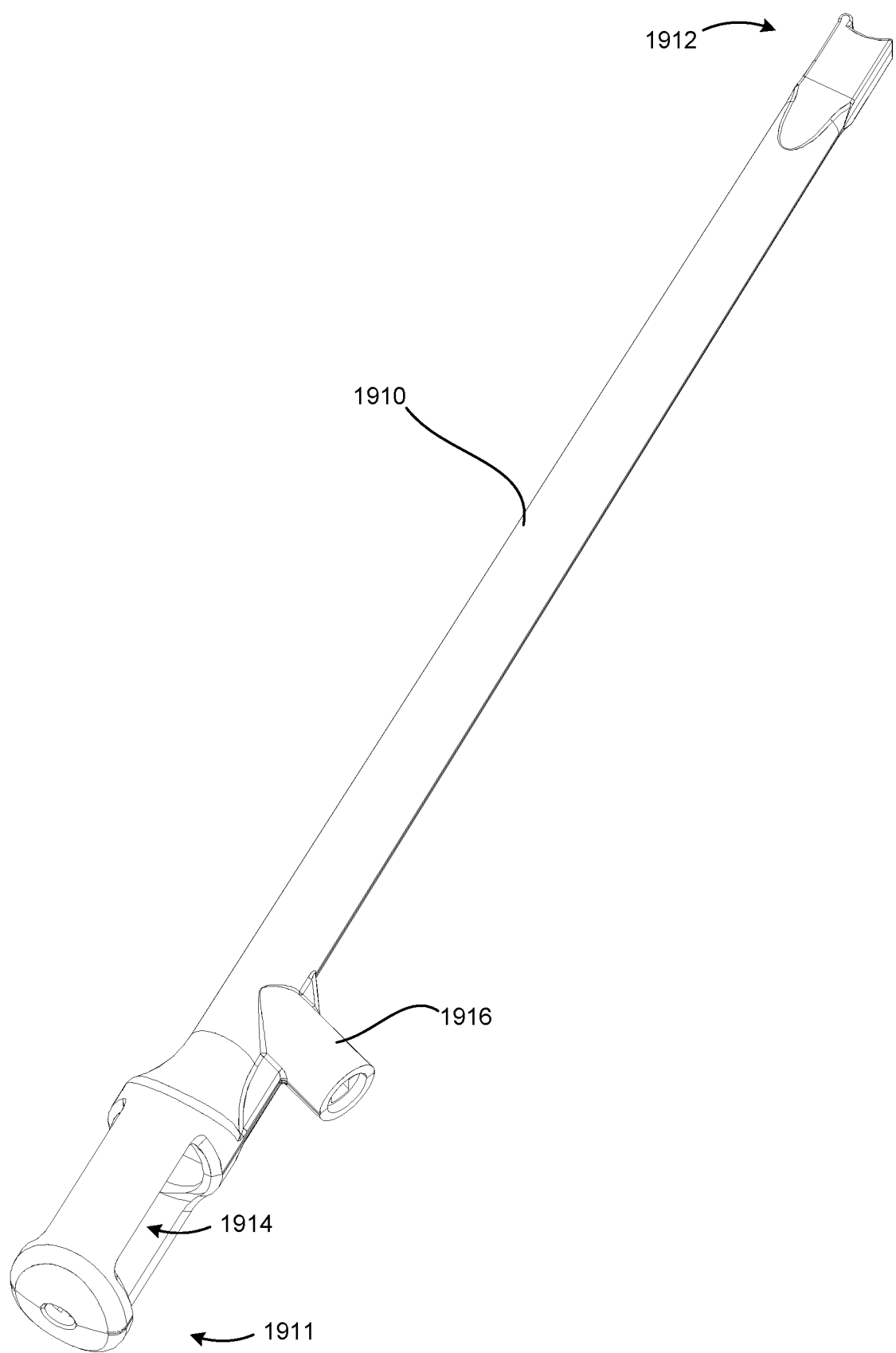
Figure 20B:
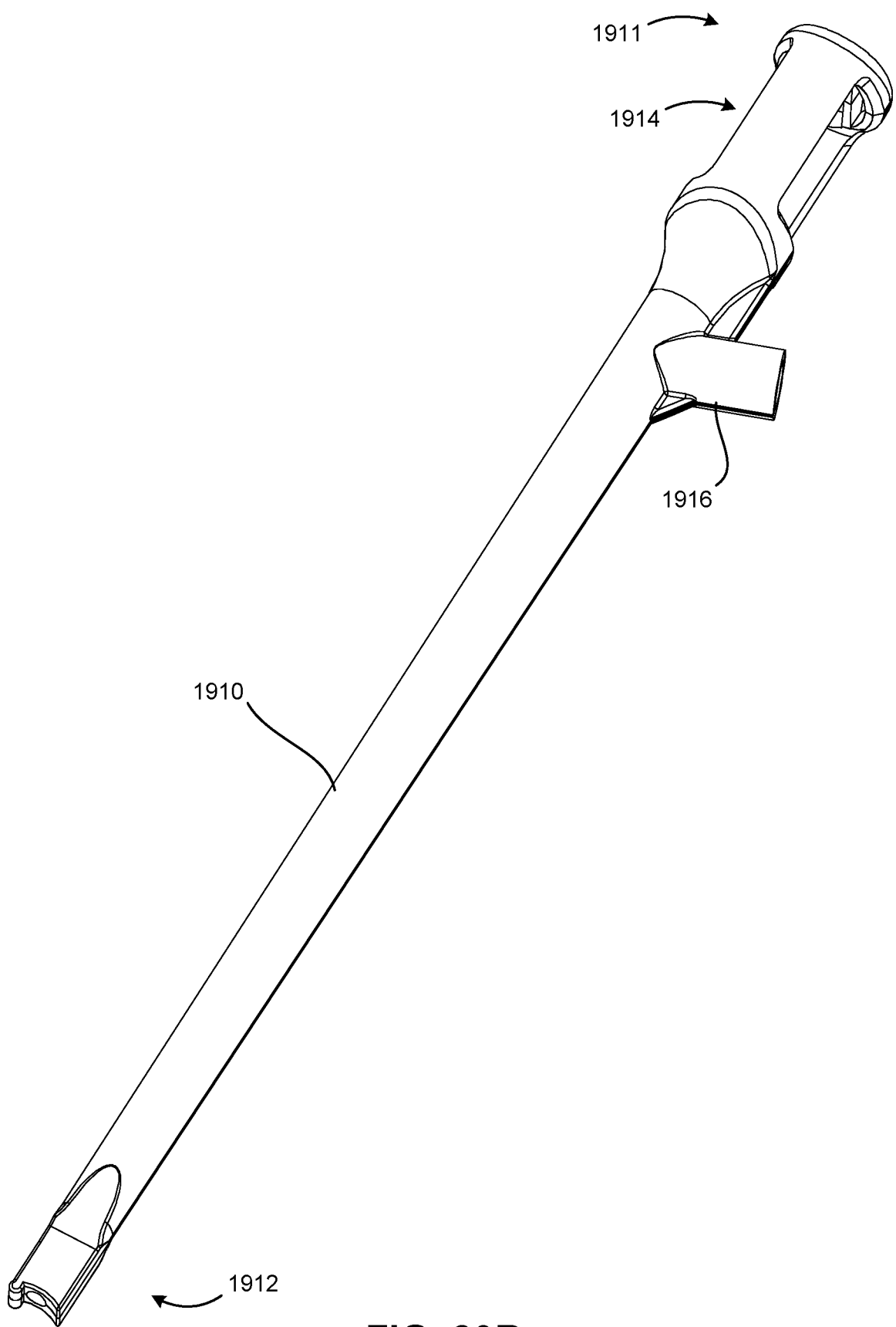
Figure 20C:
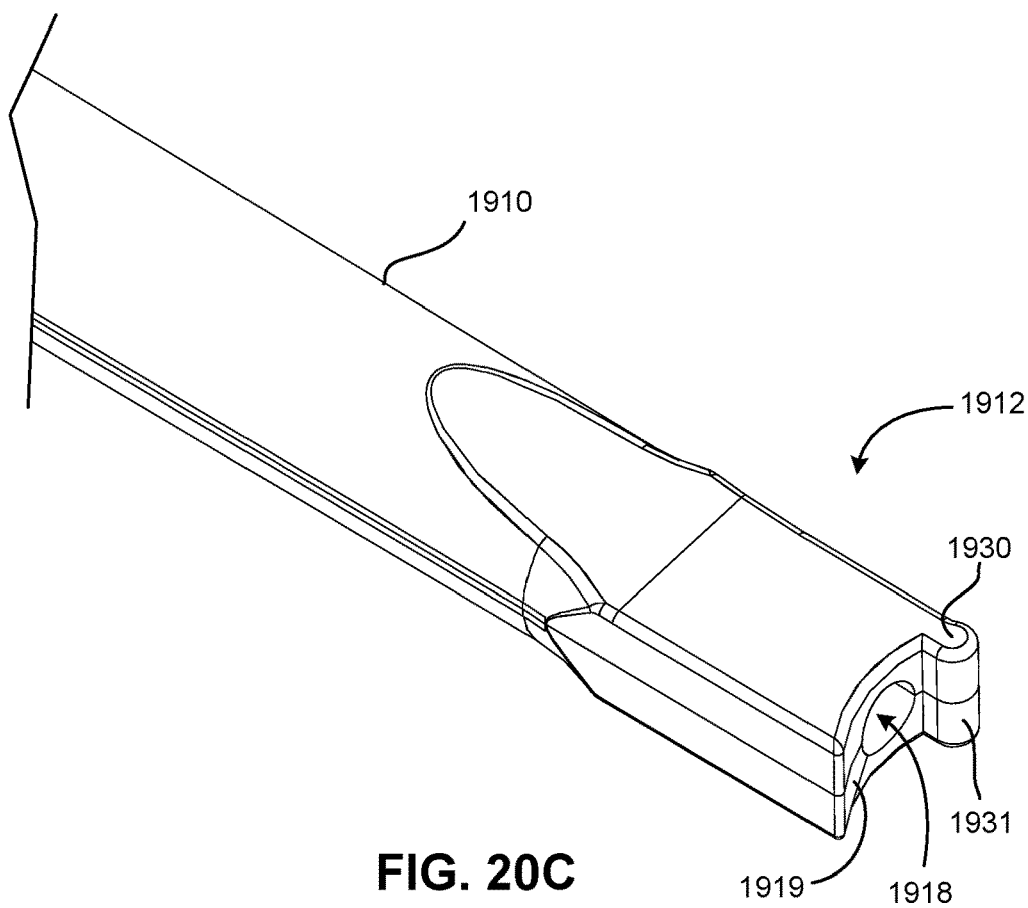
Figure 20D:
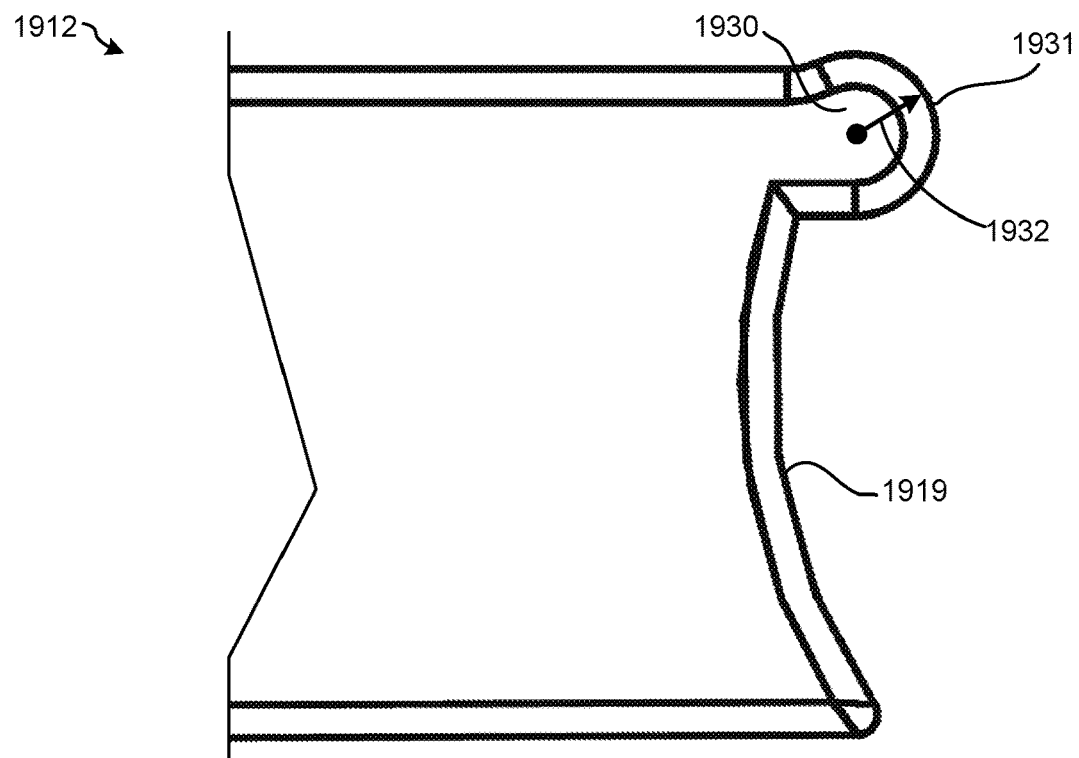
Figure 21A:
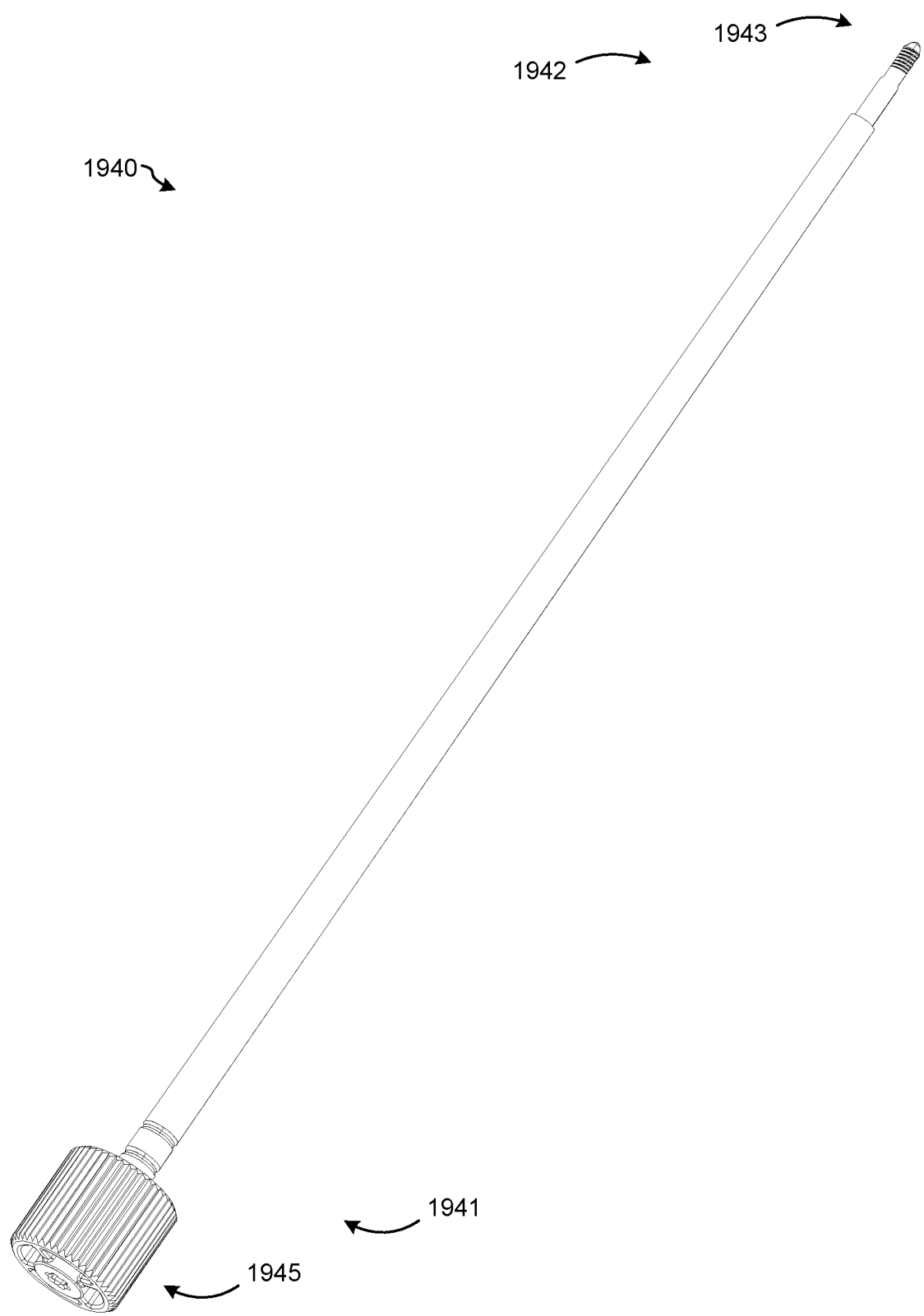
Figure 21B:
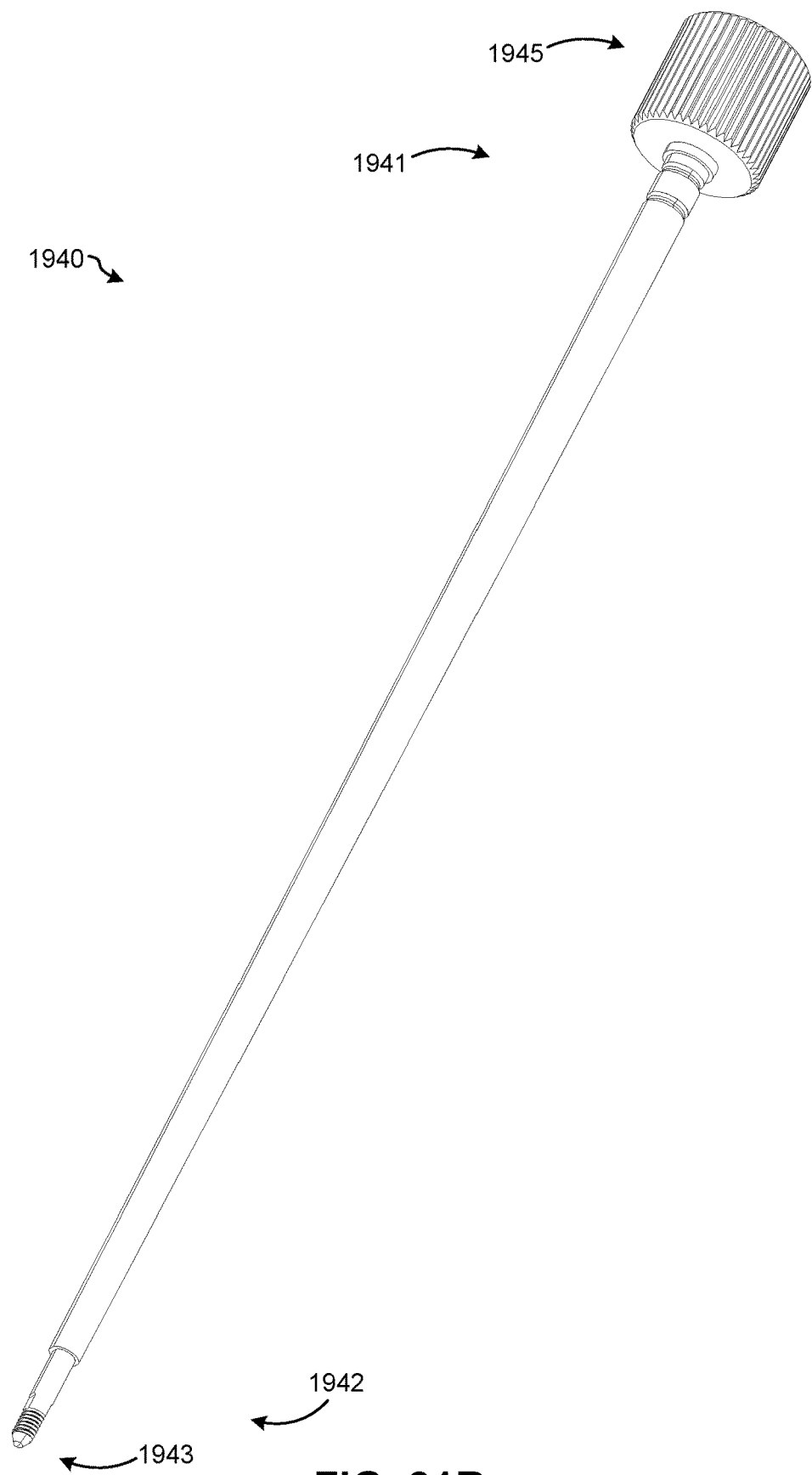
Figure 21C:
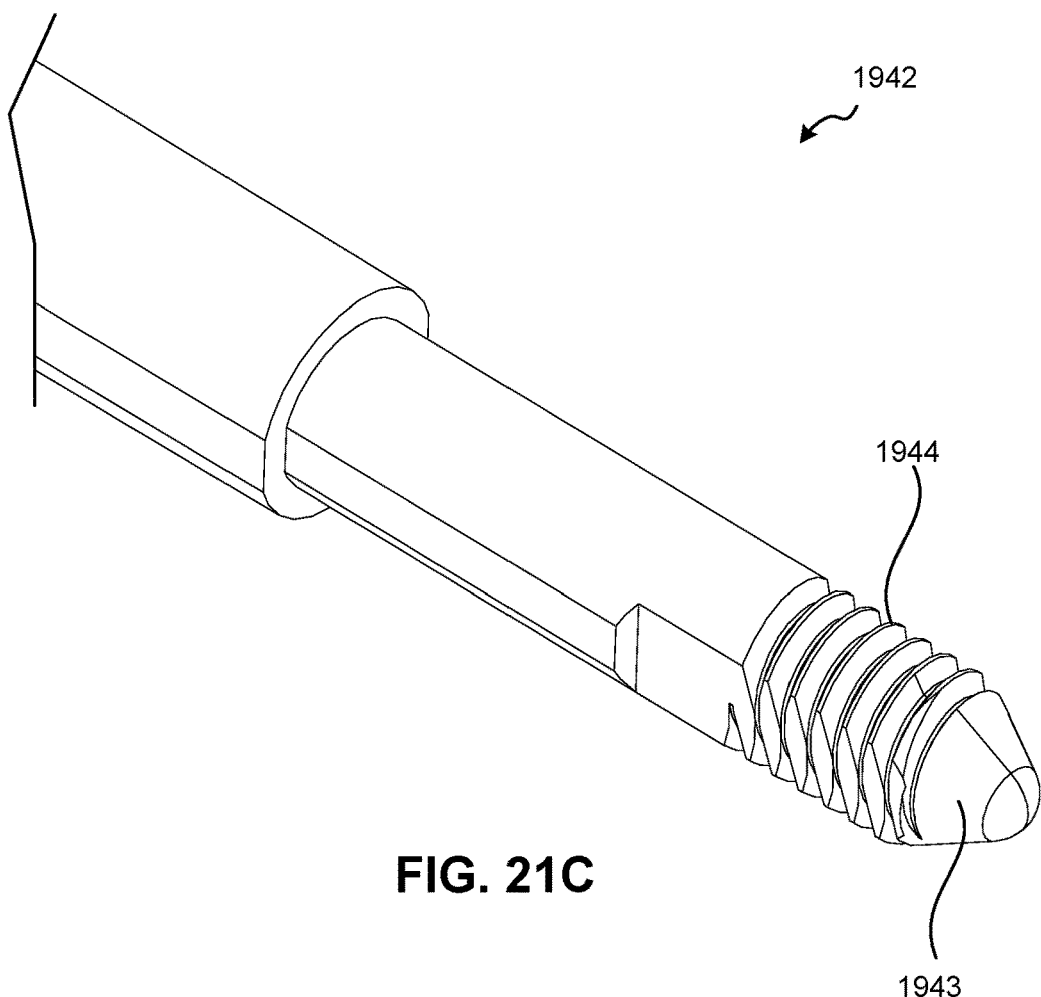
Figure 21D:
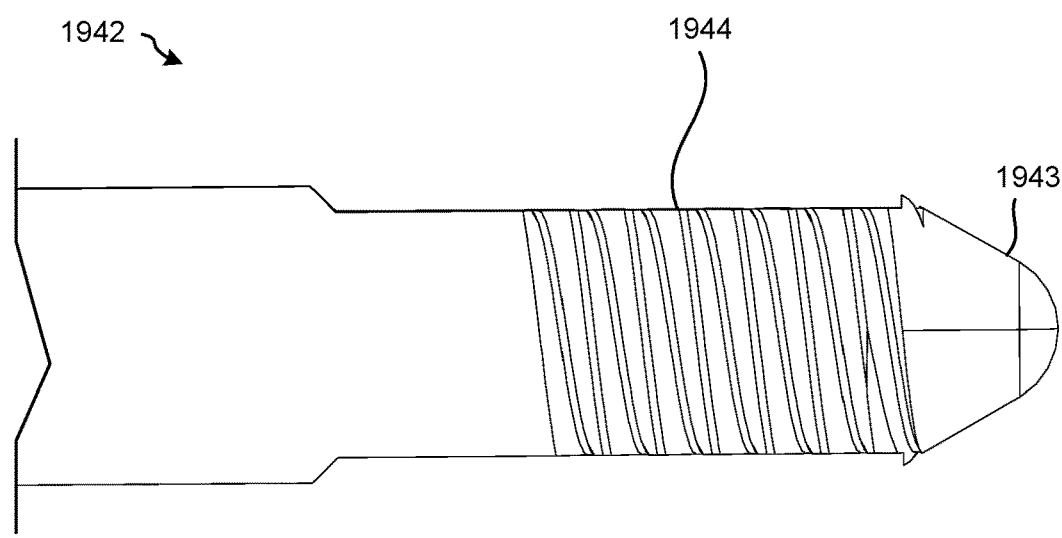
Figure 25:
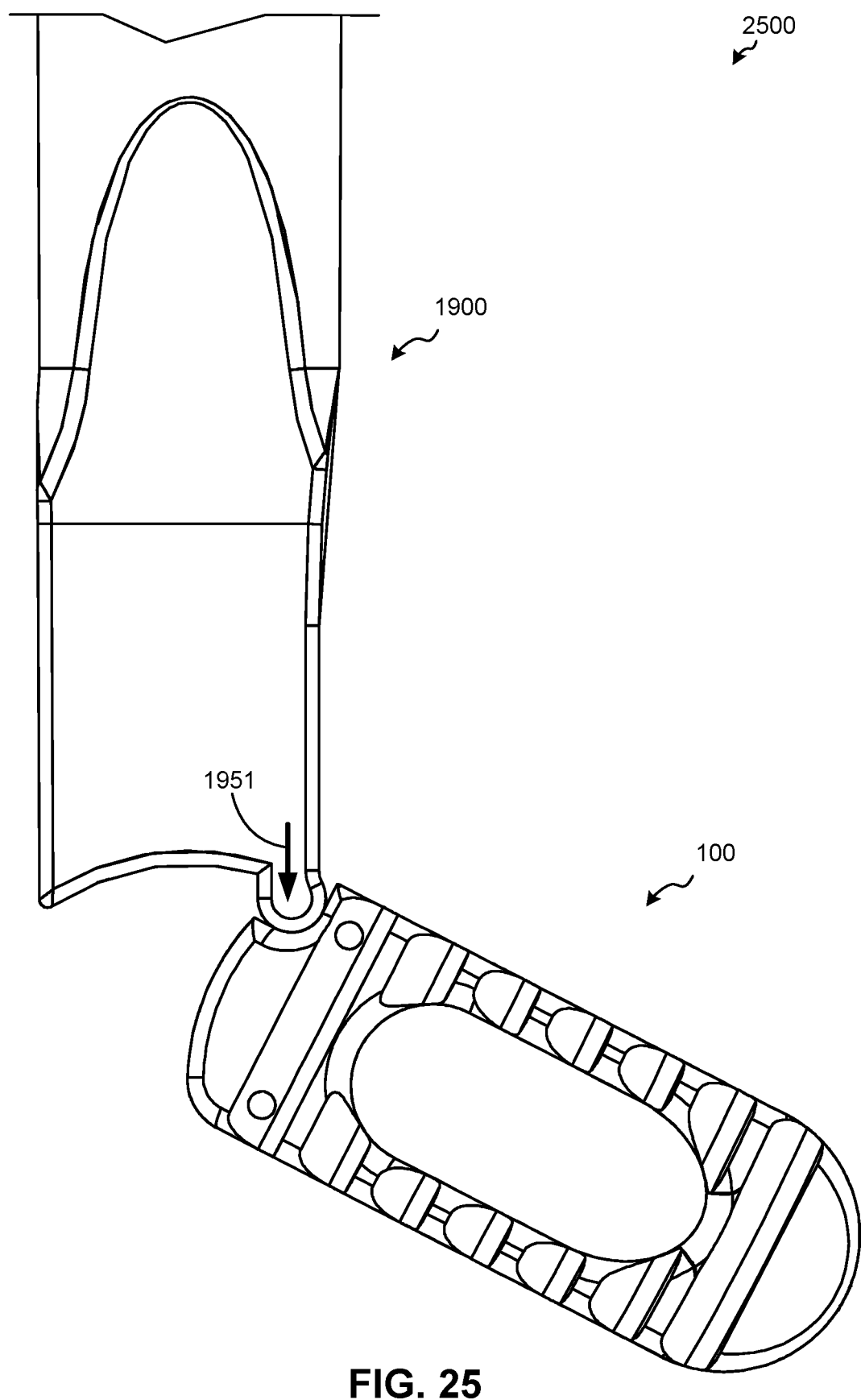
Figure 26:
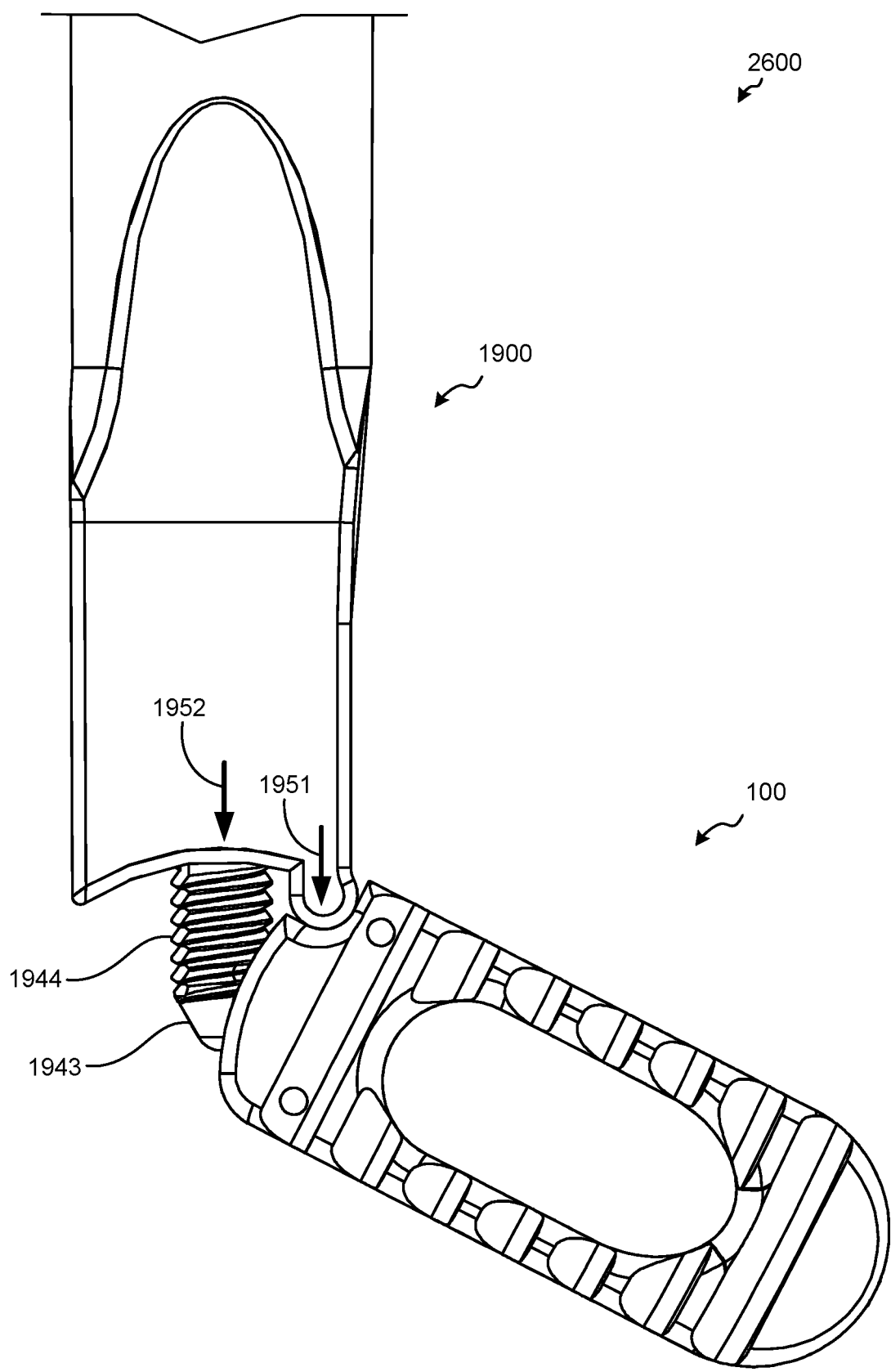
Figure 27A:
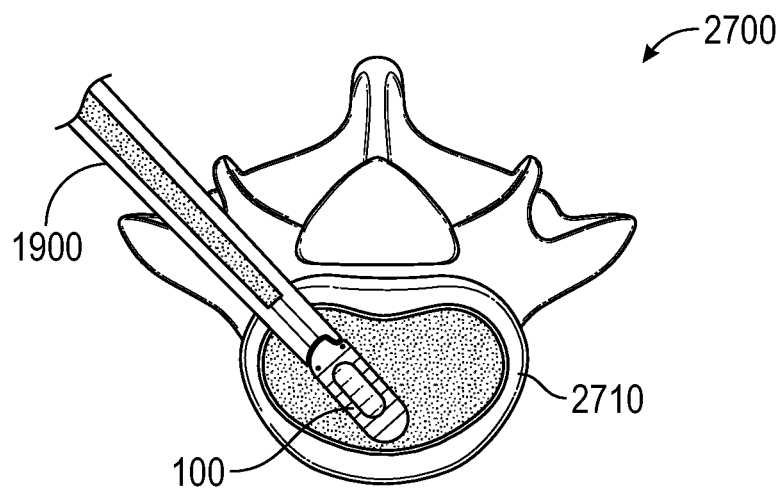
Figure 27B:
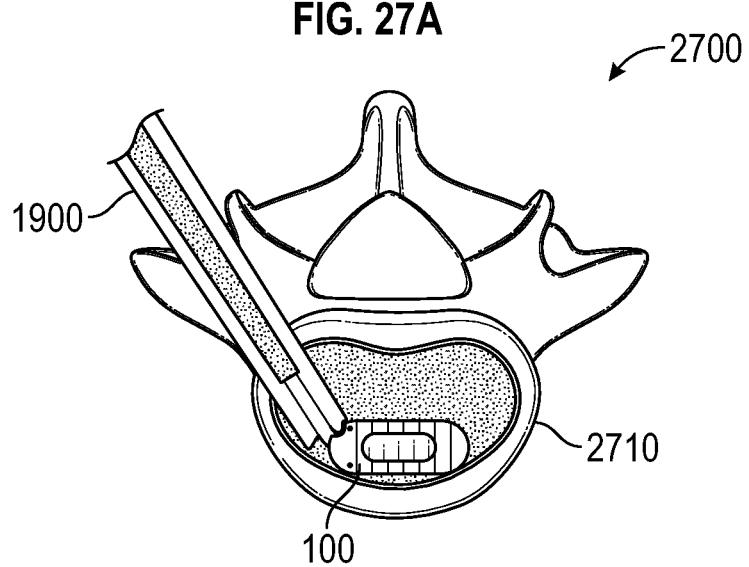
Figure 27C:
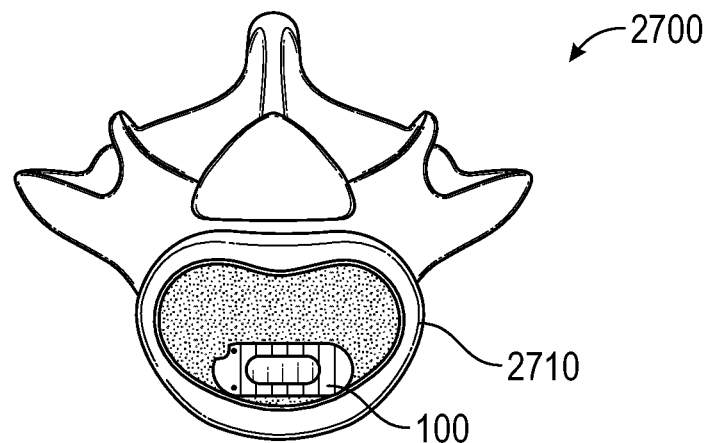
Figure 28A:
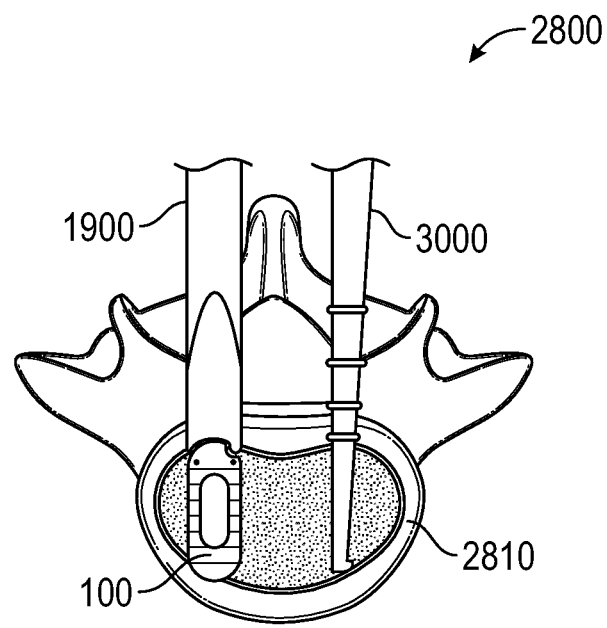
Figure 28B:
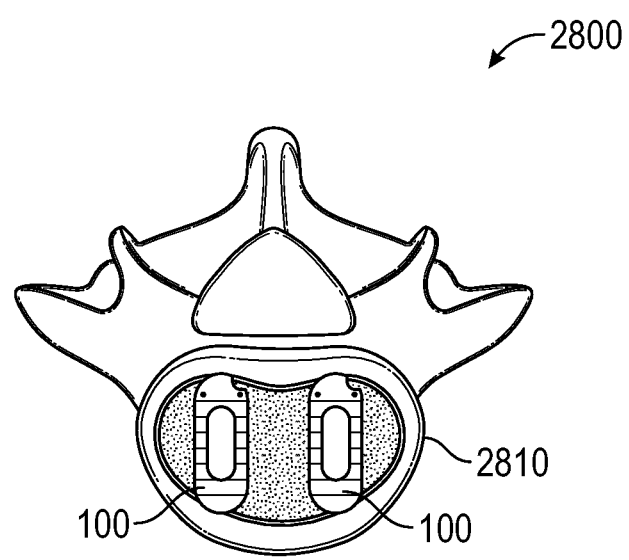
Figure 29:
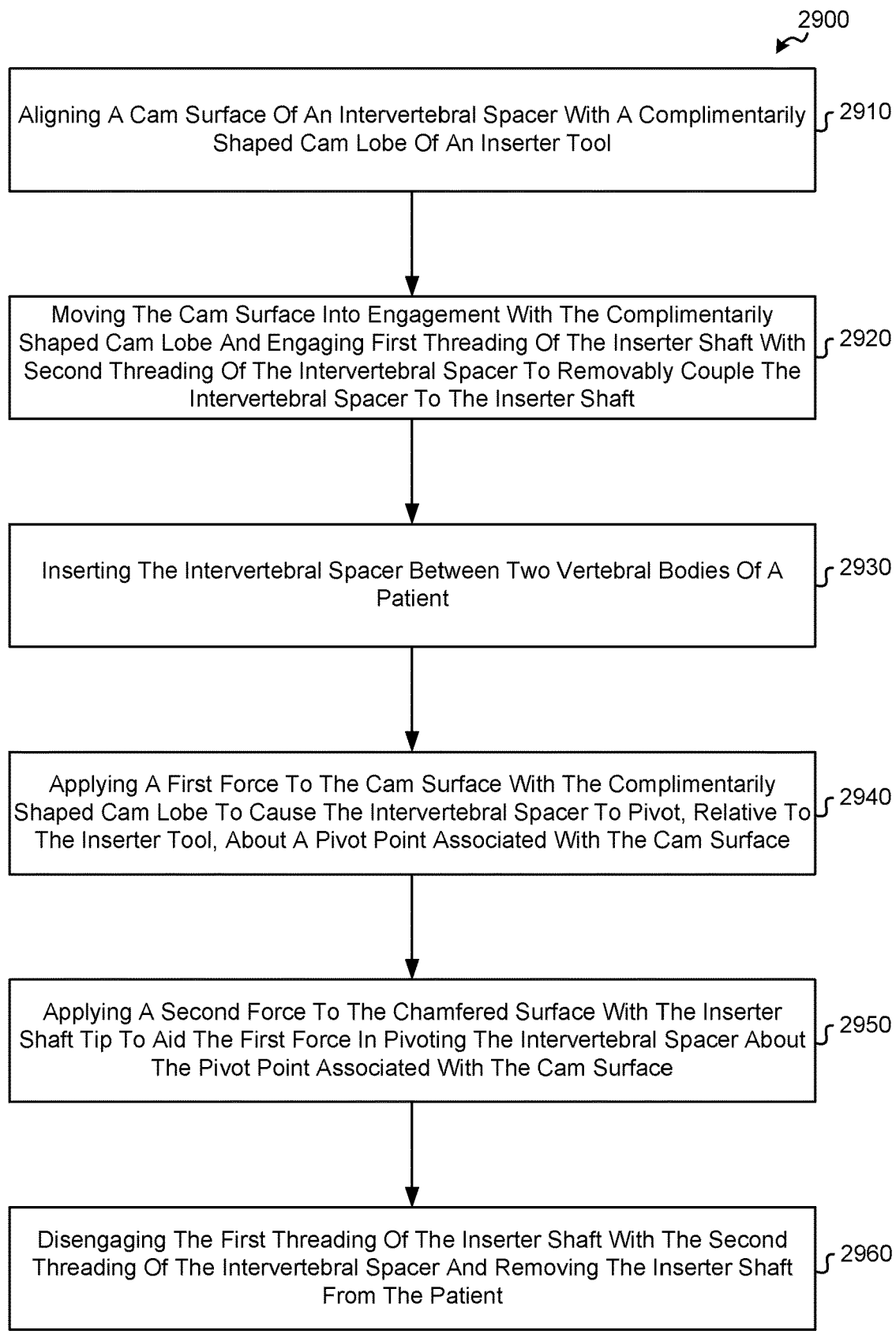

FIG. 19F is a left side view of the inserter tool 1900 of FIG. 19A;

FIG. 19G illustrates the distal end 1912 of the inserter tool 1900 of FIG. 19A with an extended inserter shaft tip 1943;

FIG. 19H illustrates the distal end 1912 of the inserter tool 1900 of FIG. 19A with a retracted inserter shaft tip 1943;

FIG. 20A is a perspective side view of a proximal end of a shroud 1910 isolated from the inserter tool 1900 shown in FIG. 19A;

FIG. 20B is a perspective side view of a distal end of the shroud 1910 of FIG. 20A;

FIG. 20C is a close-up perspective view of the distal end of the shroud 1910 of FIG. 20A illustrating a cam lobe 1930;

FIG. 20D is a close-up side view of the distal end of the shroud 1910 of FIG. 20A illustrating the cam lobe 1930;

FIG. 21A is a perspective view of a proximal end of an inserter shaft 1940 isolated from the inserter tool 1900 shown in FIG. 19A;

FIG. 21B is a perspective view of a distal end of the inserter shaft 1940 of FIG. 21A;

FIG. 21C is a close-up perspective view of the distal end of the inserter shaft 1940 of FIG. 21A;

FIG. 21D is a close-up side view of the distal end of the inserter shaft 1940 of FIG. 21A;

FIG. 22A illustrates a spinal fusion system 2200 prior to assembly;

FIG. 22B illustrates the spinal fusion system 2200 of FIG. 22A after assembly;

FIG. 23 illustrates a spinal fusion system 2300 with an intervertebral spacer 100 that has been partially rotated via a first force 1951;

FIG. 24 illustrates a spinal fusion system 2400 with an intervertebral spacer 100 that has been partially rotated via a first force 1951 and a second force 1952;

FIG. 25 illustrates a spinal fusion system 2500 with an intervertebral spacer 100 that has been fully rotated via a first force 1951;

FIG. 26 illustrates a spinal fusion system 2600 with an intervertebral spacer 100 that has been fully rotated via a first force 1951 and a second force 1952;

FIG. 27A illustrates an example implantation process 2700 for an intervertebral spacer 100 relative to a vertebral body 2710, according to one embodiment of the present disclosure;

FIG. 27B illustrates rotation of the intervertebral spacer 100 of FIG. 27A relative to the vertebral body 2710;

FIG. 27C illustrates final placement of the intervertebral spacer 100 of FIG. 27A relative to the vertebral body 2710;

FIG. 28A illustrates an example implantation process 2800 for one or more intervertebral spacers 100 relative to a vertebral body 2810, according to one embodiment of the present disclosure;

FIG. 28B illustrates final placement of two intervertebral spacers 100 relative to the vertebral body 2810; and FIG. 29 illustrates a flowchart of a method 2900 for inserting an intervertebral spacer between two vertebral bodies of a patient, according to an embodiment of the present disclosure.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1A:
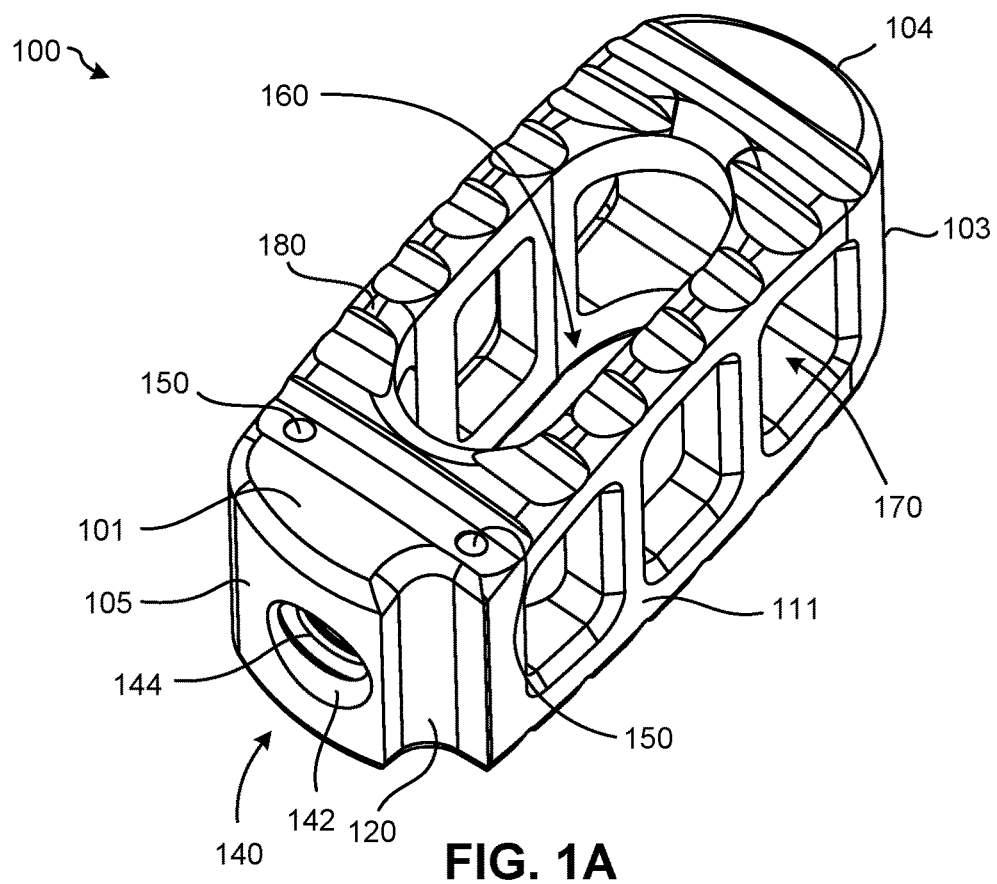
FIG. 1A is a perspective top view of a proximal end of an intervertebral spacer 100, according to an embodiment of the present disclosure.
Figure 1B:
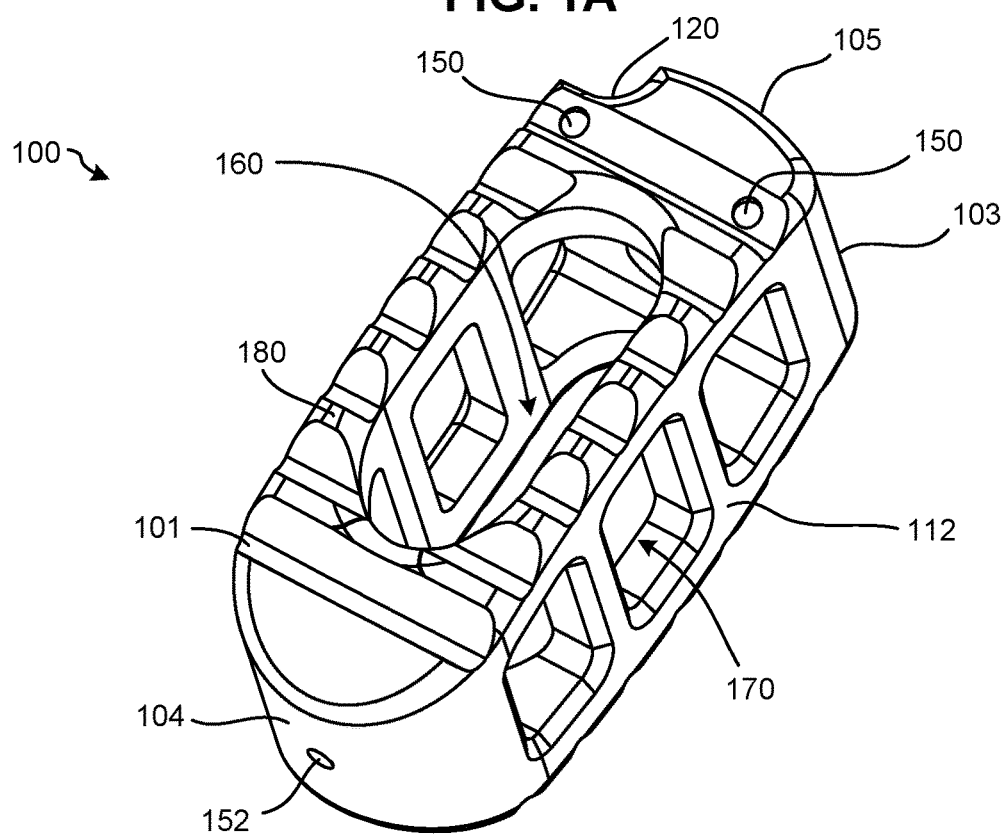
FIG. 1B is a perspective top view of a distal end of the intervertebral spacer 100 of FIG. 1A.
Figure 1C:
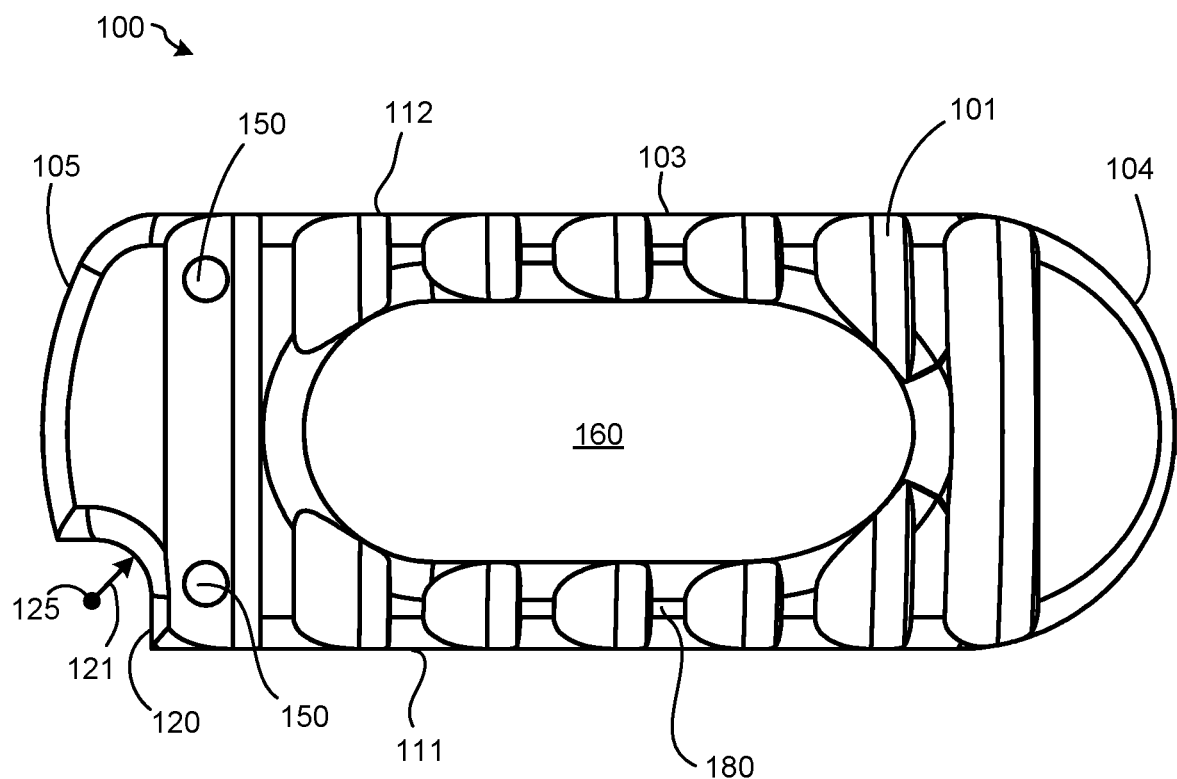
FIG. 1C is a top view of the intervertebral spacer 100 of FIG. 1A.
Figure 1D:
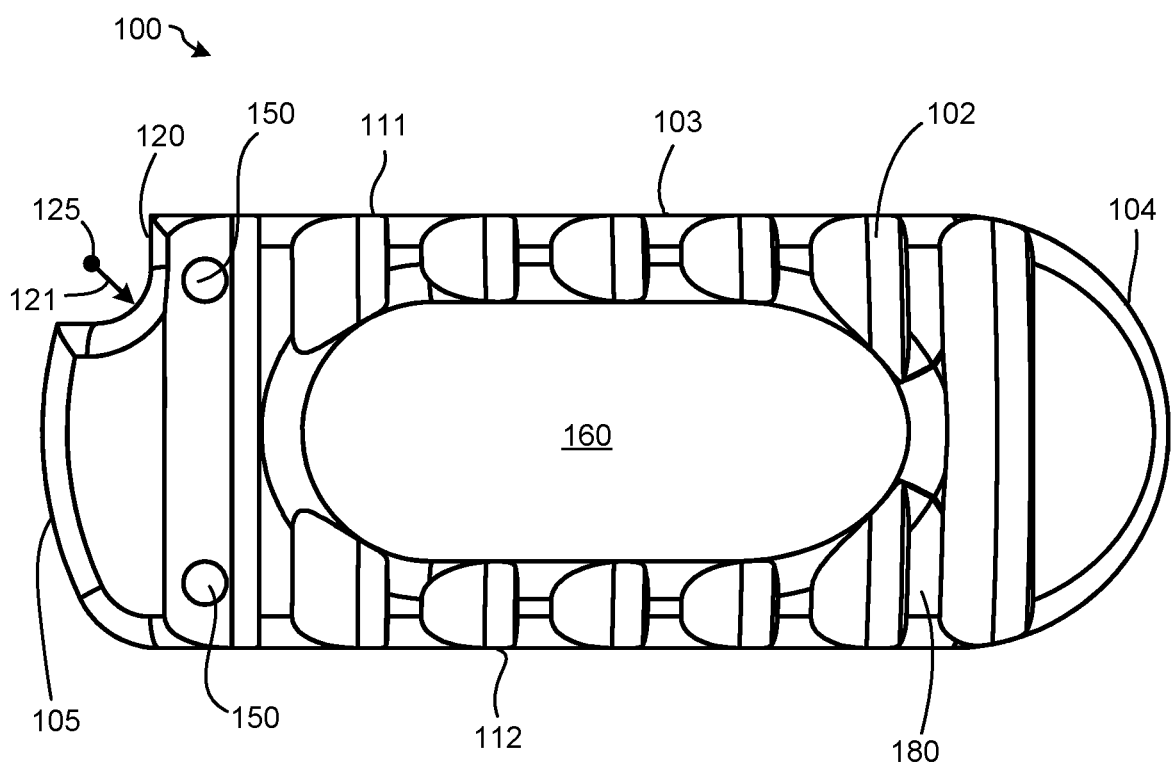
FIG. 1D is a bottom view of the intervertebral spacer 100 of FIG. 1A.
Figure 1E:
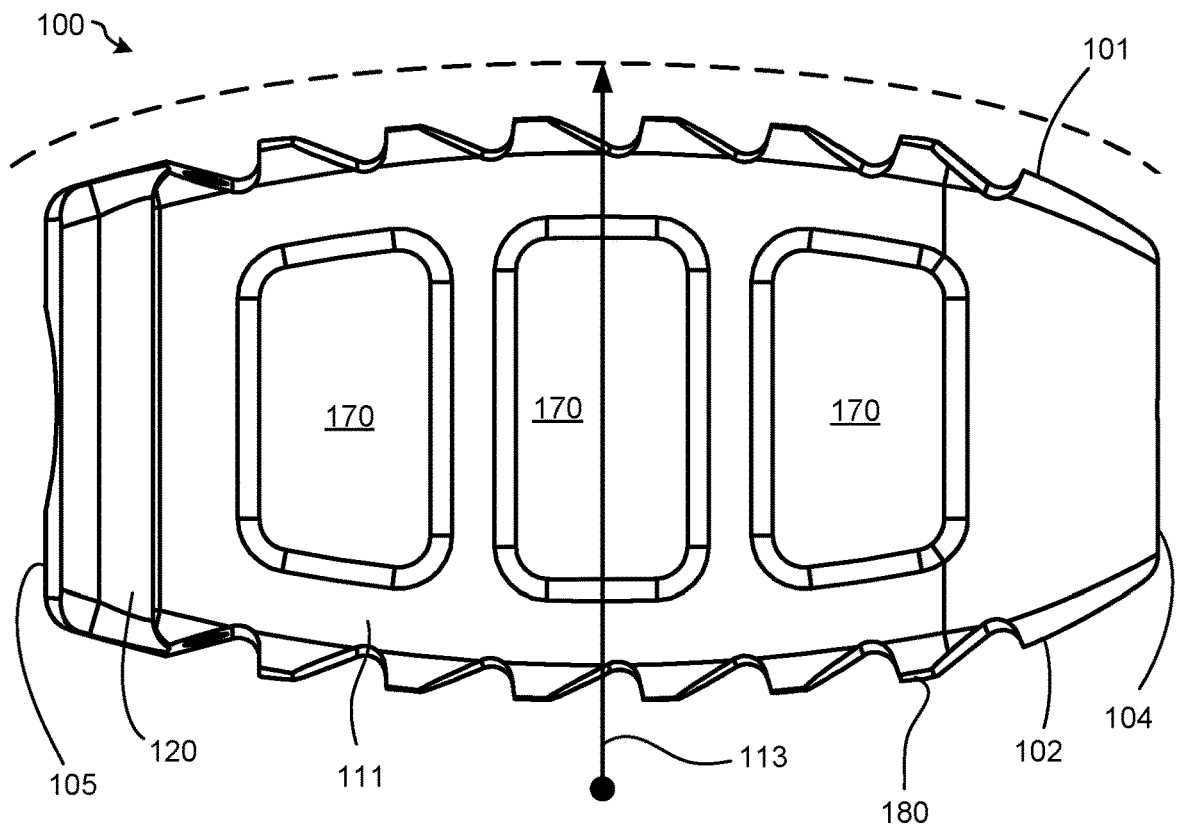
FIG. 1E illustrates a first side of the intervertebral spacer 100 of FIG. 1A.
Figure 1F:
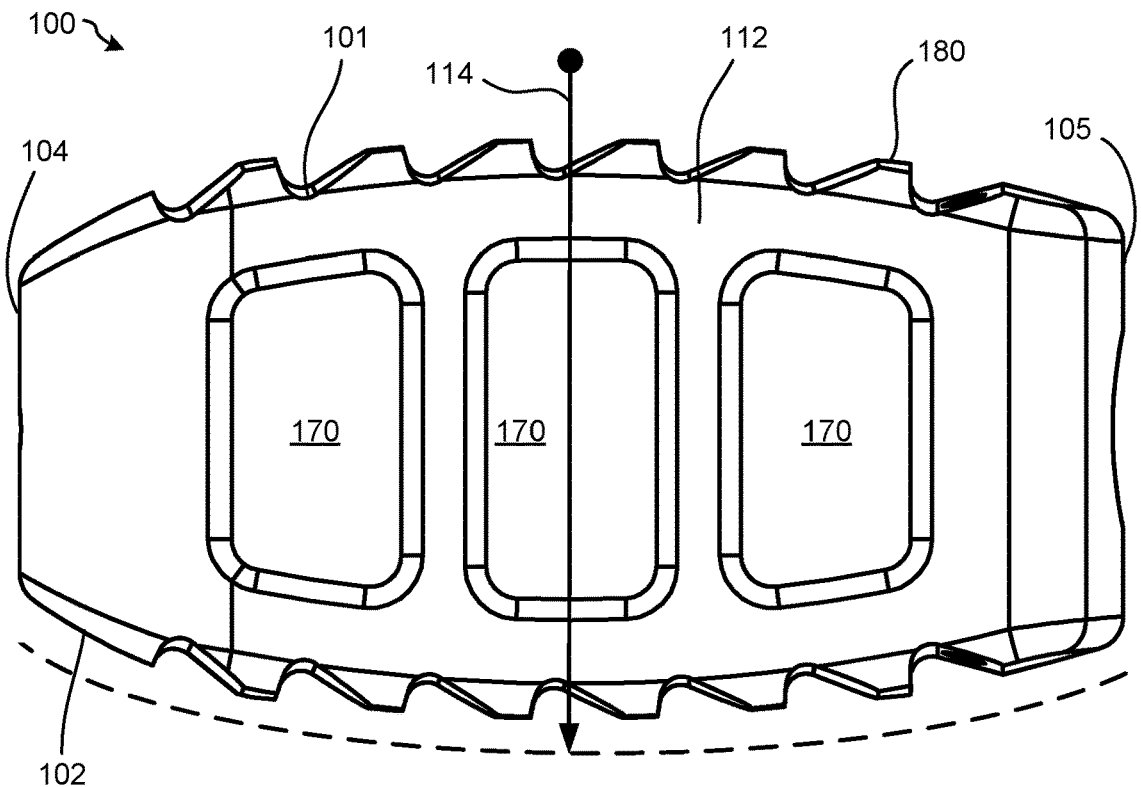
FIG. 1F illustrates a second side of the intervertebral spacer 100 of FIG. 1A.
Figure 1G:
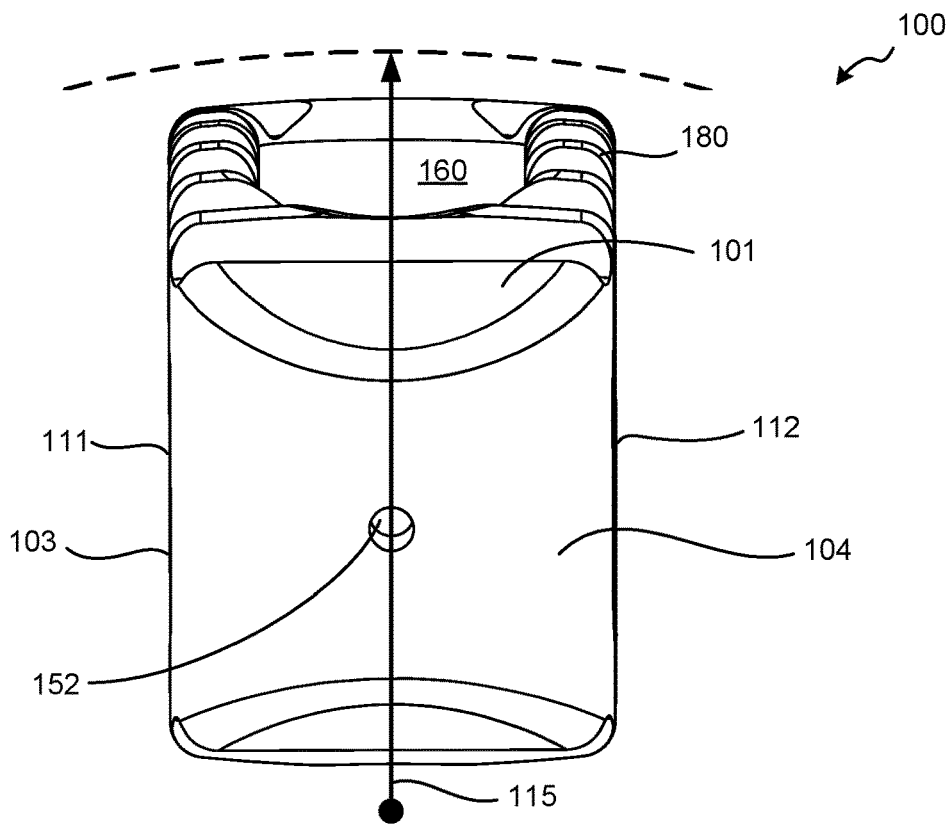
FIG. 1G is a perspective view of the distal end of the intervertebral spacer 100 of FIG. 1A.
Figure 1H:
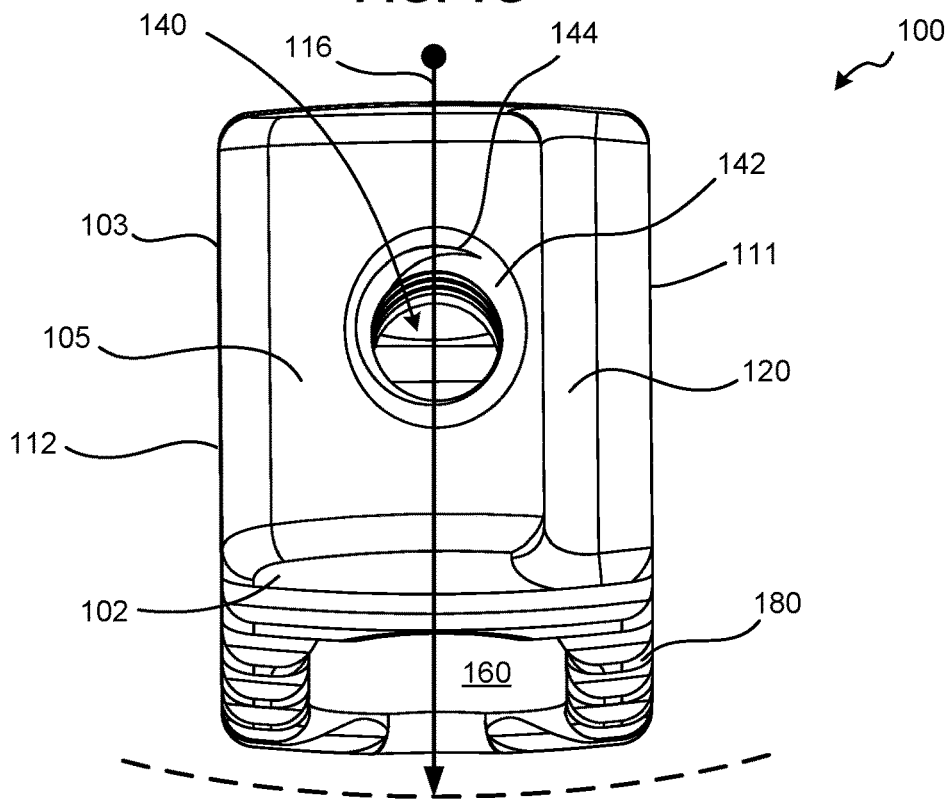
FIG. 1H is a perspective view of the proximal end of the intervertebral spacer 100 of FIG. 1A.

FIGS. 1A-1H illustrate various views of an intervertebral spacer 100, according to an embodiment of the present disclosure. Specifically, FIG. 1A is a perspective top view of a proximal end 105 of the intervertebral spacer 100; FIG. 1B is a perspective top view of a distal end 104 of the intervertebral spacer 100; FIG. 1C is a top view of the intervertebral spacer 100; FIG. 1D is a bottom view of the intervertebral spacer 100; FIG. 1E illustrates a first side 111 of the intervertebral spacer 100; FIG. 1F illustrates a second side 112 of the intervertebral spacer 100; FIG. 1G is a perspective view of the distal end 104 of the intervertebral spacer 100; and FIG. 1H is a perspective view of the proximal end 105 of the intervertebral spacer 100.

The intervertebral spacer 100 may generally include a superior surface 101 configured to engage a superior vertebral body (not shown), an inferior surface 102 configured to engage an inferior vertebral body (not shown), and a peripheral wall 103 extending from the superior surface 101 to the inferior surface 102. The peripheral wall 103 may generally comprise the distal end 104, the proximal end 105, the first side 111, and the second side 112 of the intervertebral spacer 100.

The proximal end 105 of the intervertebral spacer 100 may include a cam surface 120 that is rotatable against a complementary cam surface of a suitable inserter tool such that a first force causes the intervertebral spacer 100 to pivot, relative to the inserter tool, about a pivot point 125 associated with the cam surface 120, as will be discussed in more detail below with respect to FIGS. 22A-26. The cam surface 120 may comprise a concave surface having a first radius of curvature 121, as shown in FIGS. 1C and 1D. In at least one embodiment, the first radius of curvature 121 may be about 1.25 mm. In other embodiments, the first radius of curvature 121 may be between about 0.5 mm and about 4 mm. However, it will be understood that in other embodiments (not shown), the cam surface 120 may alternatively comprise a convex surface. The cam surface 120 may also be located closer to the first side 111 of the intervertebral spacer 100 than the second side 112 of the intervertebral spacer 100, or vice versa.

The proximal end 105 of the intervertebral spacer 100 may also include an aperture 140 formed therein, as well as a chamfered surface 142 proximate the aperture 140. The chamfered surface 142 may be configured to receive a second force from a suitable inserter shaft tip to aid the first force in pivoting the intervertebral spacer 100 about the pivot point 125 associated with the cam surface 120, as will be discussed in more detail below with respect to FIGS. 22A-26. Moreover, the aperture 140 may include threading 144 formed within the aperture 140 to facilitate coupling of the intervertebral spacer 100 to a suitable inserter shaft, which will also be discussed in more detail below with respect to FIGS. 22A-26.

As shown in FIG. 1E, the superior surface 101 of the intervertebral spacer 100 may comprise a third radius of curvature 113 that extends from the proximal end 105 of the intervertebral spacer 100 to the distal end 104 of the intervertebral spacer 100. Likewise, the inferior surface 102 of the intervertebral spacer 100 may comprise a fourth radius of curvature 114 that extends from the proximal end 105 of the intervertebral spacer 100 to the distal end 104 of the intervertebral spacer 100, as shown in FIG. 1F.

In at least one embodiment, the fourth radius of curvature 114 may be substantially equal to the third radius of curvature 113. As defined herein, "substantially equal to" means "equal to," or within about a + or −10% relative variance from one another.

In some embodiments, the third and fourth radii of curvatures 113, 114 may each range from about 300 mm to about 60 mm.

In a particular embodiment, the third and fourth radii of curvatures 113, 114 may each be about 42.45 mm.

As shown in FIG. 1G, the superior surface 101 of the intervertebral spacer 100 may comprise a fifth radius of curvature 115 that extends from the first side 111 of the intervertebral spacer 100 to the second side 112 of the intervertebral spacer 100. Likewise, the inferior surface 102 of the intervertebral spacer 100 may comprise a sixth radius of curvature 116 that extends from the first side 111 of the intervertebral spacer 100 to the second side 112 of the intervertebral spacer 100, as shown in FIG. 1H.

In at least one embodiment, the sixth radius of curvature 116 may be substantially equal to the fifth radius of curvature 115.

In some embodiments, the fifth and sixth radii of curvatures 115, 116 may each range from about 300 mm to about 60 mm.

In a particular embodiment, fifth and sixth radii of curvatures 115, 116 may each be about 41.5 mm.

In this manner, the third, fourth, fifth, and sixth radii of curvatures 113, 114, 115, 116 of the superior and inferior surfaces 101, 102 of the intervertebral spacer 100 may together result in a dome shape with "high spots" (or maximal thickness of the intervertebral spacer 100) toward the centers of the superior and inferior surfaces 101, 102. These high spots may help reduce frictional forces acting upon the superior and inferior surfaces 101, 102 when the intervertebral spacer 100 is inserted between two vertebral bodies. In this manner, these high spots may help reduce the force needed to rotate the intervertebral spacer 100 after it has been inserted between two vertebral bodies, as will be discussed below in more detail with respect to FIGS. 22A-26.

The intervertebral spacer 100 may include a central bone graft aperture 160 formed through the superior and inferior surfaces 101, 102 of the intervertebral spacer 100, as well as one or more side bone graft apertures 170 formed in the first and second sides 111, 112 of the intervertebral spacer 100. The central bone graft aperture 160 and the one or more side bone graft apertures 170 may each be configured to receive bone graft material (not shown) and/or other suitable materials that are known in the art. The intervertebral spacer 100 may also include one or more serrated teeth 180 formed in the superior and inferior surfaces 101, 102 of the intervertebral spacer 100. The one or more serrated teeth 180 may be configured to help stabilize the intervertebral spacer 100 between adjacent vertebral bodies during the fusion process. Moreover, bone graft and/or other suitable materials may also be placed between adjacent serrated teeth 180 of the intervertebral spacer 100 in order to enhance the fusion process and/or help stabilize the intervertebral spacer 100 between adjacent vertebral bodies during the fusion process.

Figure 4:
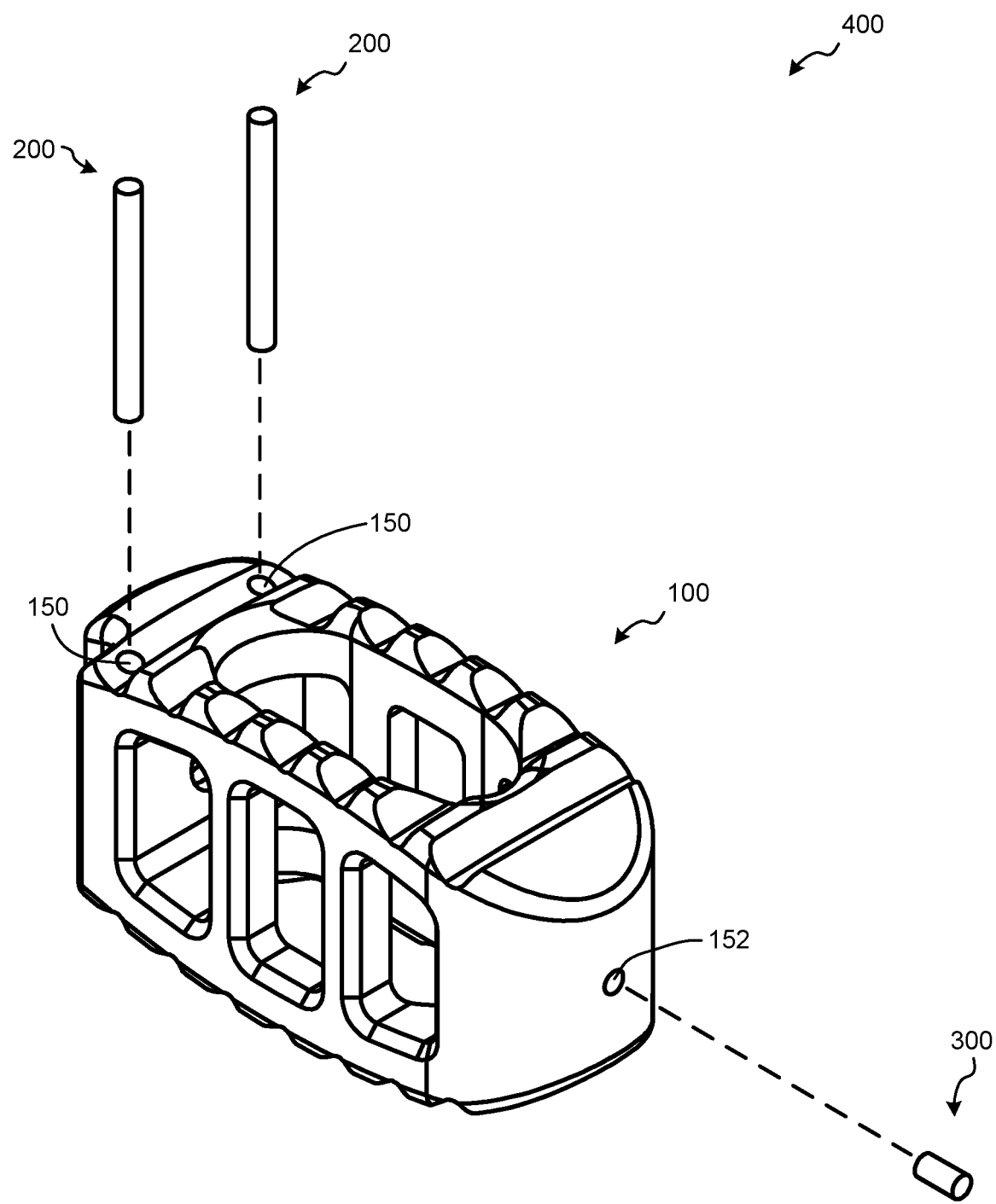
FIG. 4 is an exploded view of the intervertebral spacer 100 of FIG. 1A and the first and second radiopaque markers 200, 300 of FIGS. 2A-3B prior to assembly.
Figure 5A:
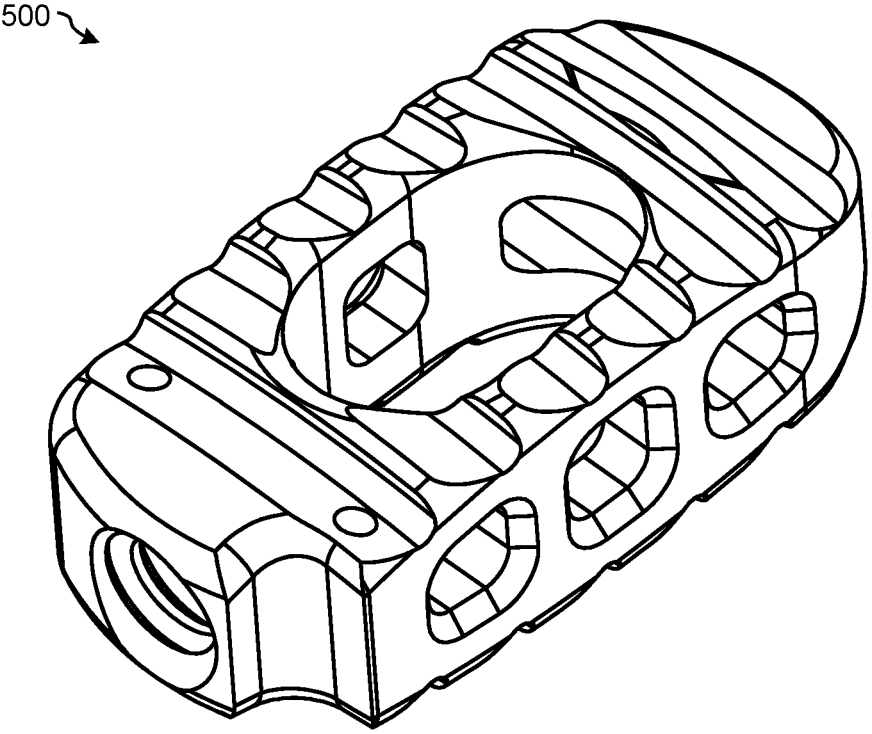
FIG. 5A is a perspective top view of a proximal end of an intervertebral spacer 500, according to an embodiment of the present disclosure.
Figure 5B:
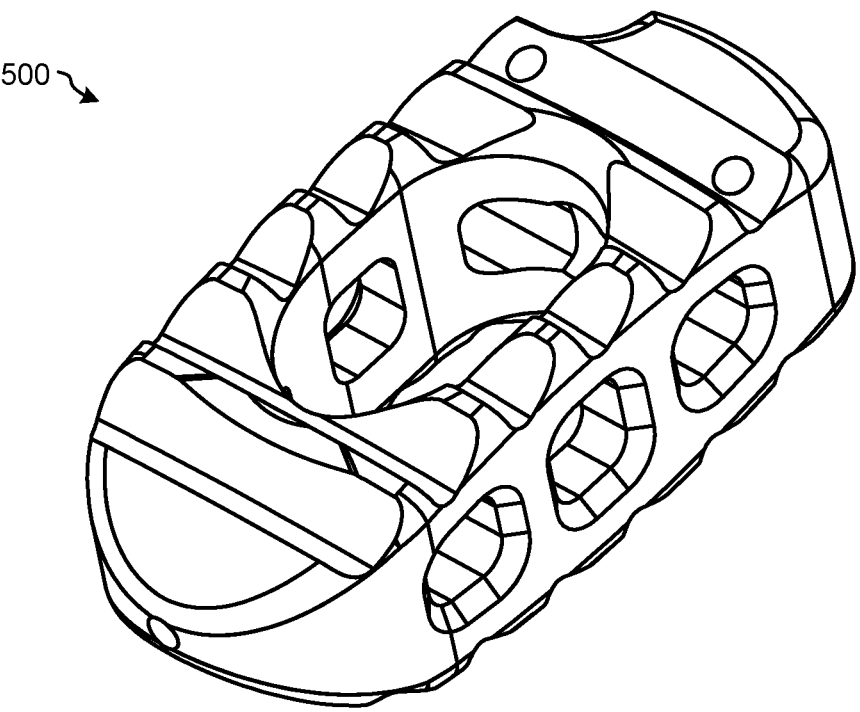
FIG. 5B is a perspective top view of a distal end of the intervertebral spacer 500 of FIG. 5A.
Figure 5C:
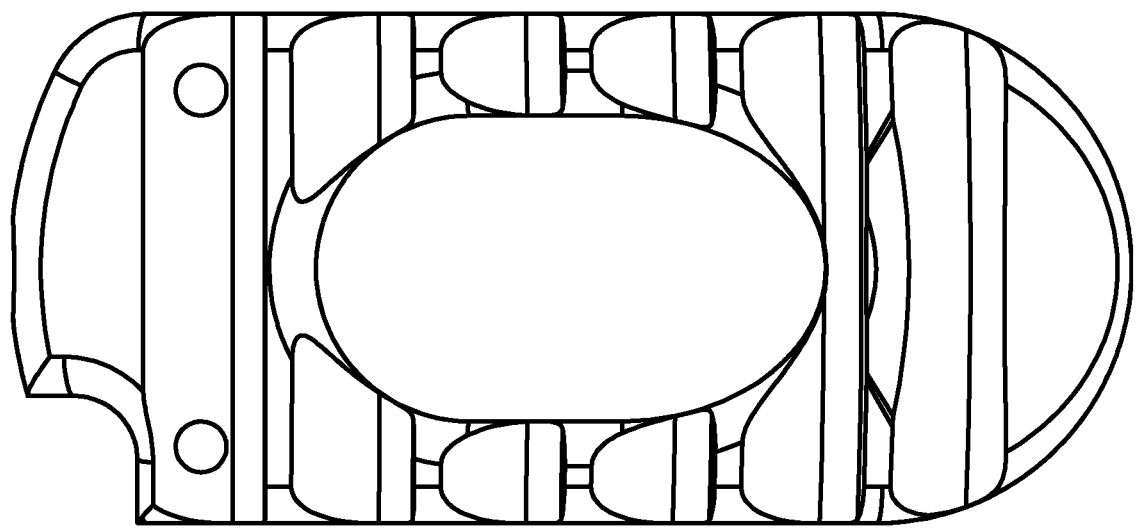
FIG. 5C is a top view of the intervertebral spacer 500 of FIG. 5A.
Figure 5D:
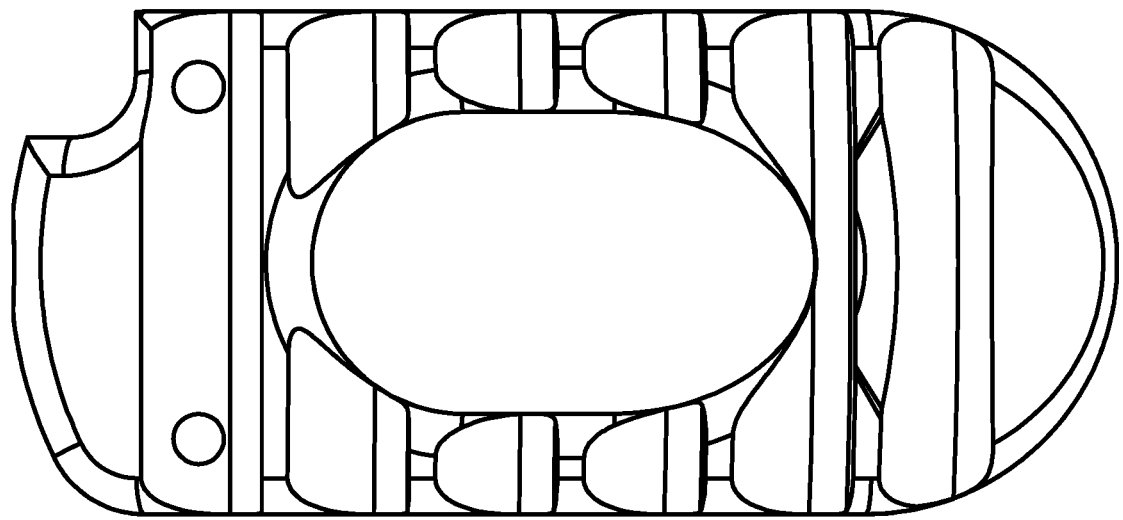
FIG. 5D is a bottom view of the intervertebral spacer 500 of FIG. 5A.
Figure 5E:
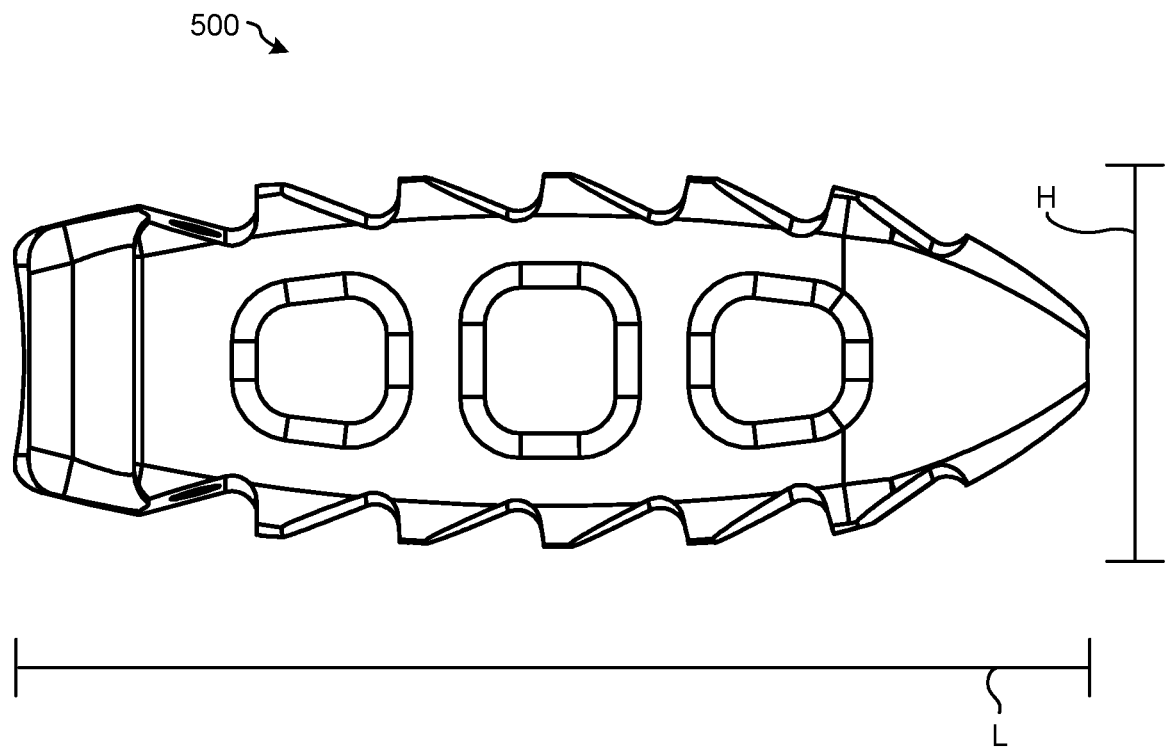
FIG. 5E illustrates a first side of the intervertebral spacer 500 of FIG. 5A.
Figure 5F:
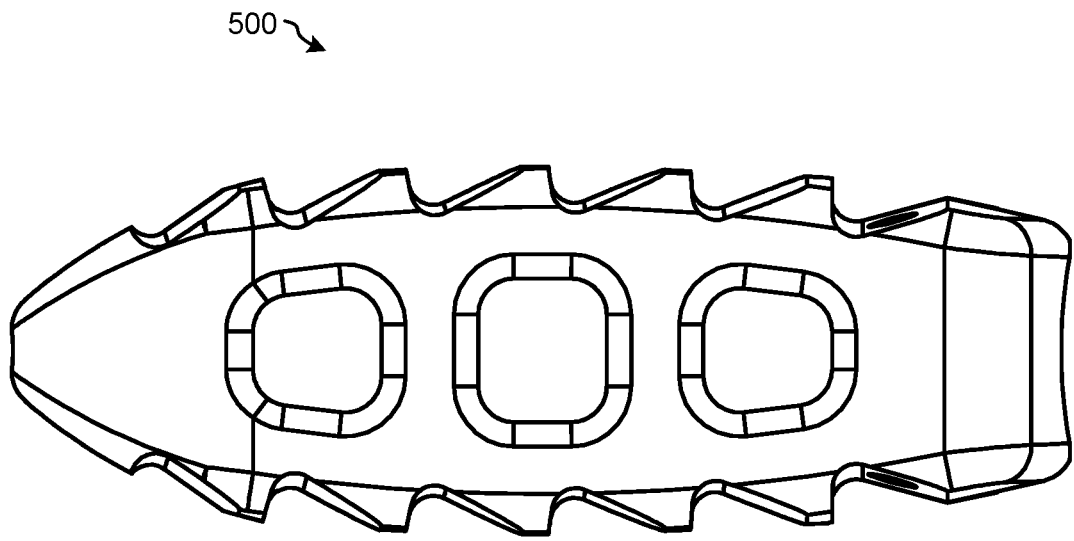
FIG. 5F illustrates a second side of the intervertebral spacer 500 of FIG. 5A.
Figure 5G:
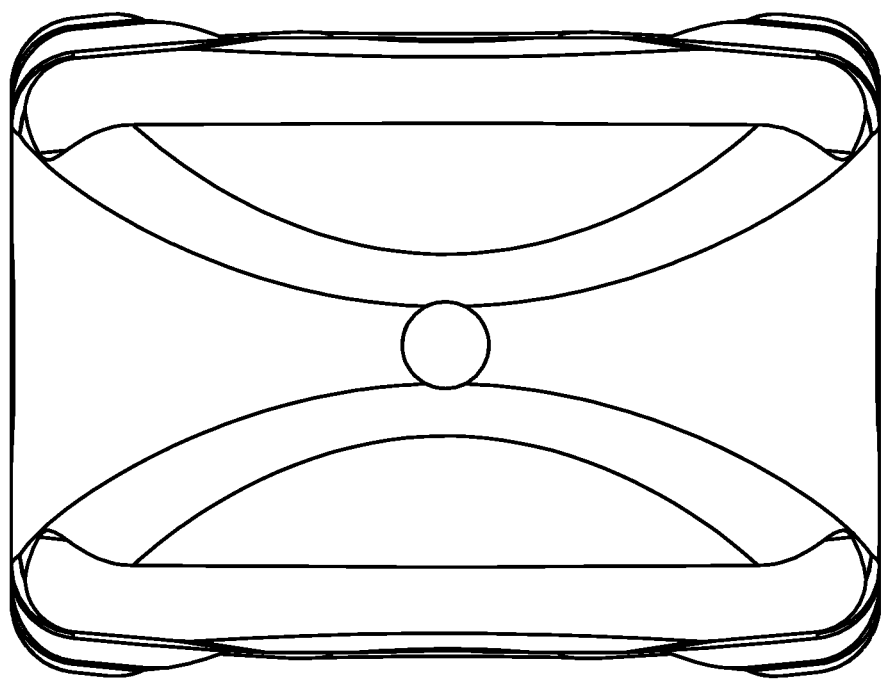
FIG. 5G illustrates the distal end of the intervertebral spacer 500 of FIG. 5A.
Figure 5H:
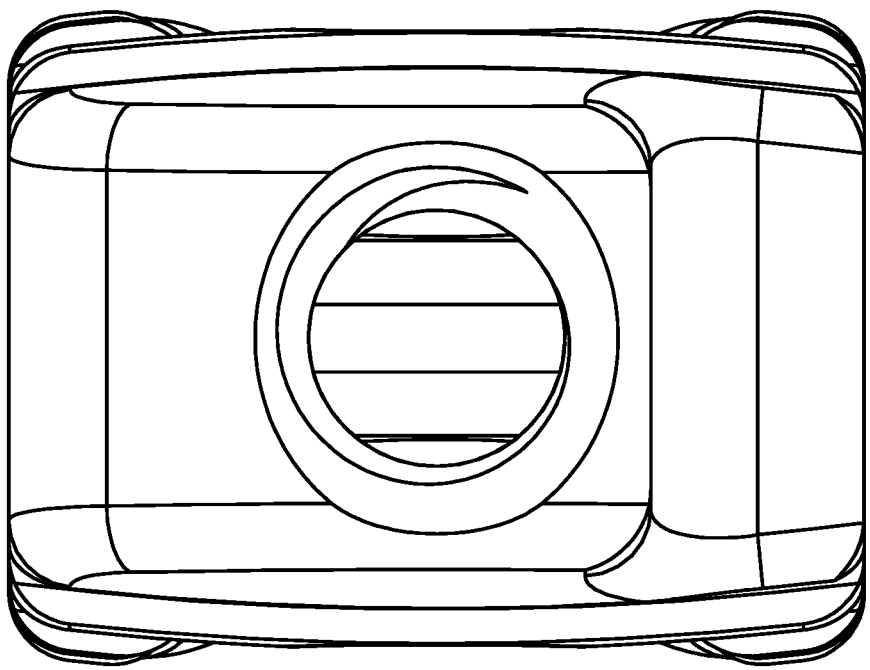
FIG. 5H illustrates the proximal end of the intervertebral spacer 500 of FIG. 5A.
Figure 6A:
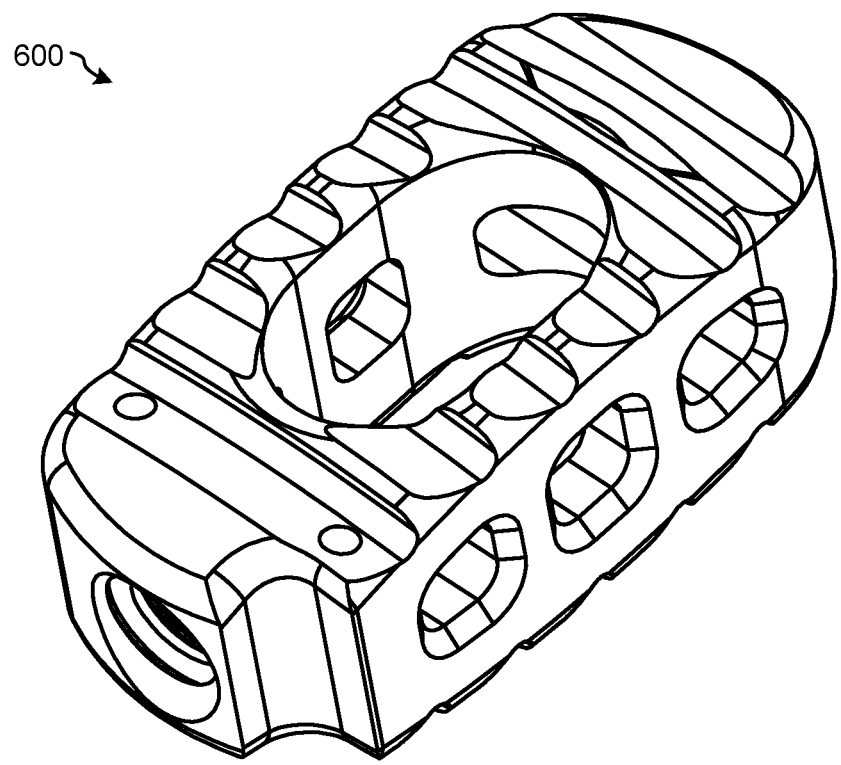
FIG. 6A is a perspective top view of a proximal end of an intervertebral spacer 600, according to an embodiment of the present disclosure.
Figure 6B:
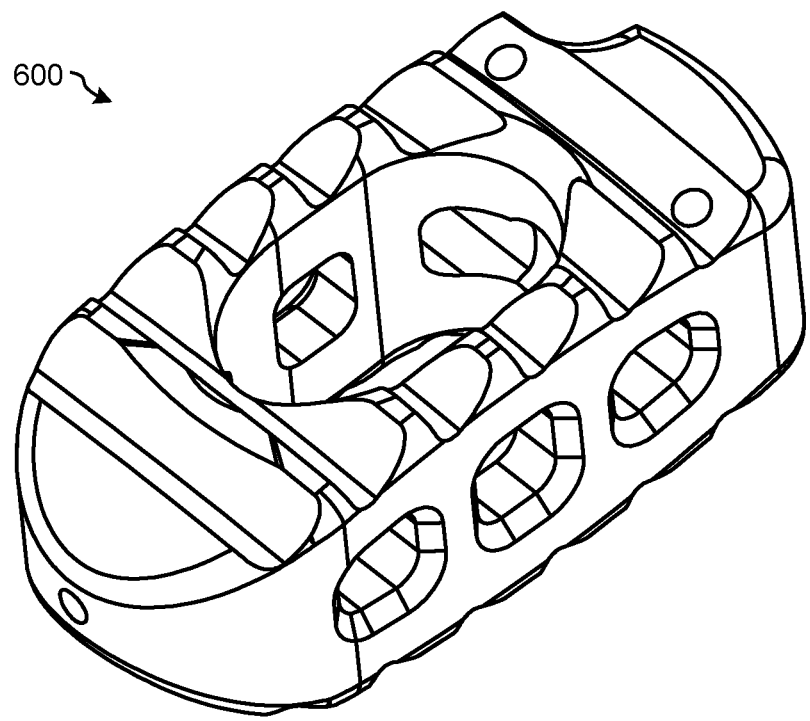
FIG. 6B is a perspective top view of a distal end of the intervertebral spacer 600 of FIG. 6A.
Figure 6C:
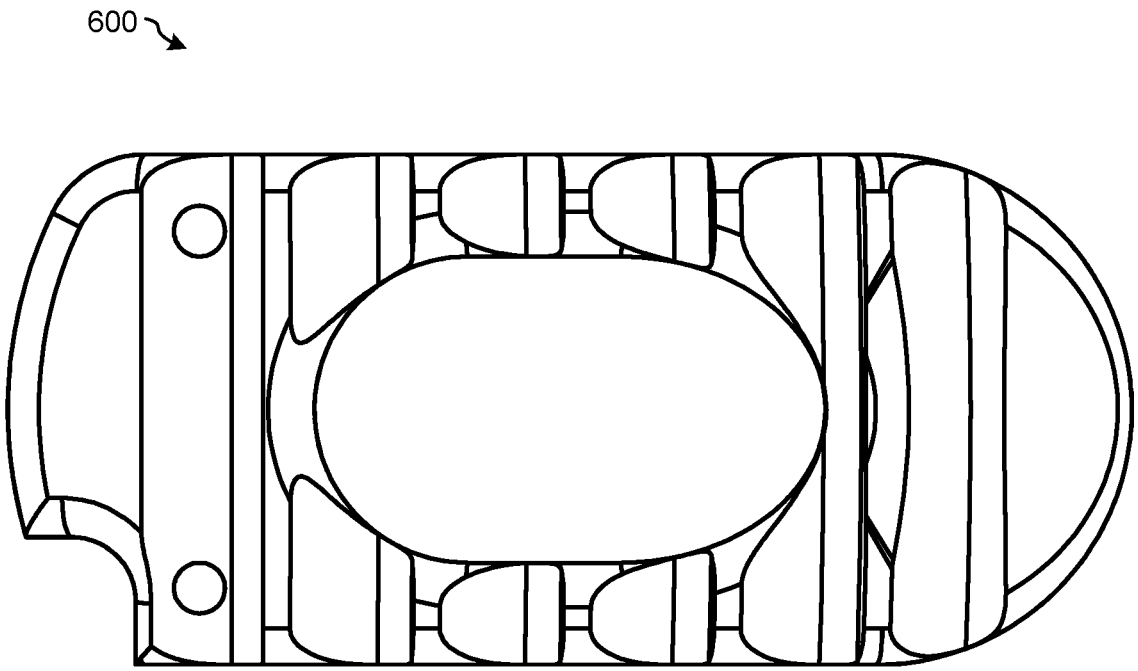
FIG. 6C is a top view of the intervertebral spacer 600 of FIG. 6A.
Figure 6D:
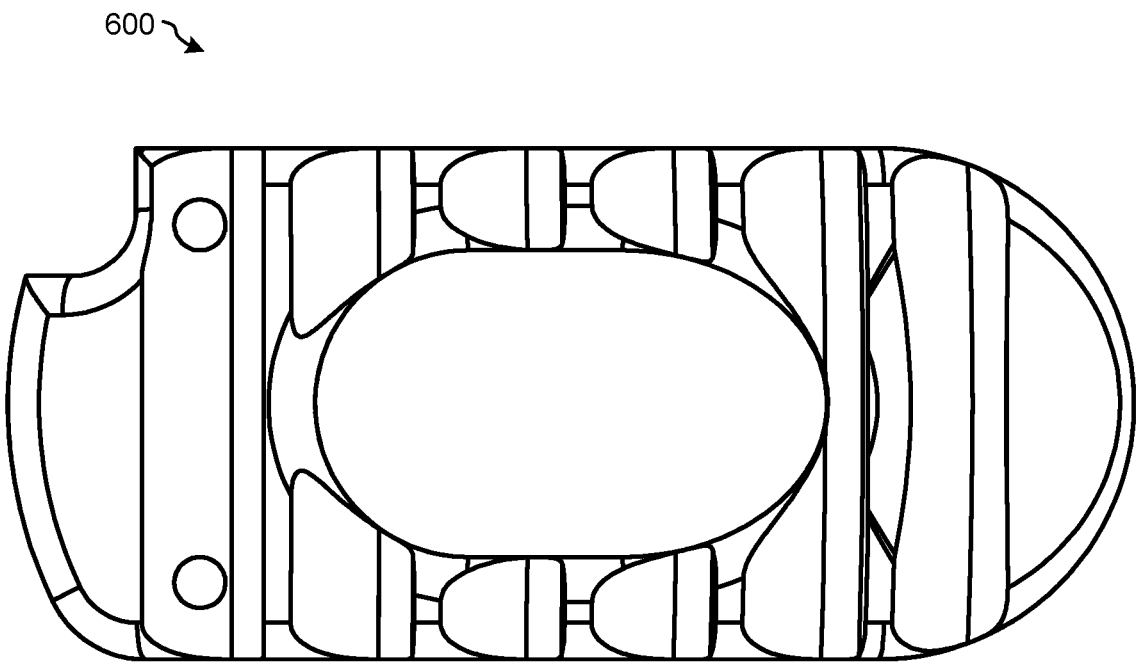
FIG. 6D is a bottom view of the intervertebral spacer 600 of FIG. 6A.
Figure 6E:
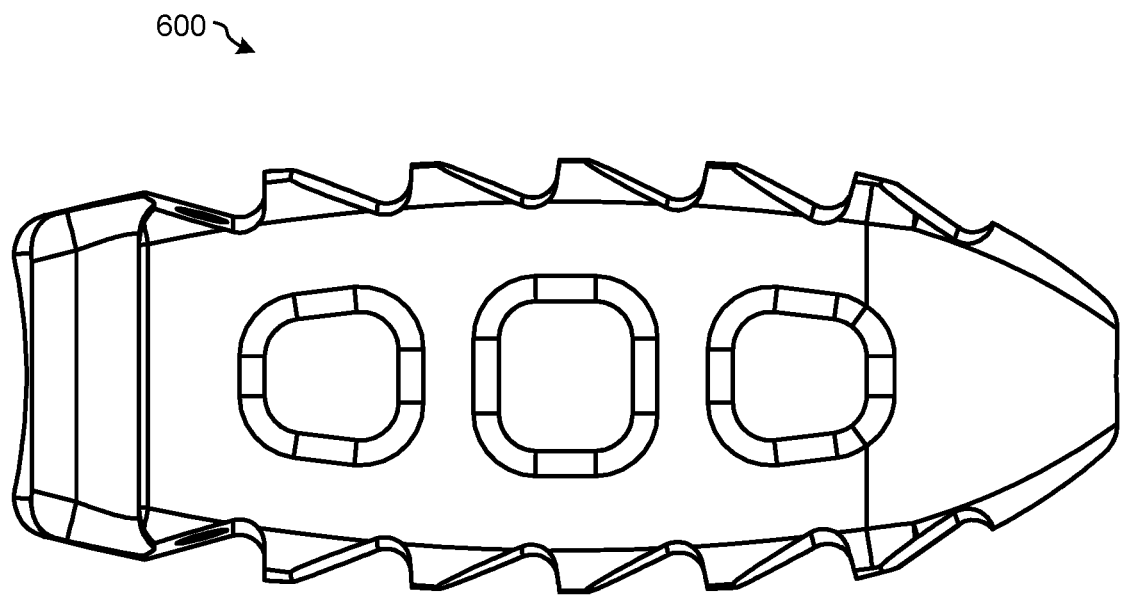
FIG. 6E illustrates a first side of the intervertebral spacer 600 of FIG. 6A.
Figure 6F:
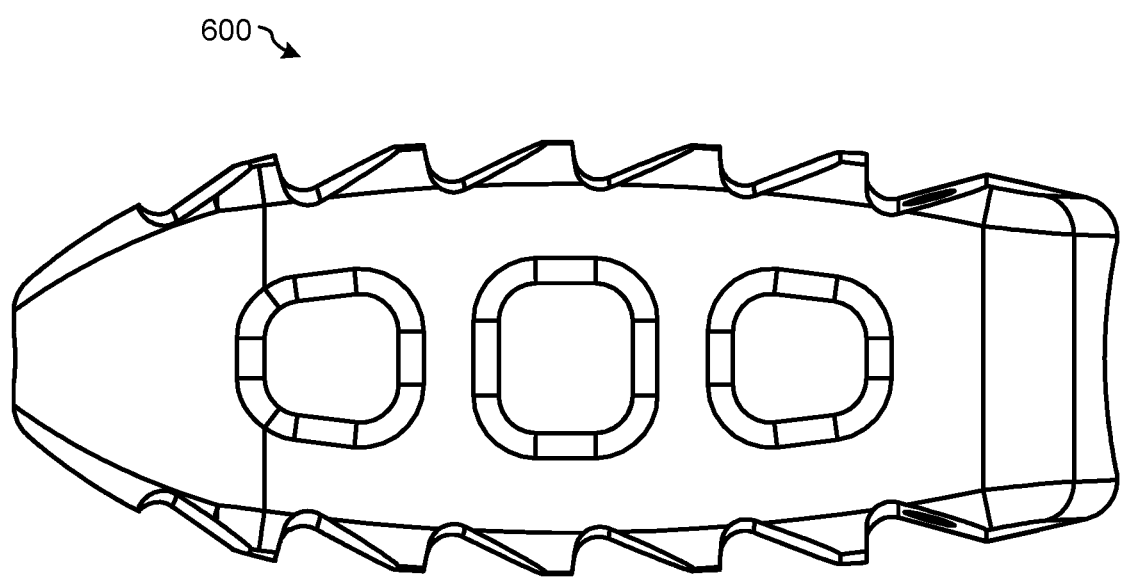
FIG. 6F illustrates a second side of the intervertebral spacer 600 of FIG. 6A.
Figure 6G:
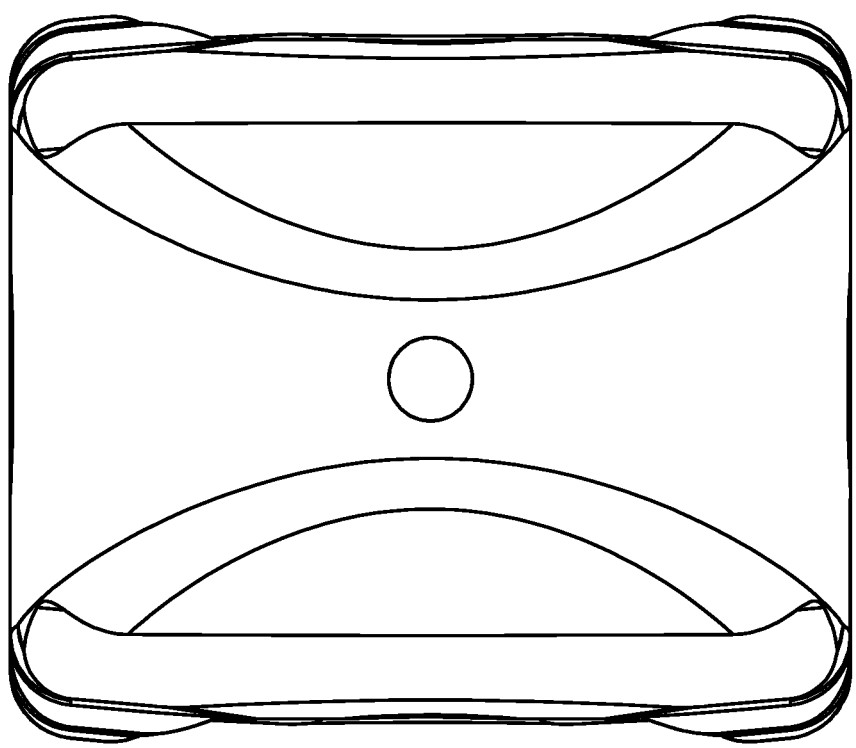
FIG. 6G illustrates the distal end of the intervertebral spacer 600 of FIG. 6A.
Figure 6H:
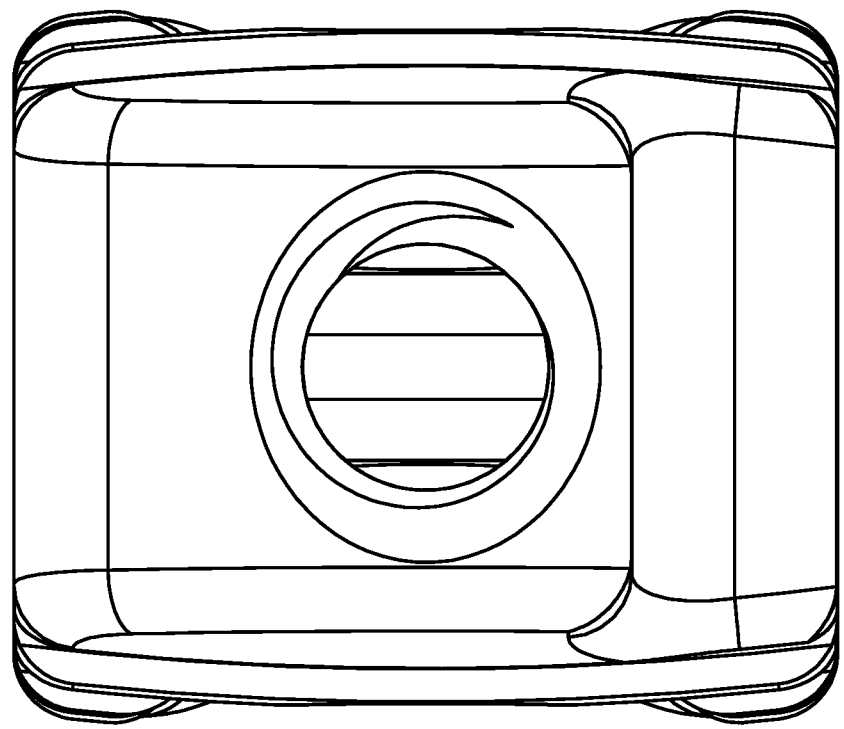
FIG. 6H illustrates the proximal end of the intervertebral spacer 600 of FIG. 6A.
Figure 7A:
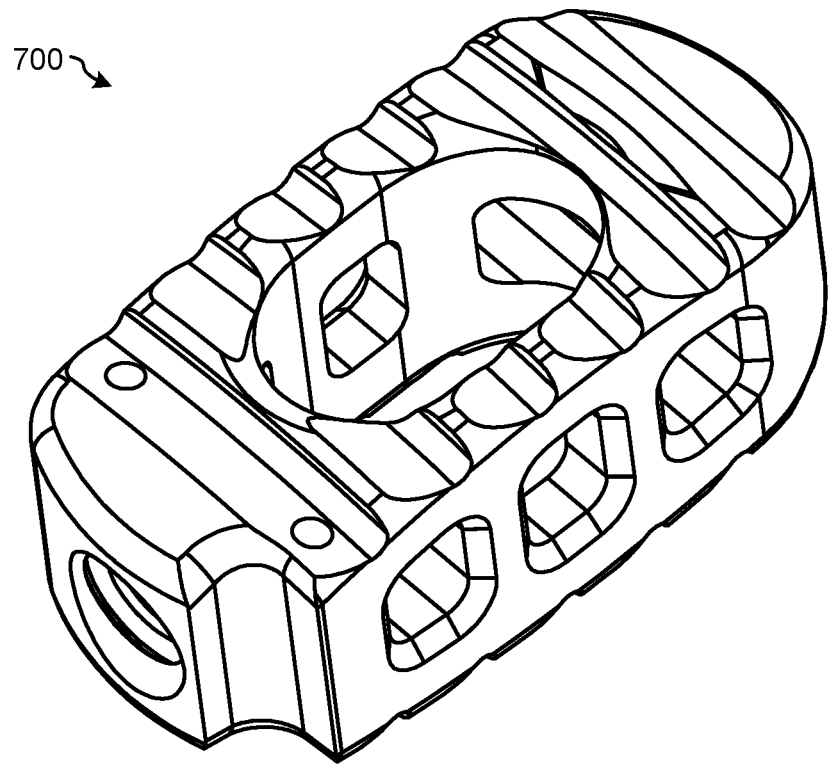
FIG. 7A is a perspective top view of a proximal end of an intervertebral spacer 700, according to an embodiment of the present disclosure.
Figure 7B:
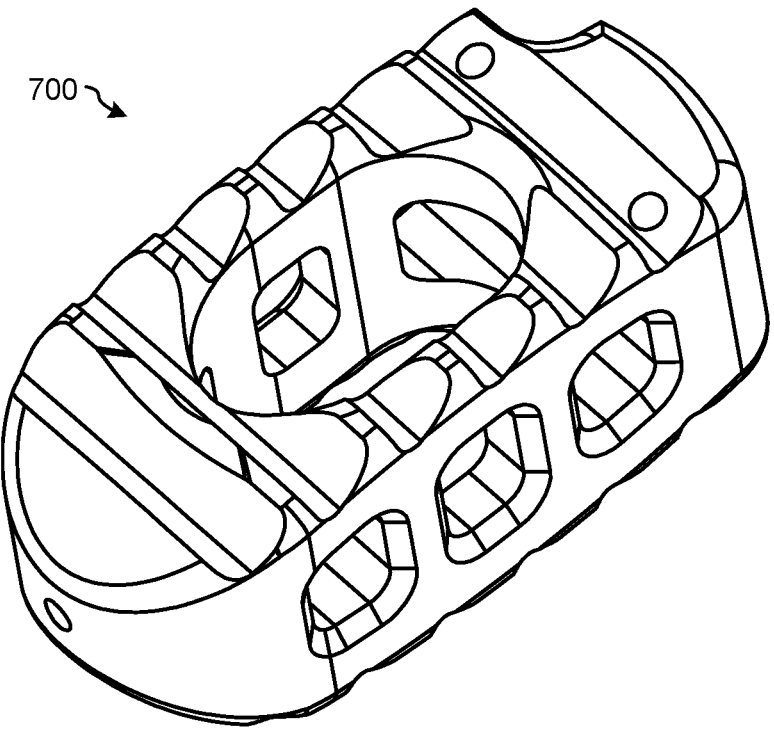
FIG. 7B is a perspective top view of a distal end of the intervertebral spacer 700 of FIG. 7A.
Figure 7C:
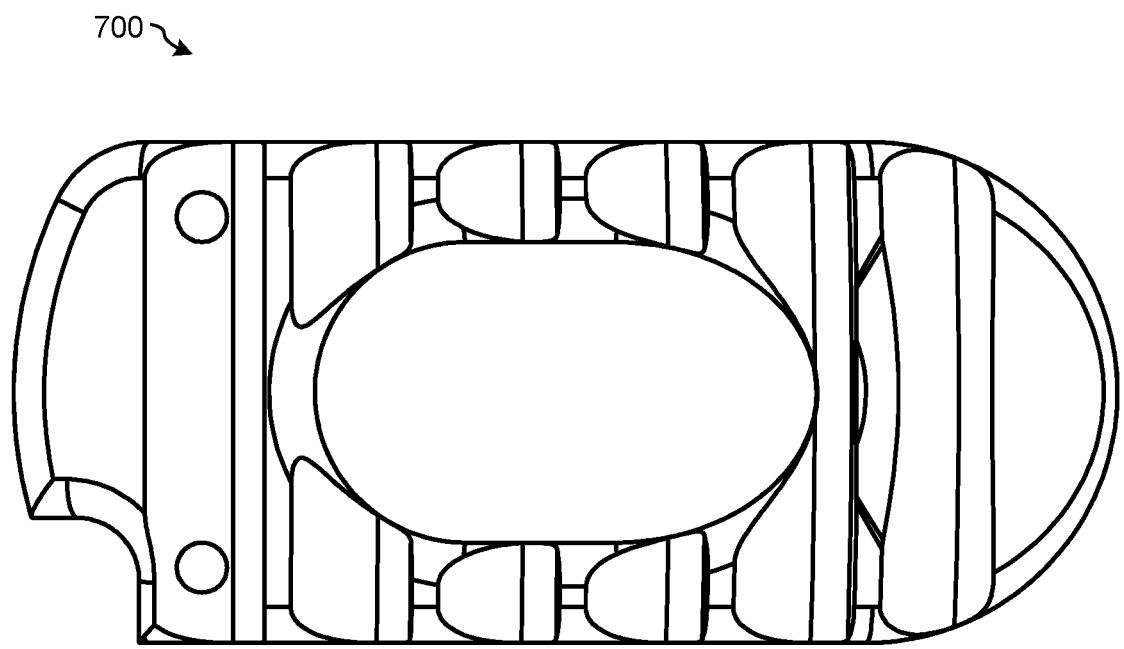
FIG. 7C is a top view of the intervertebral spacer 700 of FIG. 7A.
Figure 7D:
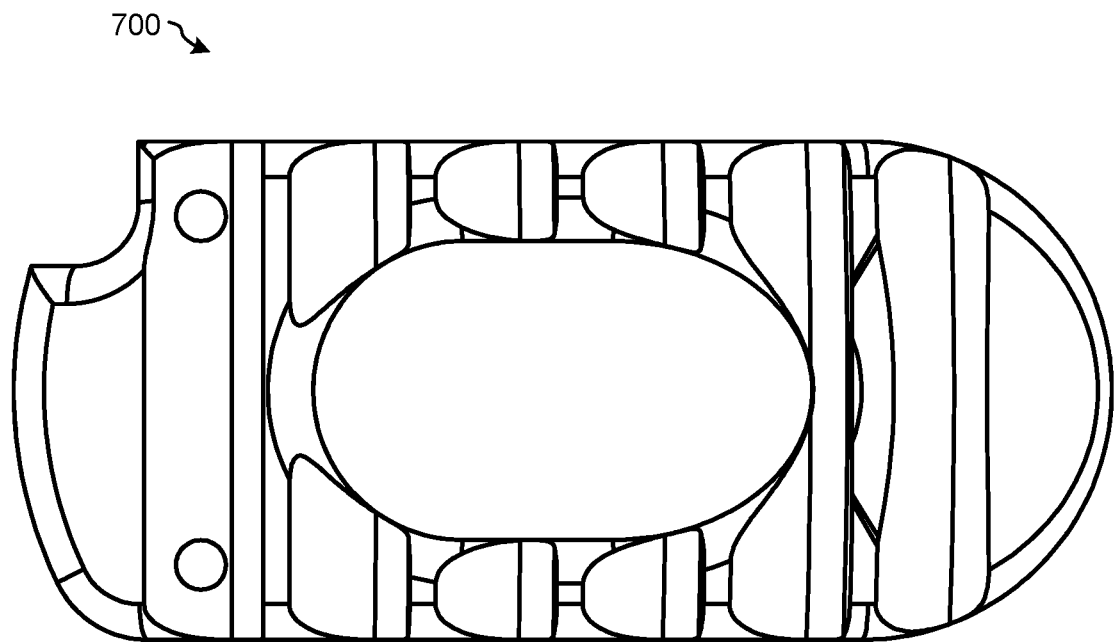
FIG. 7D is a bottom view of the intervertebral spacer 700 of FIG. 7A.
Figure 7E:
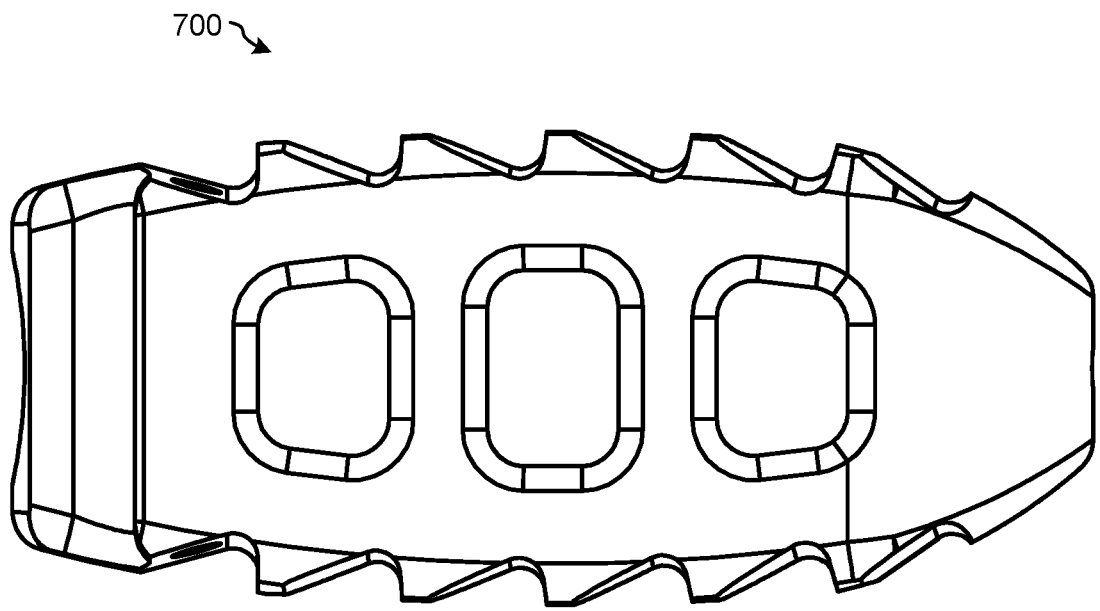
FIG. 7E illustrates a first side of the intervertebral spacer 700 of FIG. 7A.
Figure 7F:
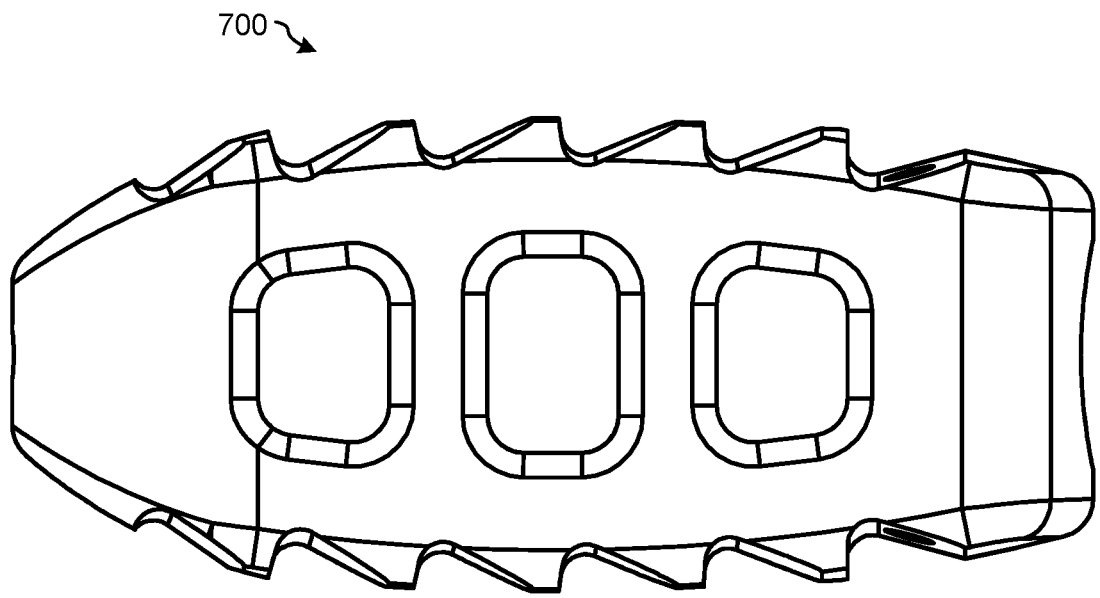
FIG. 7F illustrates a second side of the intervertebral spacer 700 of FIG. 7A.
Figure 7G:
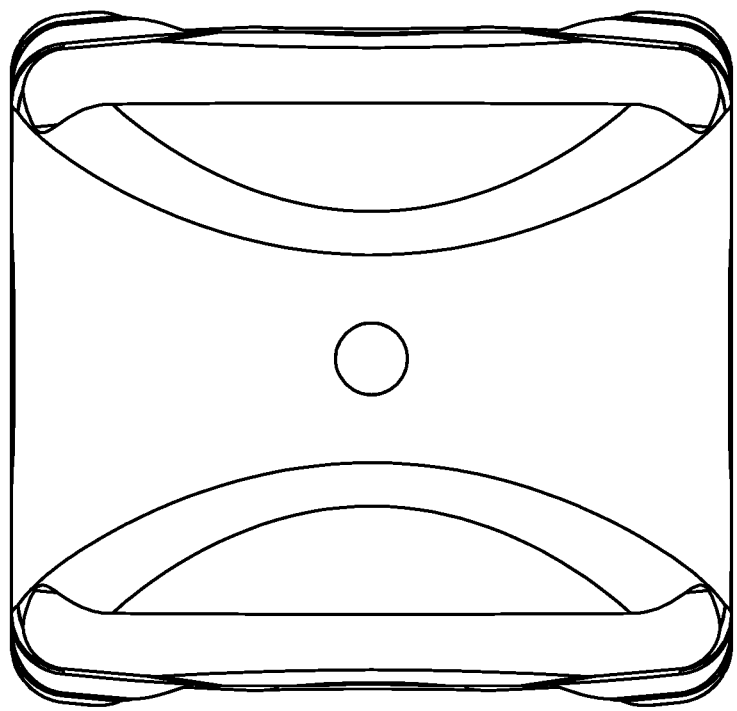
FIG. 7G illustrates the distal end of the intervertebral spacer 700 of FIG. 7A.
Figure 7H:
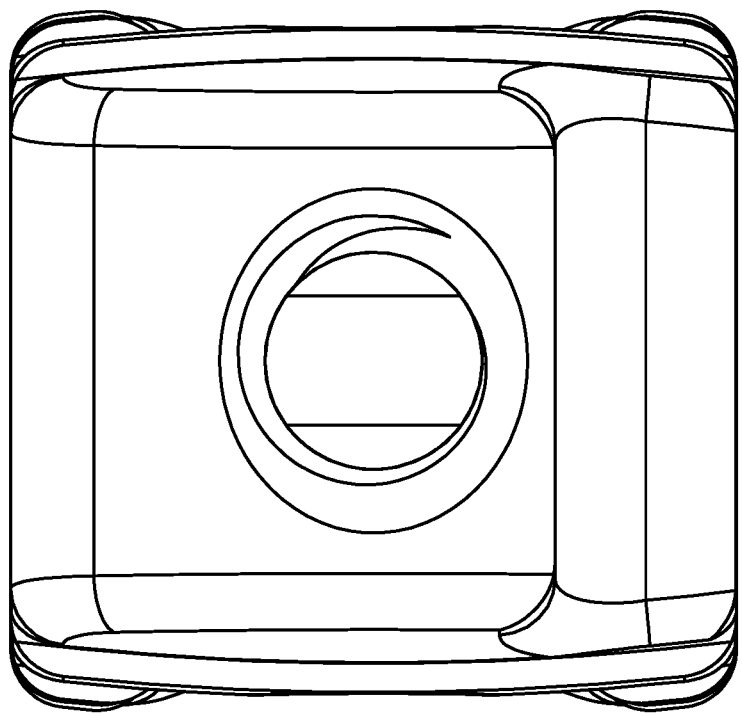
FIG. 7H illustrates the proximal end of the intervertebral spacer 700 of FIG. 7A.
Figure 8A:
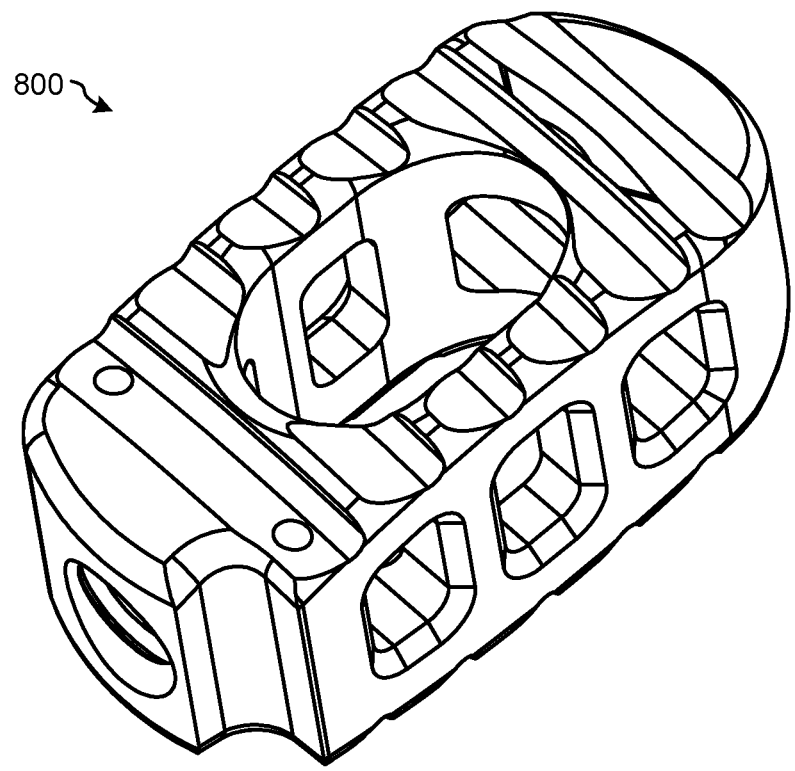
FIG. 8A is a perspective top view of a proximal end of an intervertebral spacer 800, according to an embodiment of the present disclosure.
Figure 8B:
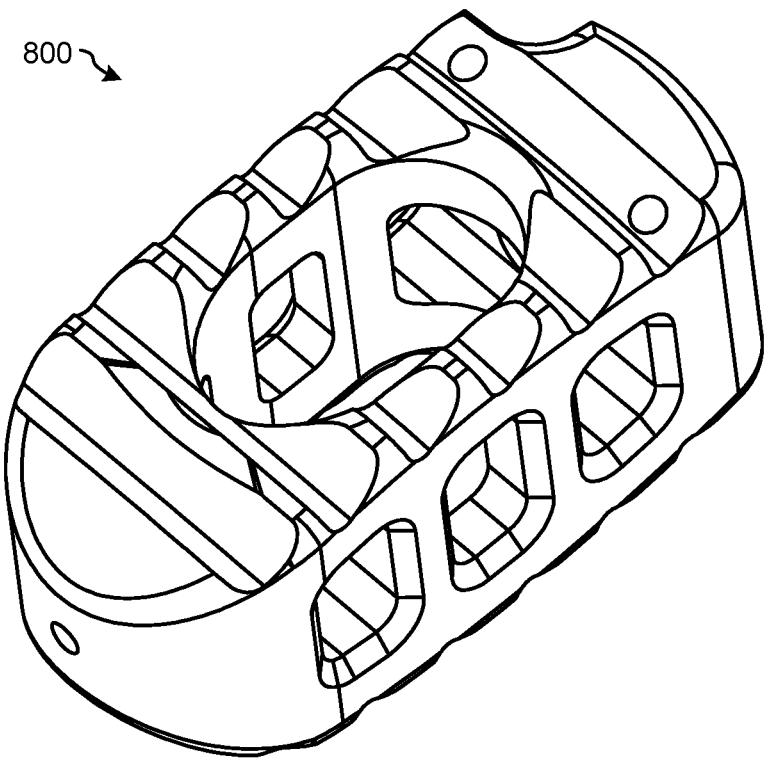
FIG. 8B is a perspective top view of a distal end of the intervertebral spacer 800 of FIG. 8A.
Figure 8C:
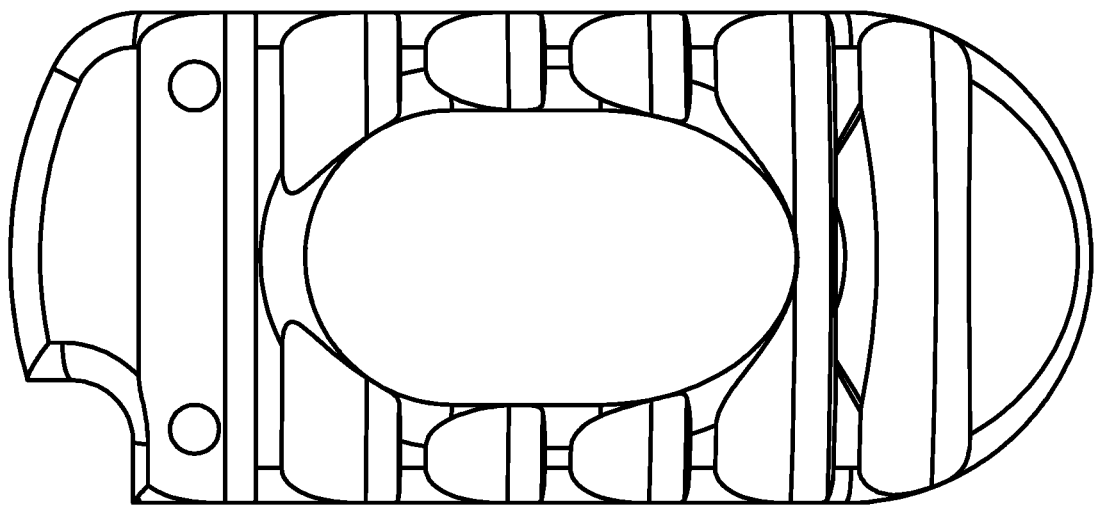
FIG. 8C is a top view of the intervertebral spacer 800 of FIG. 8A.
Figure 8D:
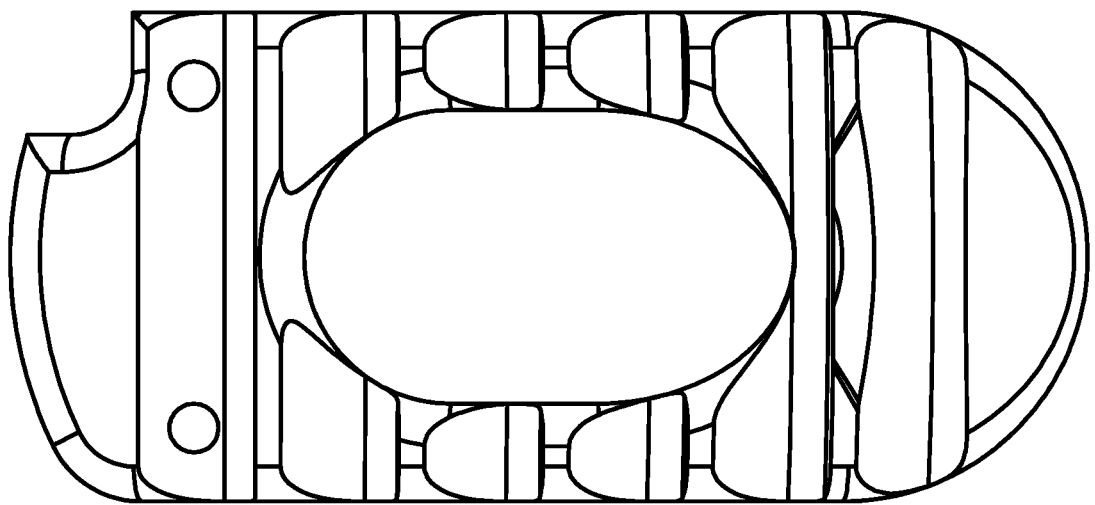
FIG. 8D is a bottom view of the intervertebral spacer 800 of FIG. 8A.
Figure 8E:
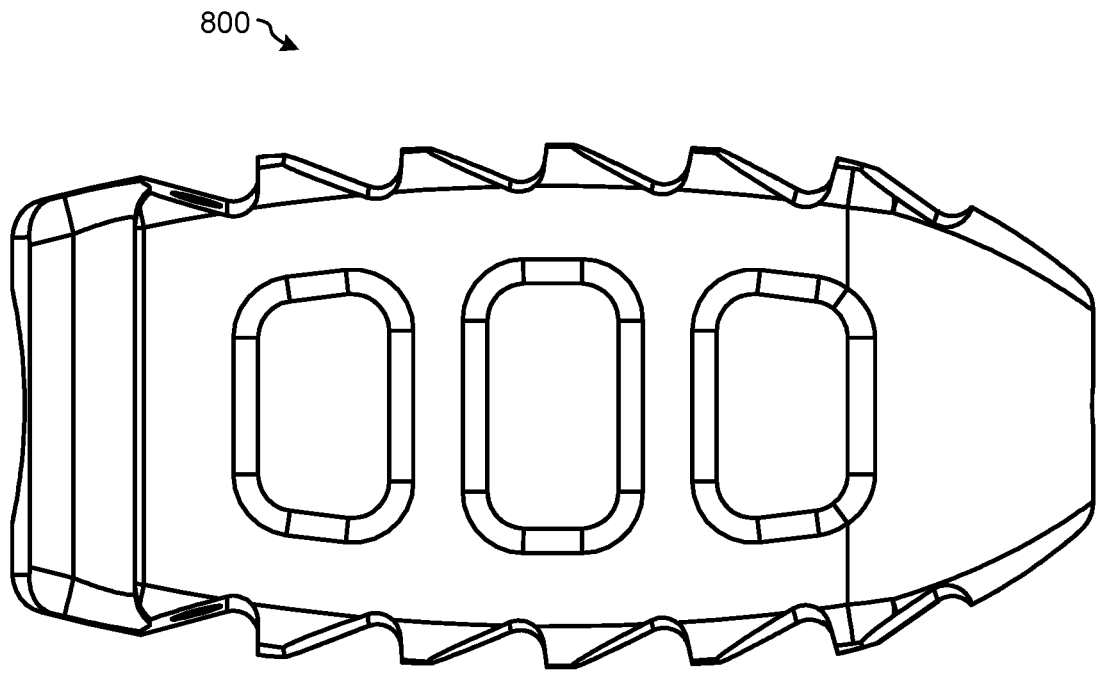
FIG. 8E illustrates a first side of the intervertebral spacer 800 of FIG. 8A.
Figure 8F:
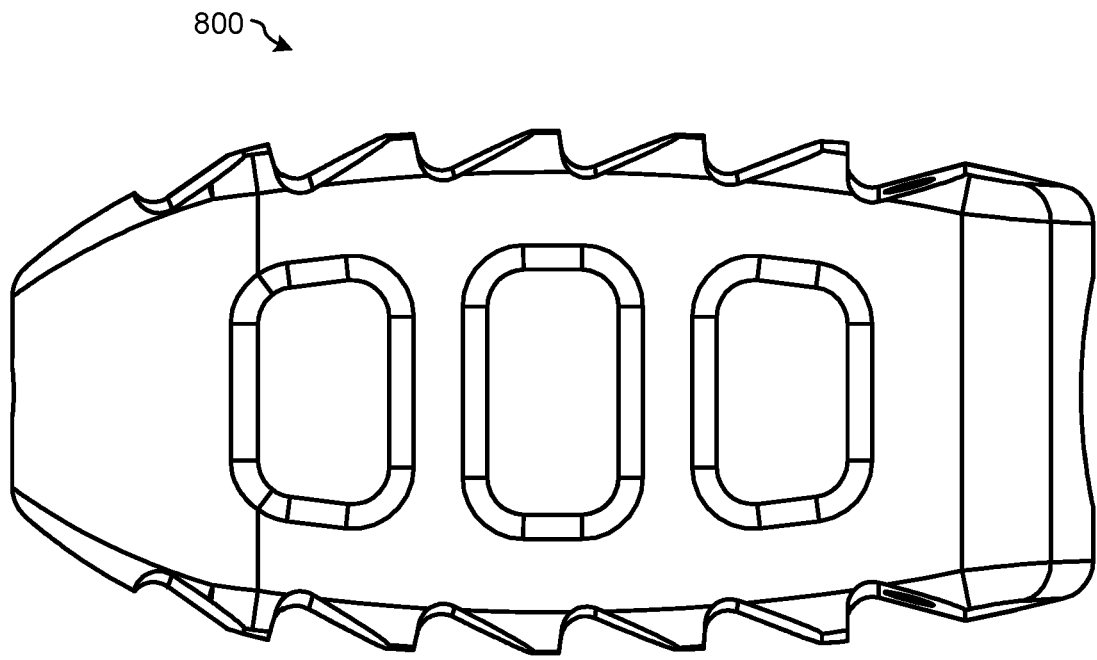
FIG. 8F illustrates a second side of the intervertebral spacer 800 of FIG. 8A.
Figure 8G:
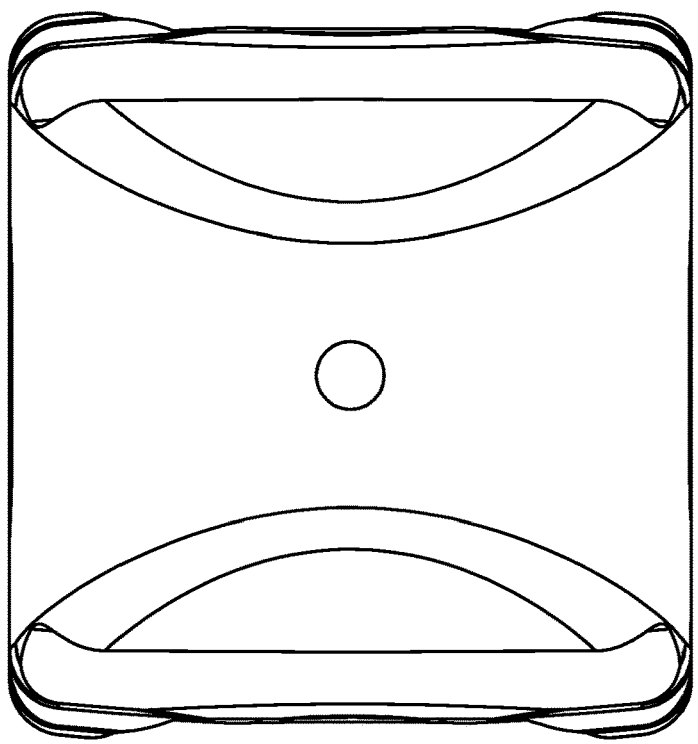
FIG. 8G illustrates the distal end of the intervertebral spacer 800 of FIG. 8A.
Figure 8H:
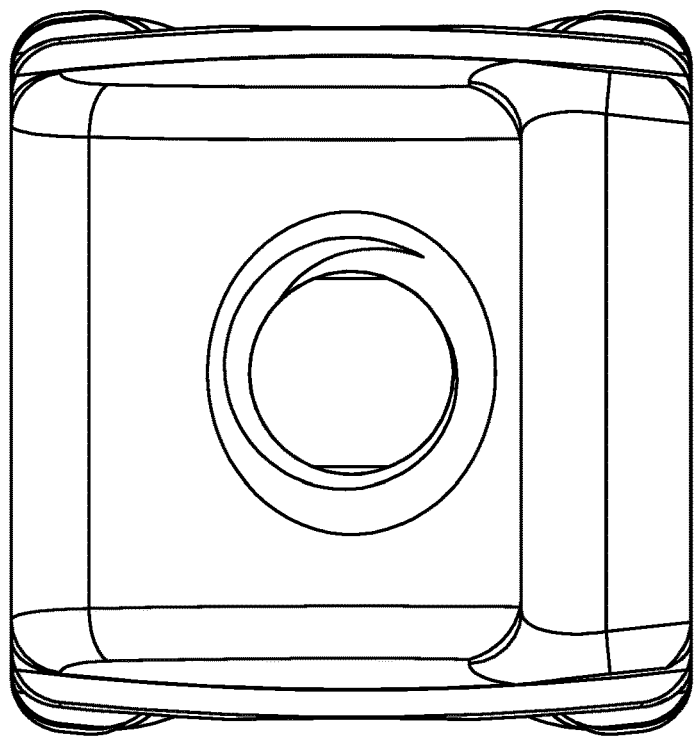
FIG. 8H illustrates the proximal end of the intervertebral spacer 800 of FIG. 8A.
Figure 9A:
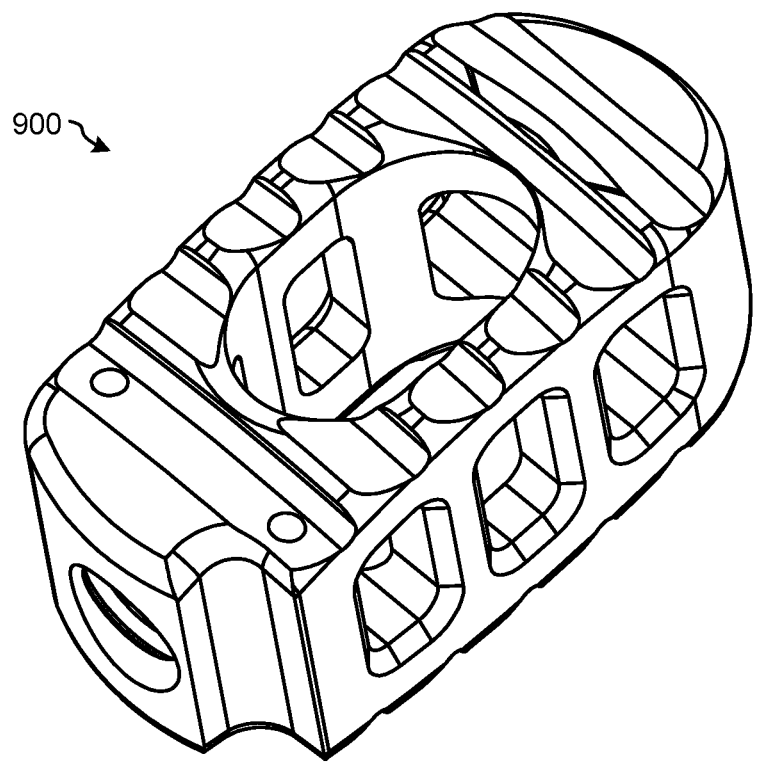
FIG. 9A is a perspective top view of a proximal end of an intervertebral spacer 900, according to an embodiment of the present disclosure.
Figure 9B:
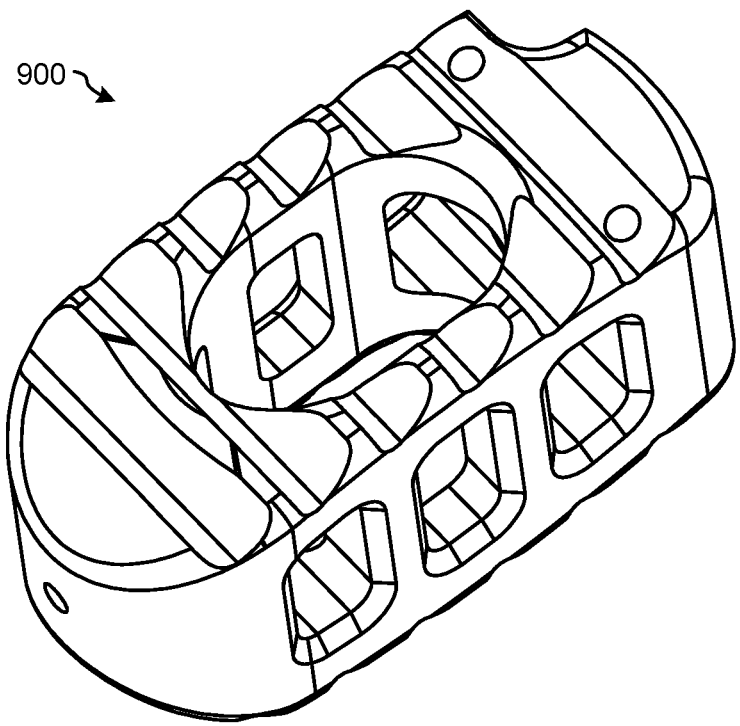
FIG. 9B is a perspective top view of a distal end of the intervertebral spacer 900 of FIG. 9A.
Figure 9C:
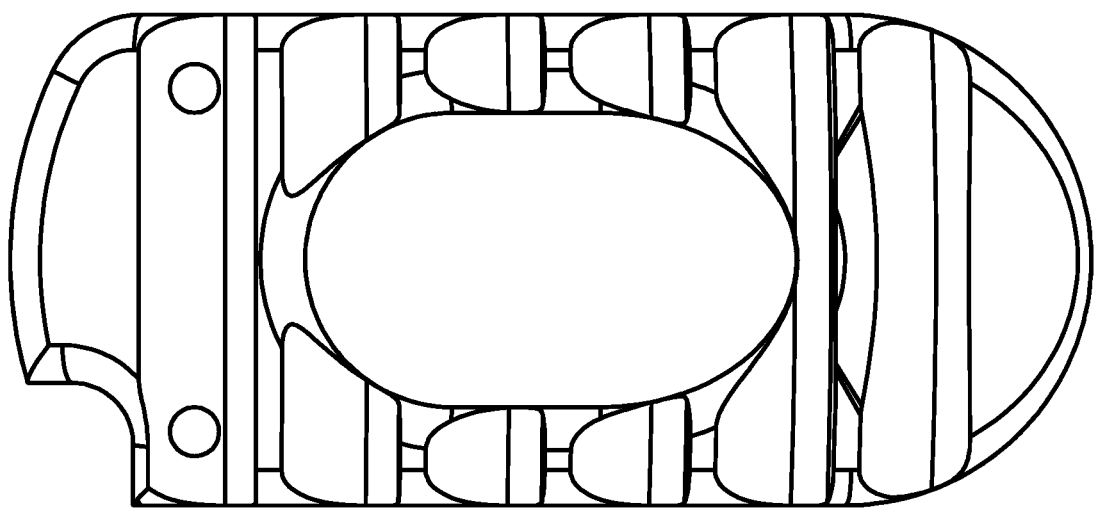
FIG. 9C is a top view of the intervertebral spacer 900 of FIG. 9A.
Figure 9D:
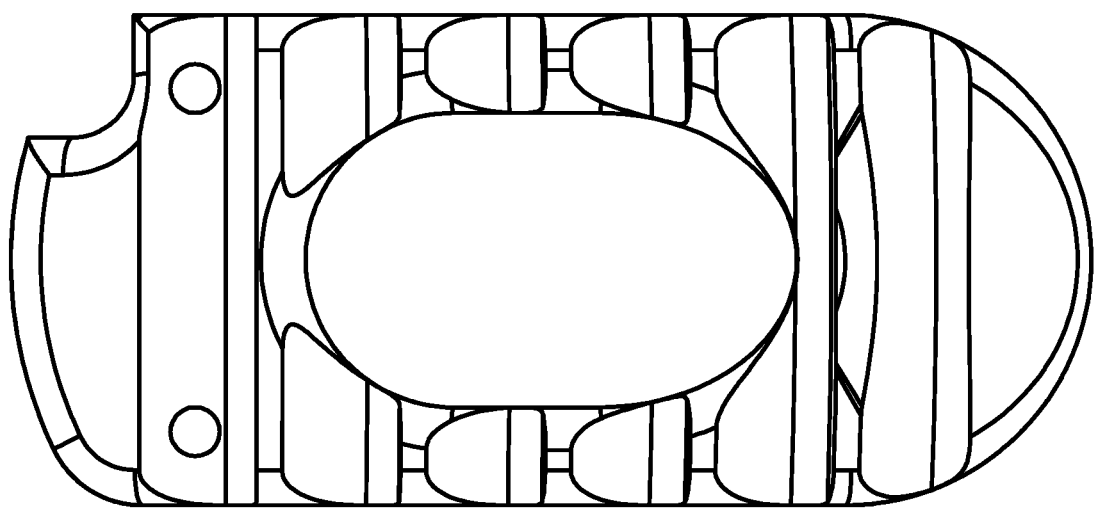
FIG. 9D is a bottom view of the intervertebral spacer 900 of FIG. 9A.
Figure 9E:
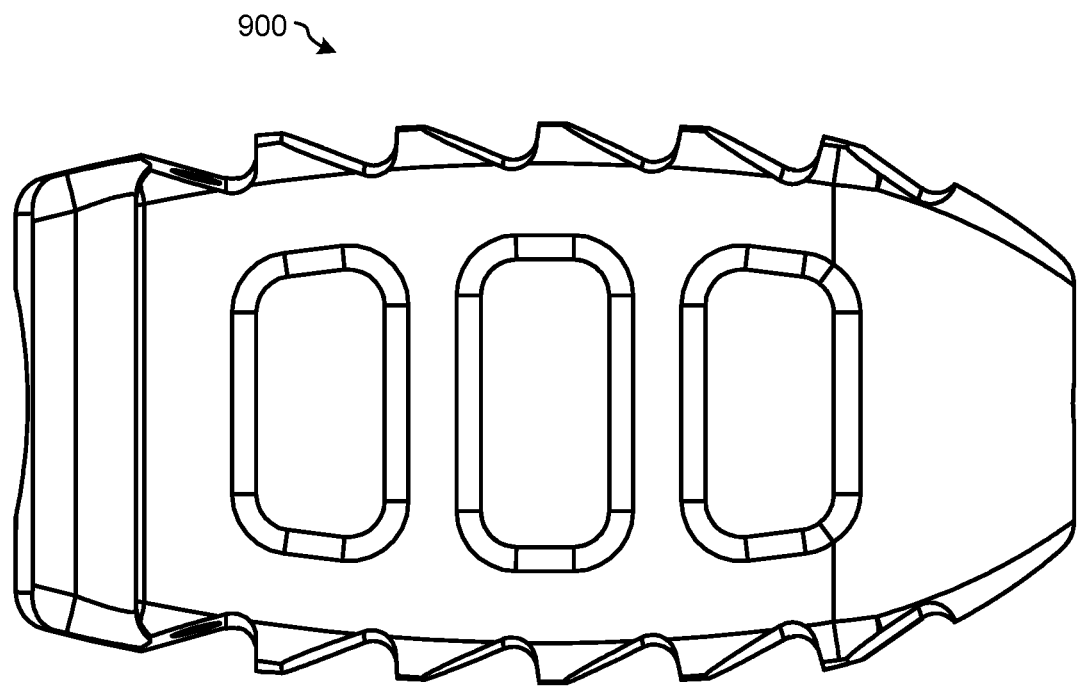
FIG. 9E illustrates a first side of the intervertebral spacer 900 of FIG. 9A.
Figure 9F:
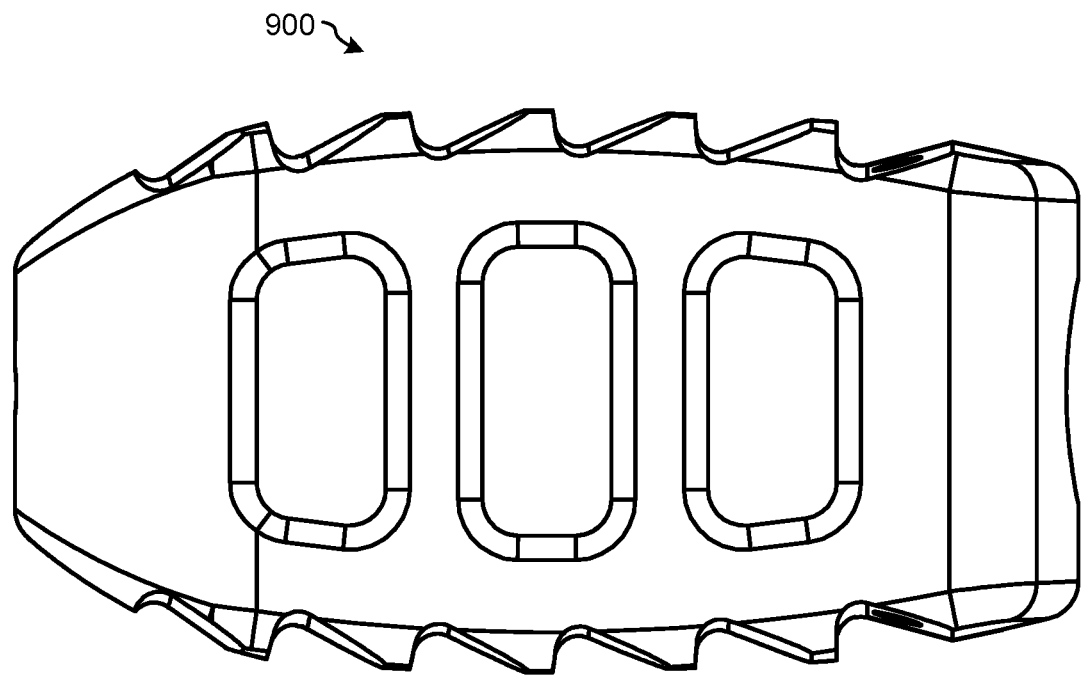
FIG. 9F illustrates a second side of the intervertebral spacer 900 of FIG. 9A.
Figure 9G:
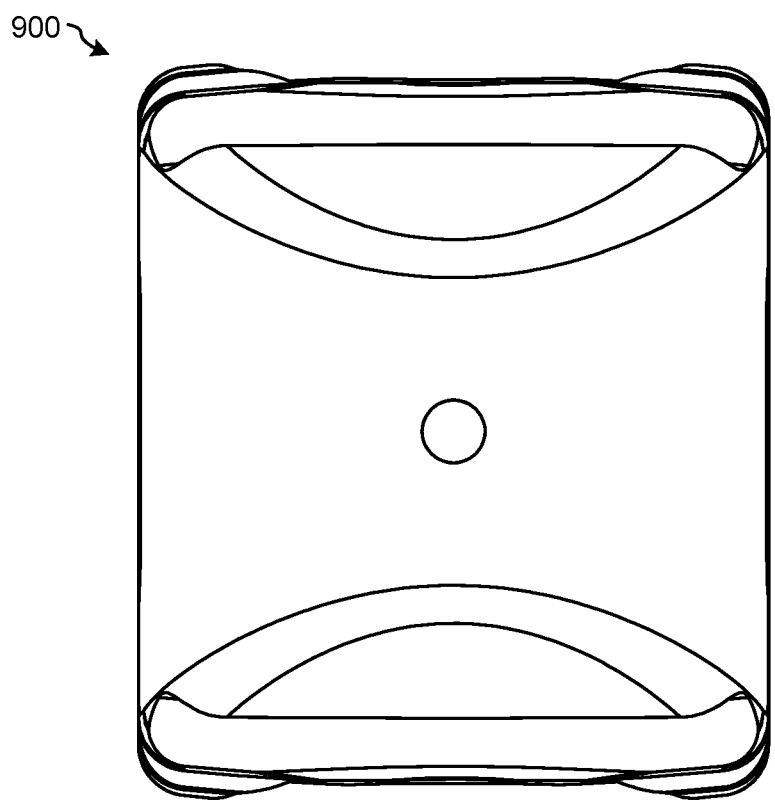
FIG. 9G illustrates the distal end of the intervertebral spacer 900 of FIG. 9A.
Figure 9H:
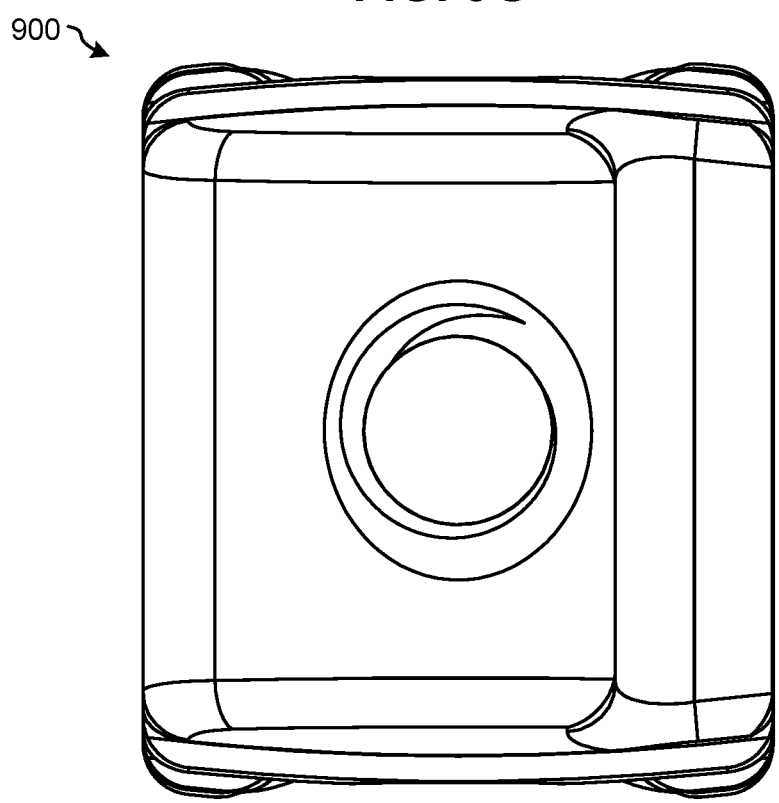
FIG. 9H illustrates the proximal end of the intervertebral spacer 900 of FIG. 9A.
Figure 10A:
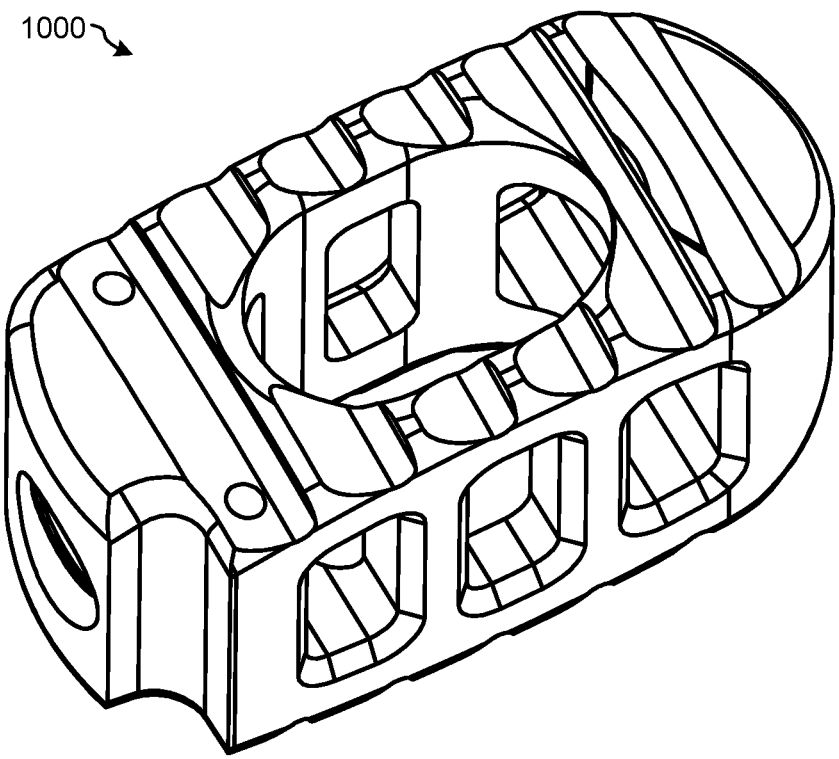
FIG. 10A is a perspective top view of a proximal end of an intervertebral spacer 1000, according to an embodiment of the present disclosure.
Figure 10B:
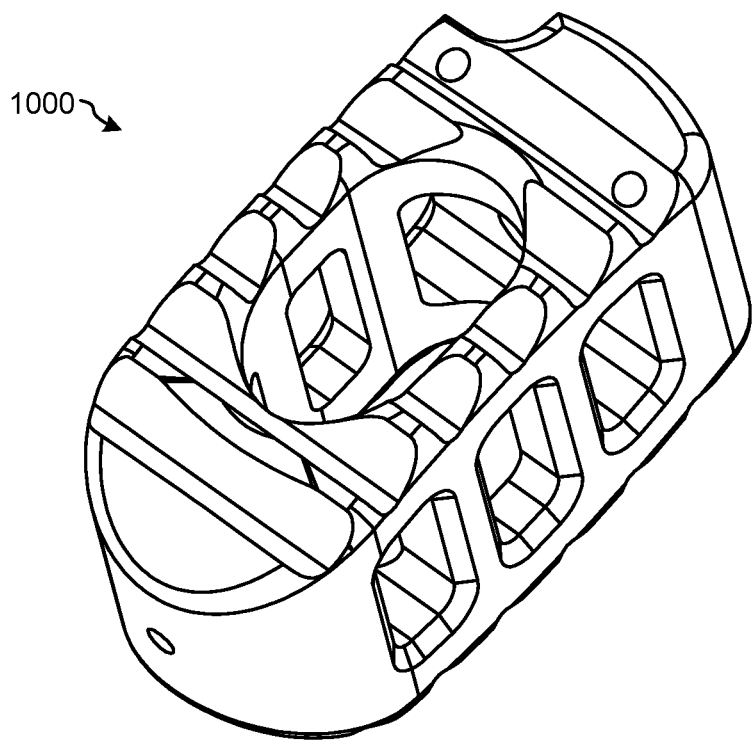
FIG. 10B is a perspective top view of a distal end of the intervertebral spacer 1000 of FIG. 10A.
Figure 10C:
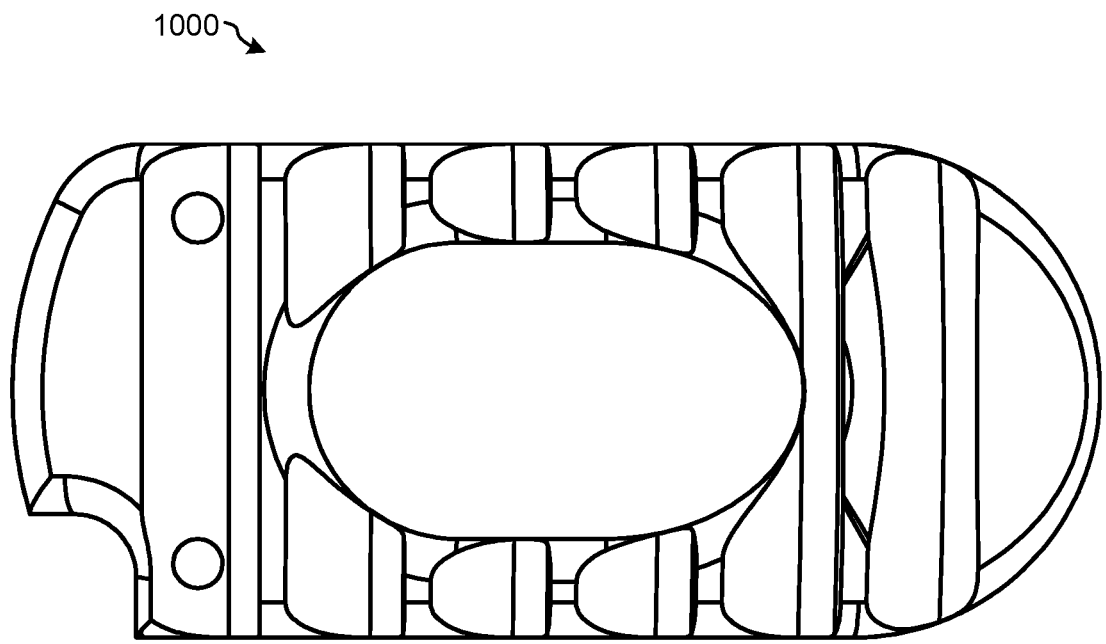
FIG. 10C is a top view of the intervertebral spacer 1000 of FIG. 10A.
Figure 10D:
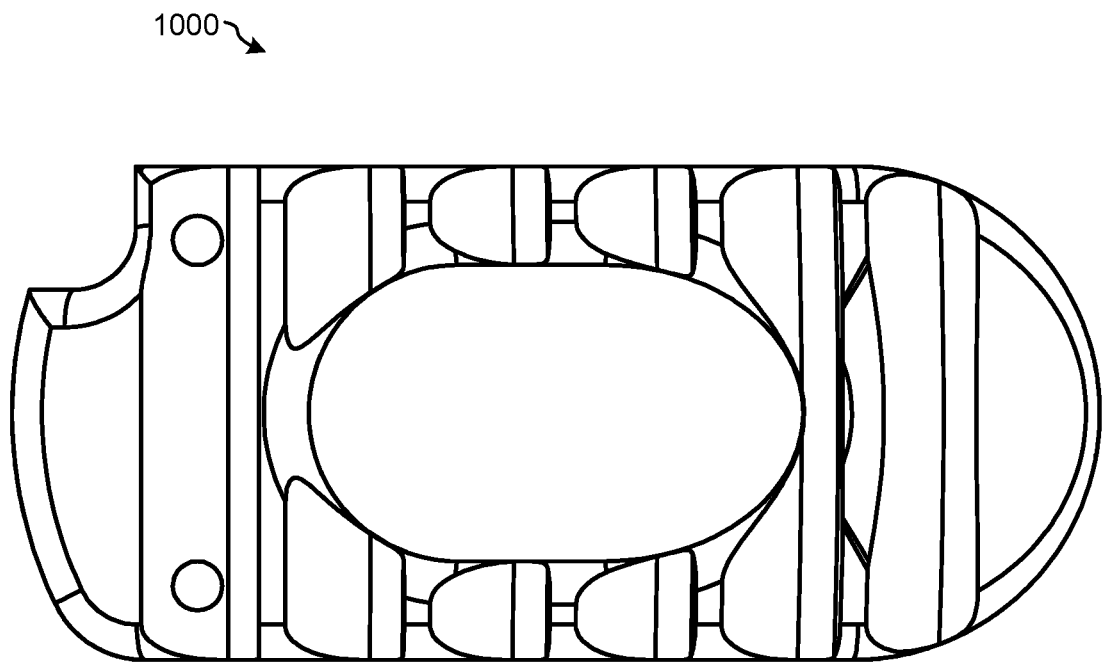
FIG. 10D is a bottom view of the intervertebral spacer 1000 of FIG. 10A.
Figure 10E:
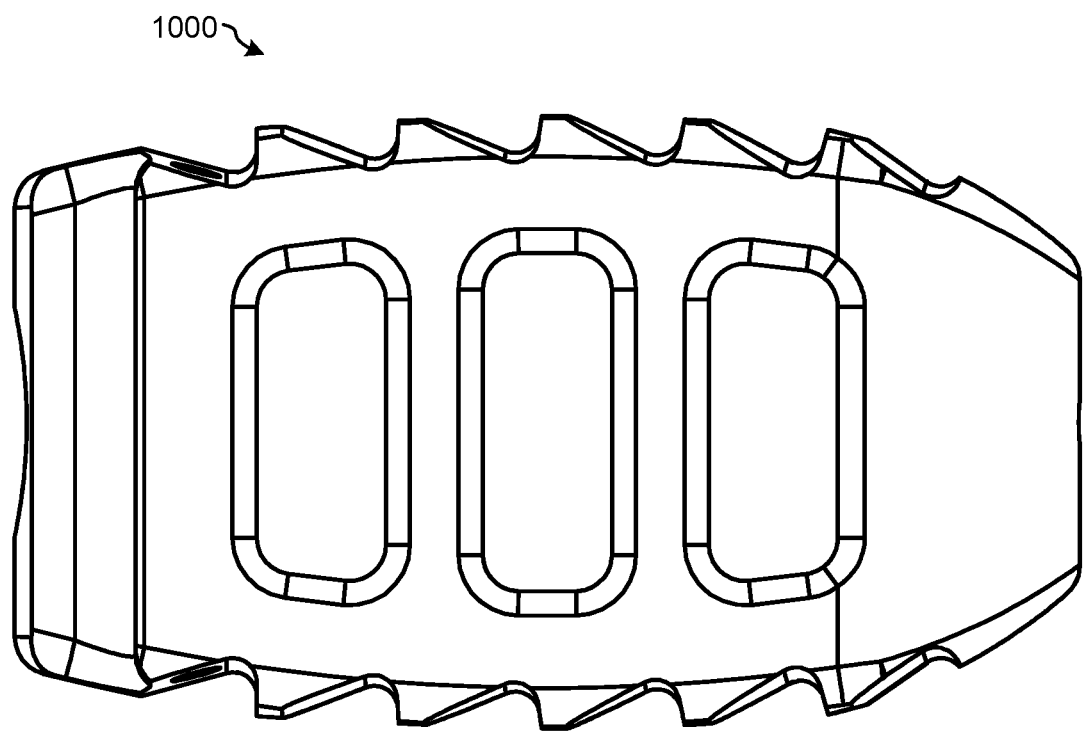
FIG. 10E illustrates a first side of the intervertebral spacer 1000 of FIG. 10A.
Figure 10F:
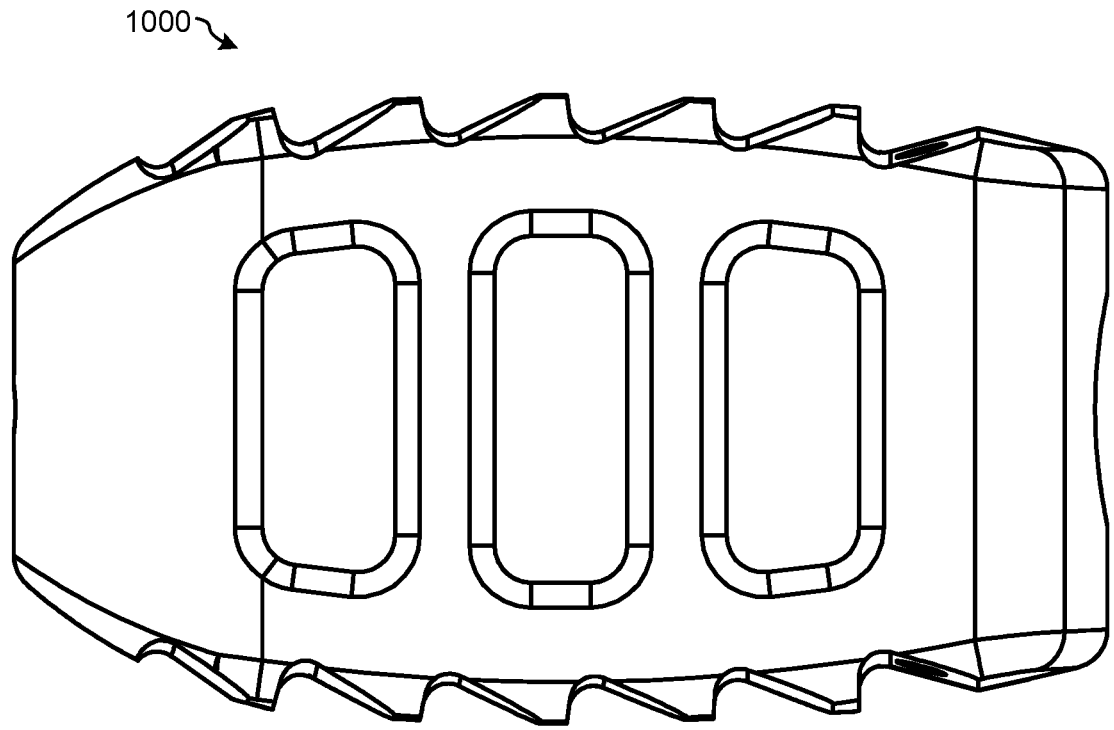
FIG. 10F illustrates a second side of the intervertebral spacer 1000 of FIG. 10A.
Figure 10G:
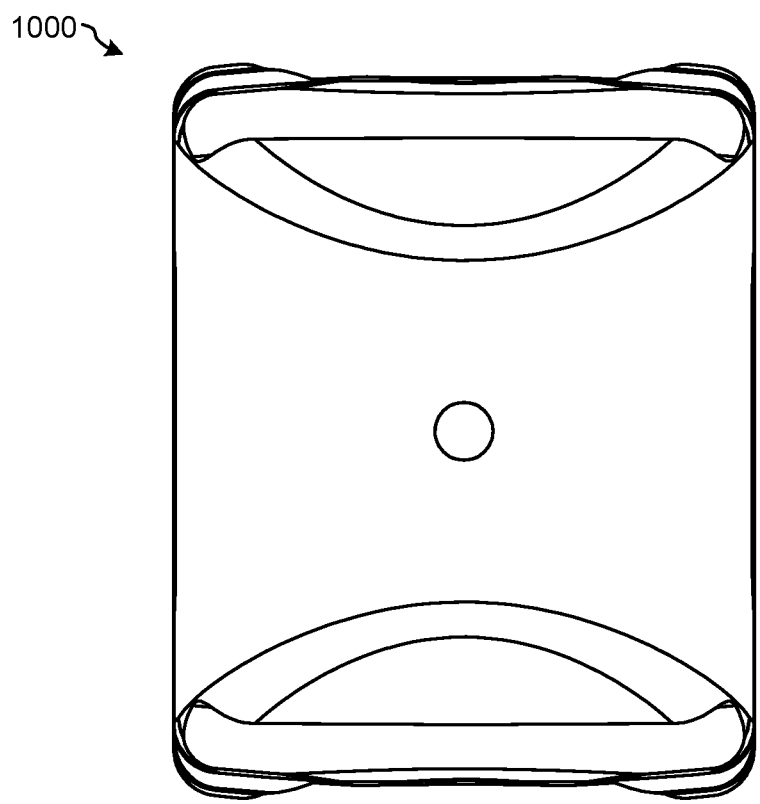
FIG. 10G illustrates the distal end of the intervertebral spacer 1000 of FIG. 10A.
Figure 10H:
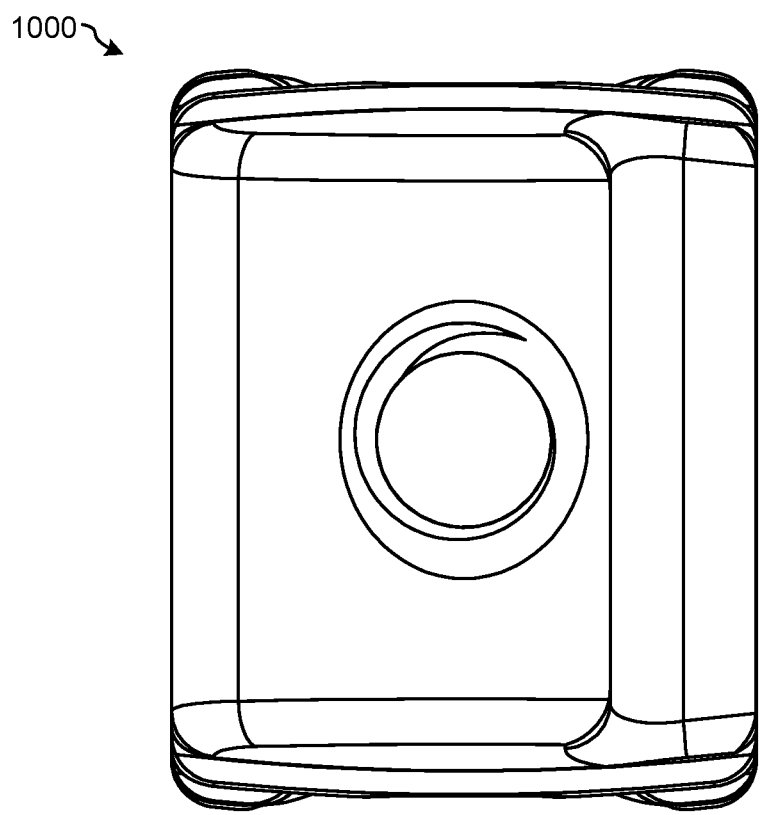
FIG. 10H illustrates the proximal end of the intervertebral spacer 1000 of FIG. 10A.
Figure 11A:
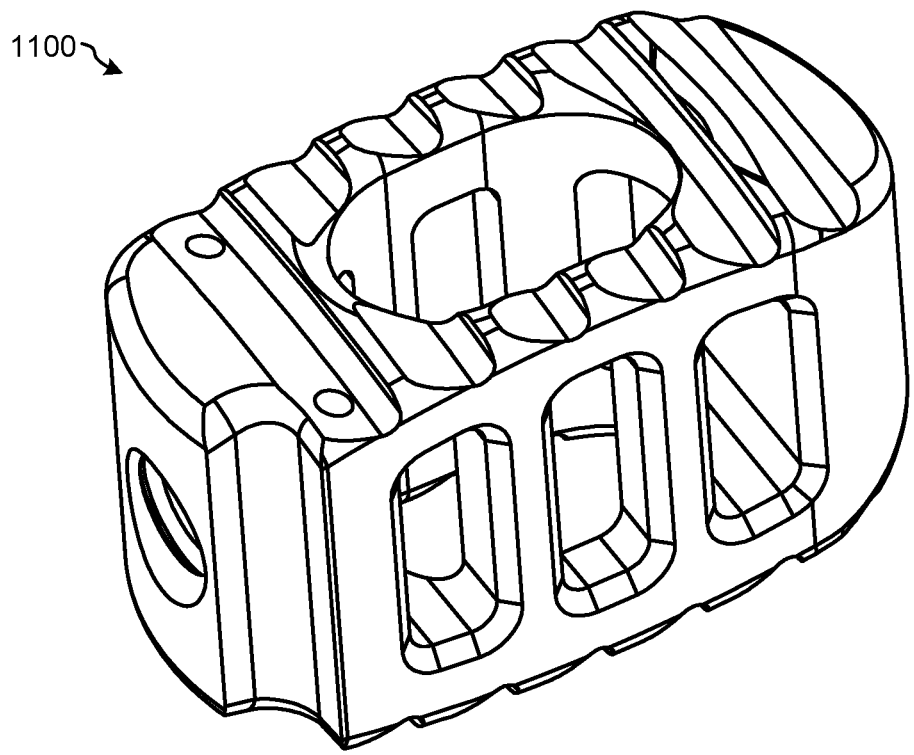
FIG. 11A is a perspective top view of a proximal end of an intervertebral spacer 1100, according to an embodiment of the present disclosure.
Figure 11B:
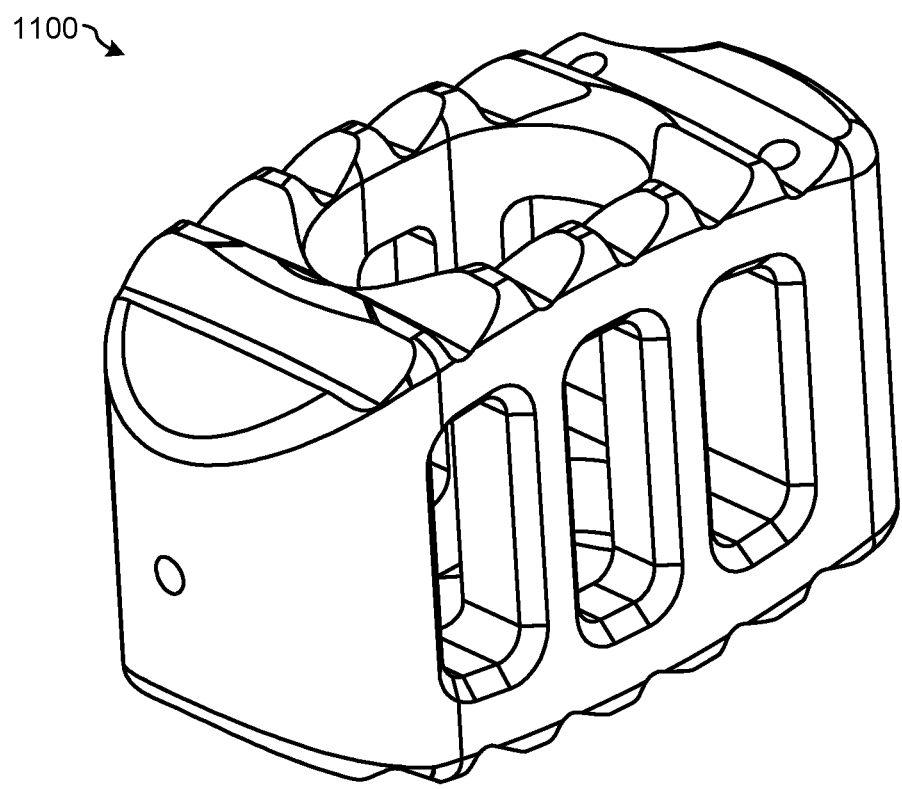
FIG. 11B is a perspective top view of a distal end of the intervertebral spacer 1100 of FIG. 11A.
Figure 11C:
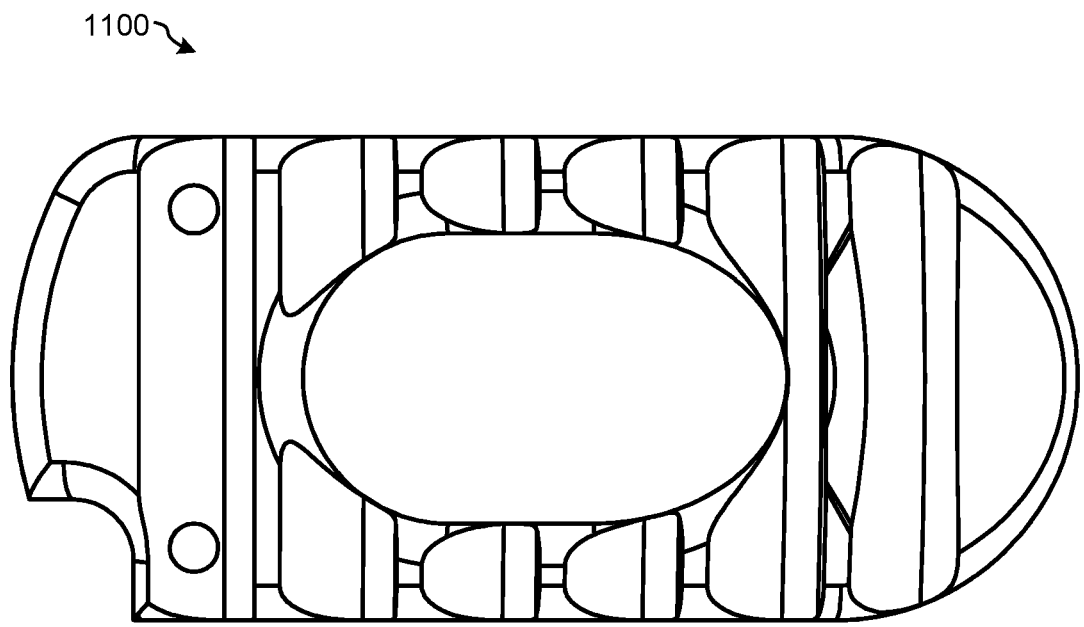
FIG. 11C is a top view of the intervertebral spacer 1100 of FIG. 11A.
Figure 11D:
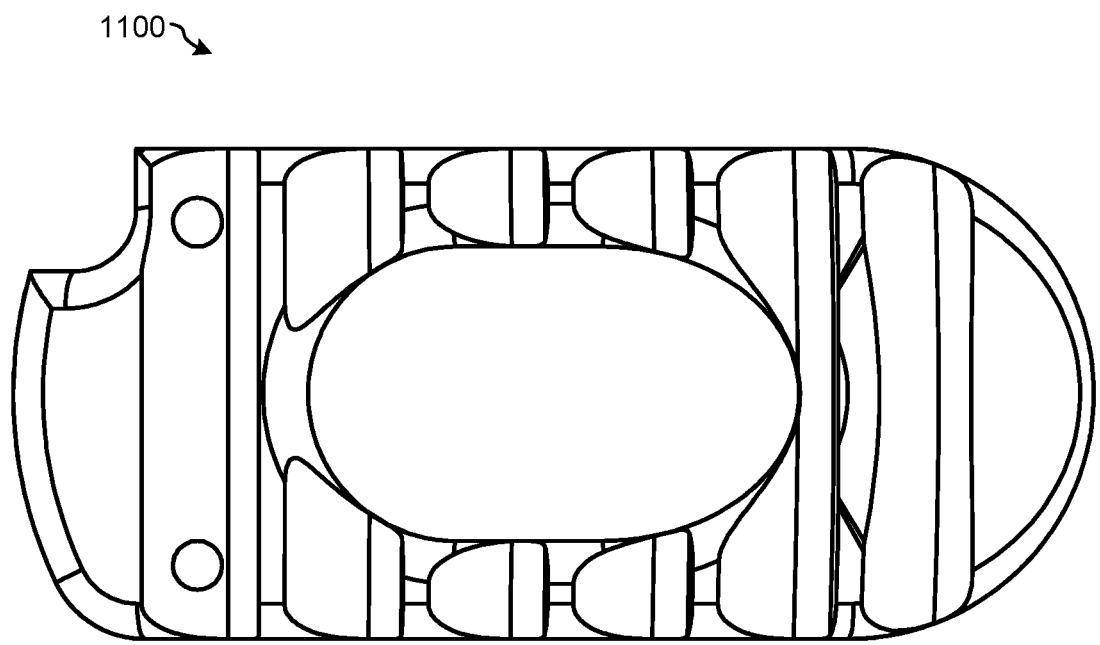
FIG. 11D is a bottom view of the intervertebral spacer 1100 of FIG. 11A.
Figure 11E:
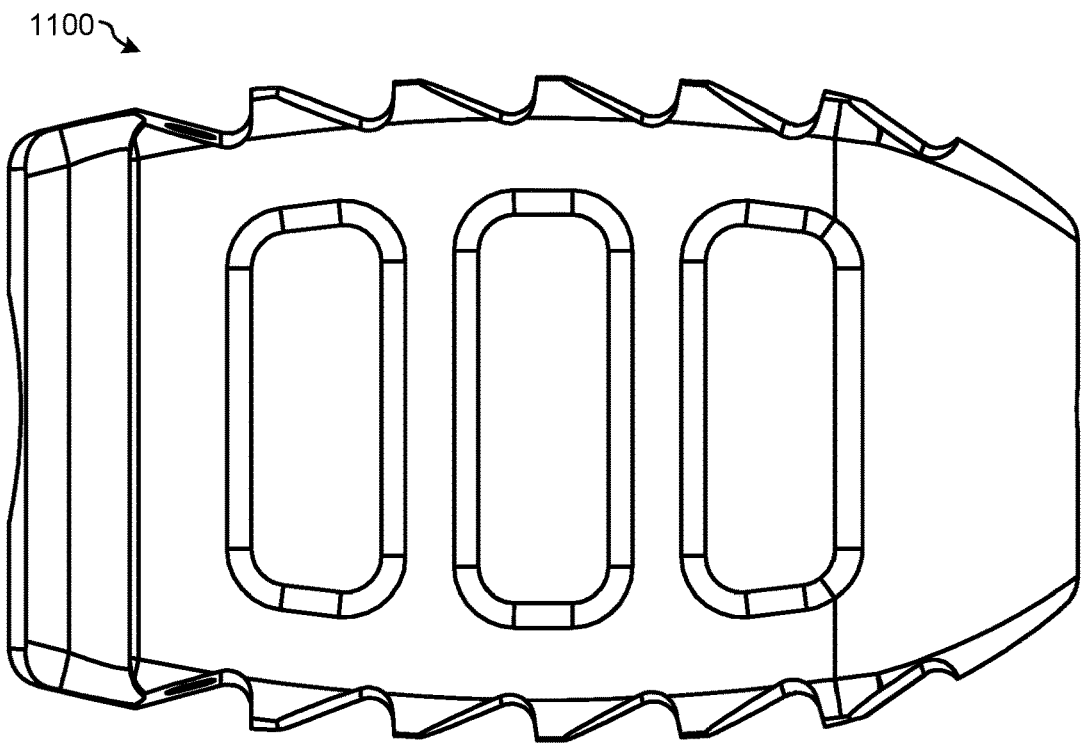
FIG. 11E illustrates a first side of the intervertebral spacer 1100 of FIG. 11A.
Figure 11F:
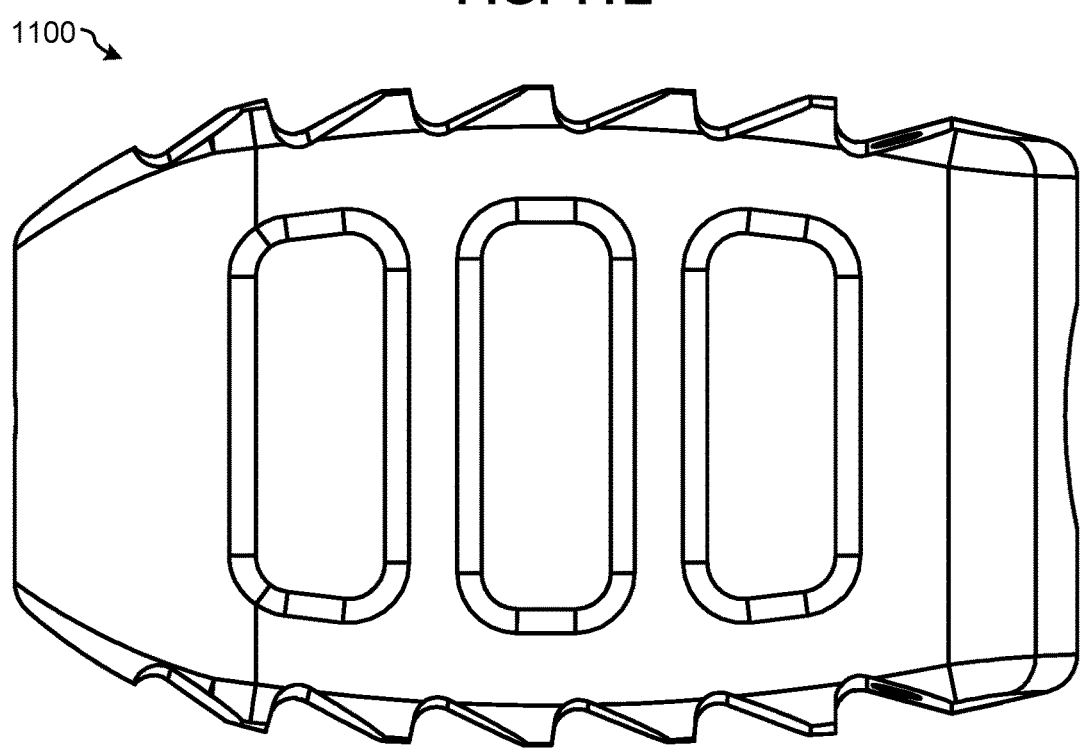
FIG. 11F illustrates a second side of the intervertebral spacer 1100 of FIG. 11A.
Figure 11G:
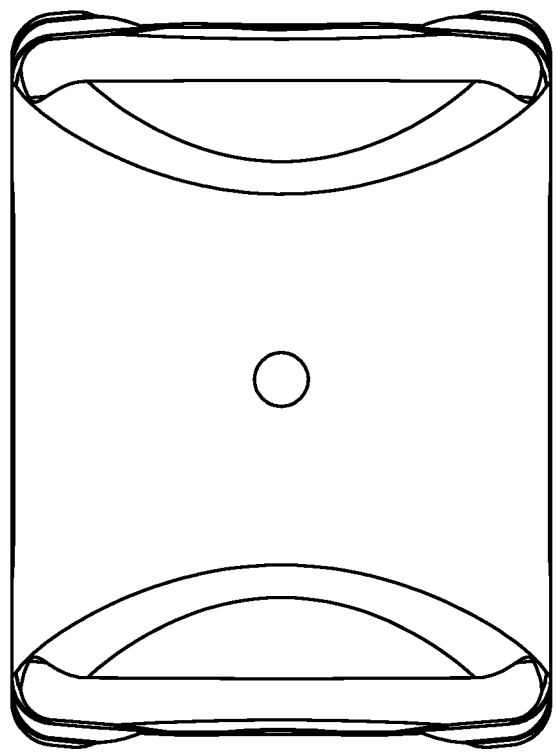
FIG. 11G illustrates the distal end of the intervertebral spacer 1100 of FIG. 11A.
Figure 11H:
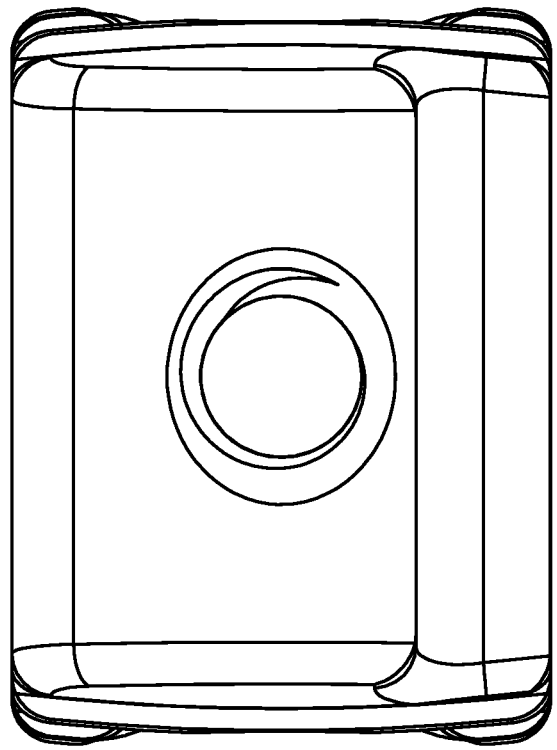
FIG. 11H illustrates the proximal end of the intervertebral spacer 1100 of FIG. 11A.
Figure 12A:
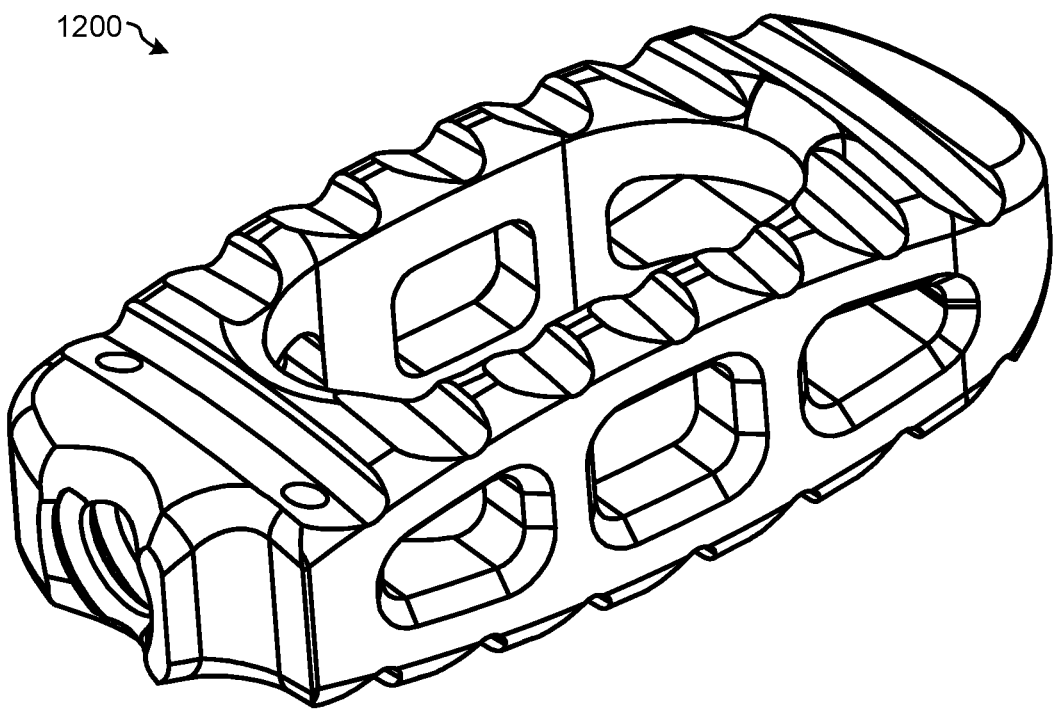
FIG. 12A is a perspective top view of a proximal end of an intervertebral spacer 1200, according to an embodiment of the present disclosure.
Figure 12B:
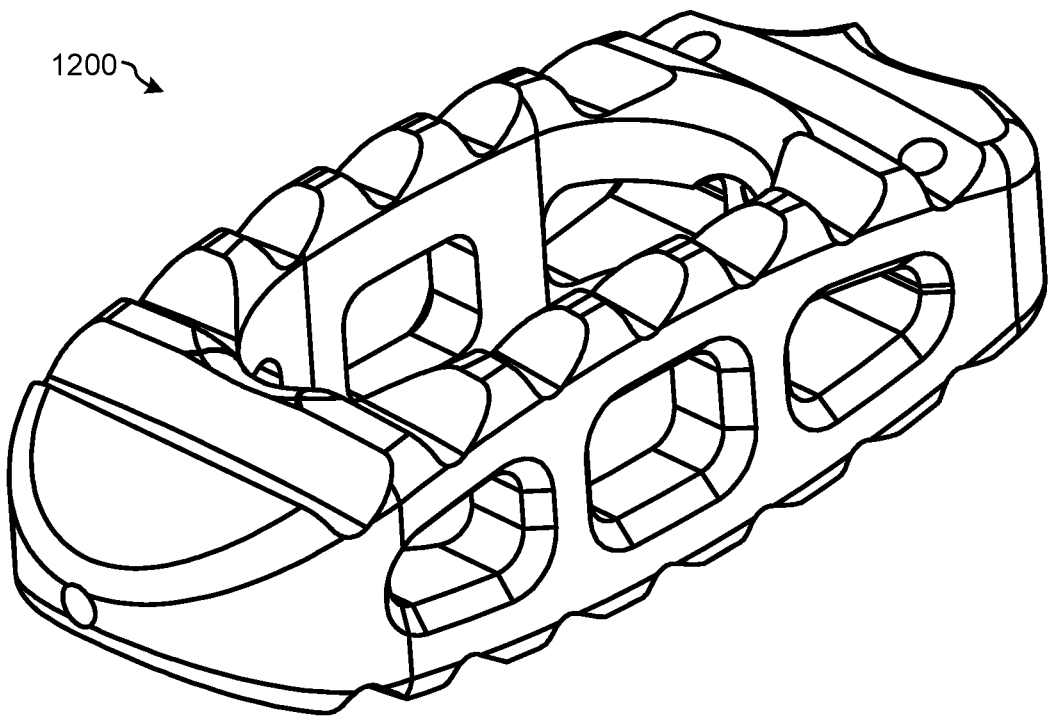
FIG. 12B is a perspective top view of a distal end of the intervertebral spacer 1200 of FIG. 12A.
Figure 12C:
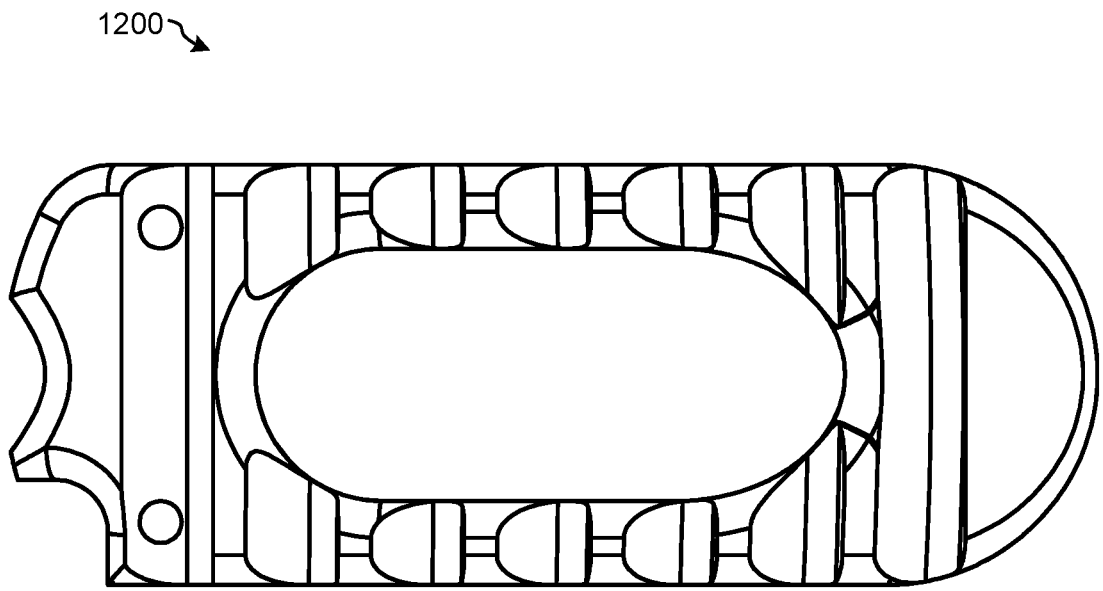
FIG. 12C is a top view of the intervertebral spacer 1200 of FIG. 12A.
Figure 12D:
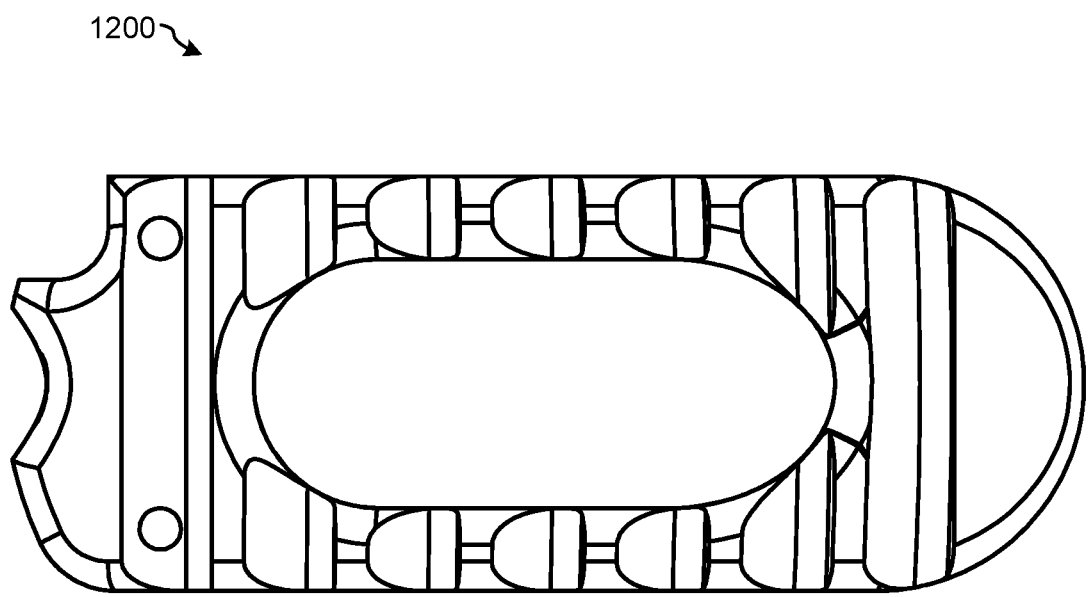
FIG. 12D is a bottom view of the intervertebral spacer 1200 of FIG. 12A.
Figure 12E:
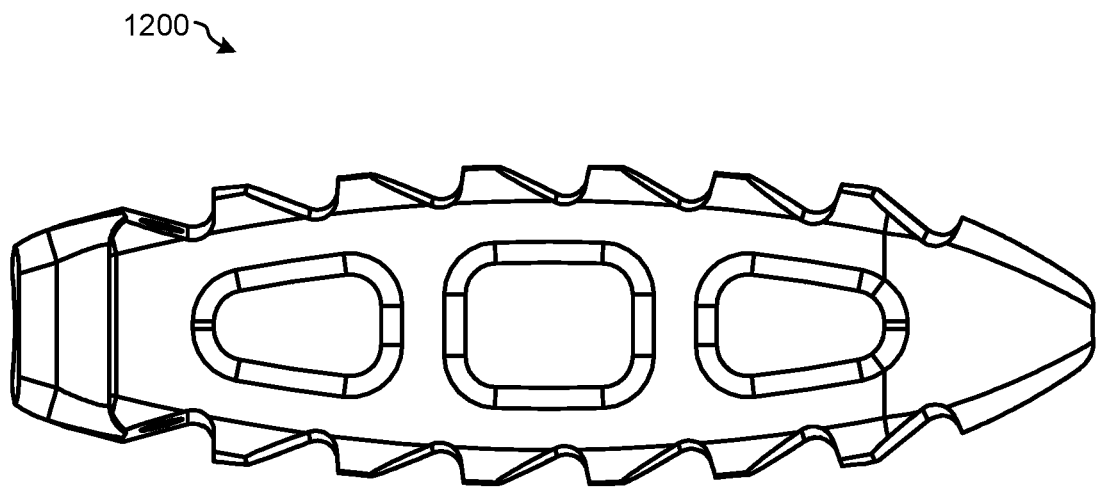
FIG. 12E illustrates a first side of the intervertebral spacer 1200 of FIG. 12A.
Figure 12F:
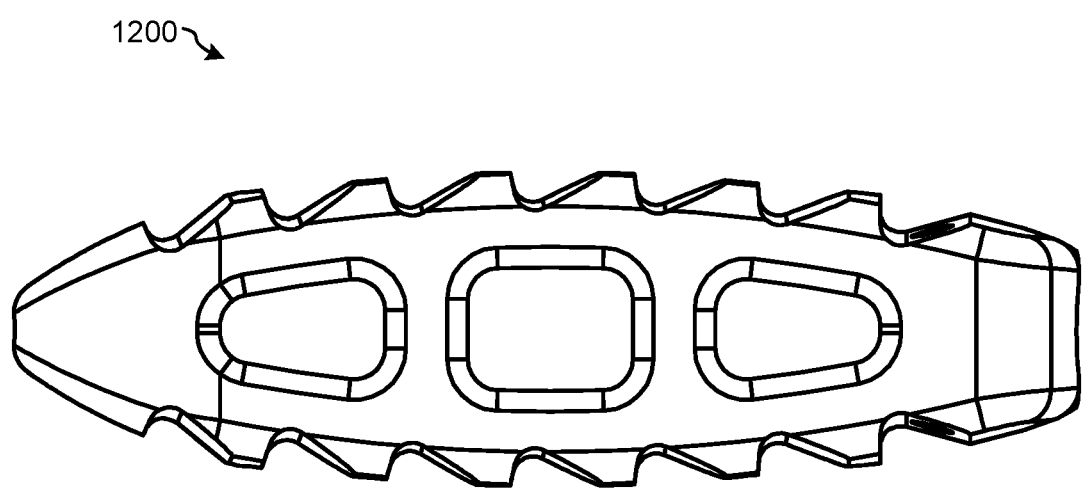
FIG. 12F illustrates a second side of the intervertebral spacer 1200 of FIG. 12A.
Figure 12G:
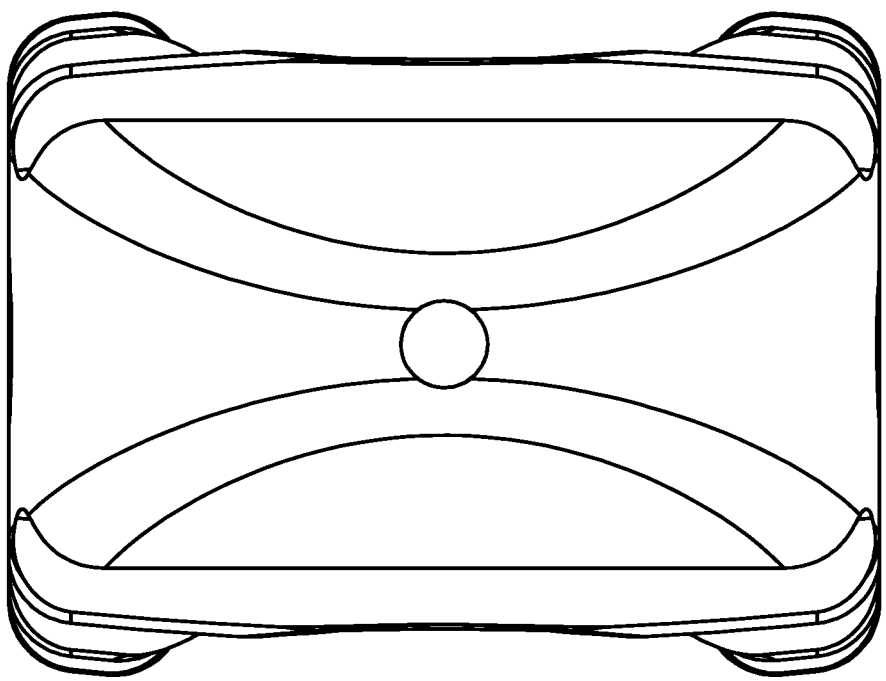
FIG. 12G illustrates the distal end of the intervertebral spacer 1200 of FIG. 12A.
Figure 12H:
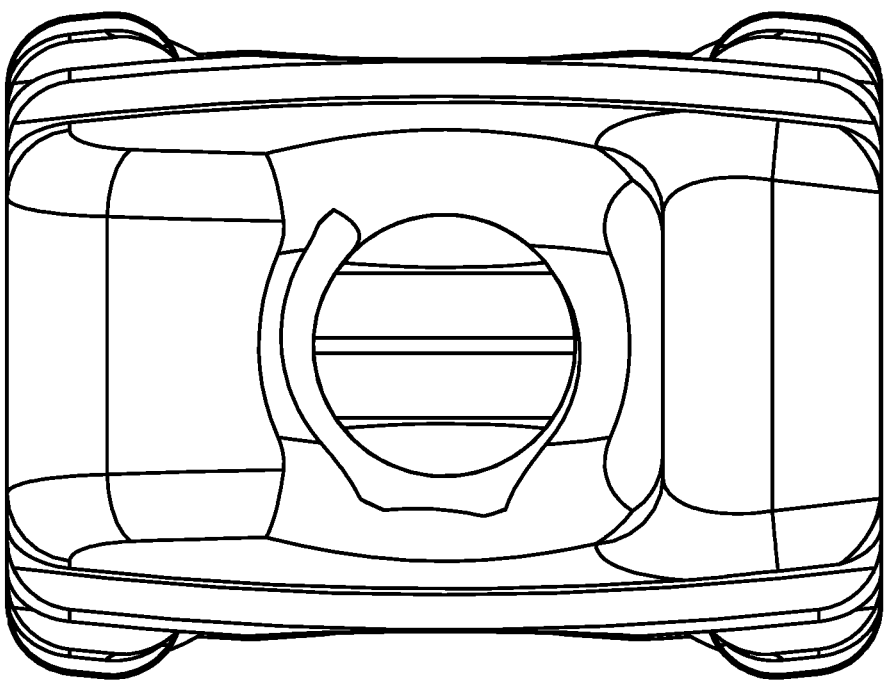
FIG. 12H illustrates the proximal end of the intervertebral spacer 1200 of FIG. 12A.
Figure 13A:
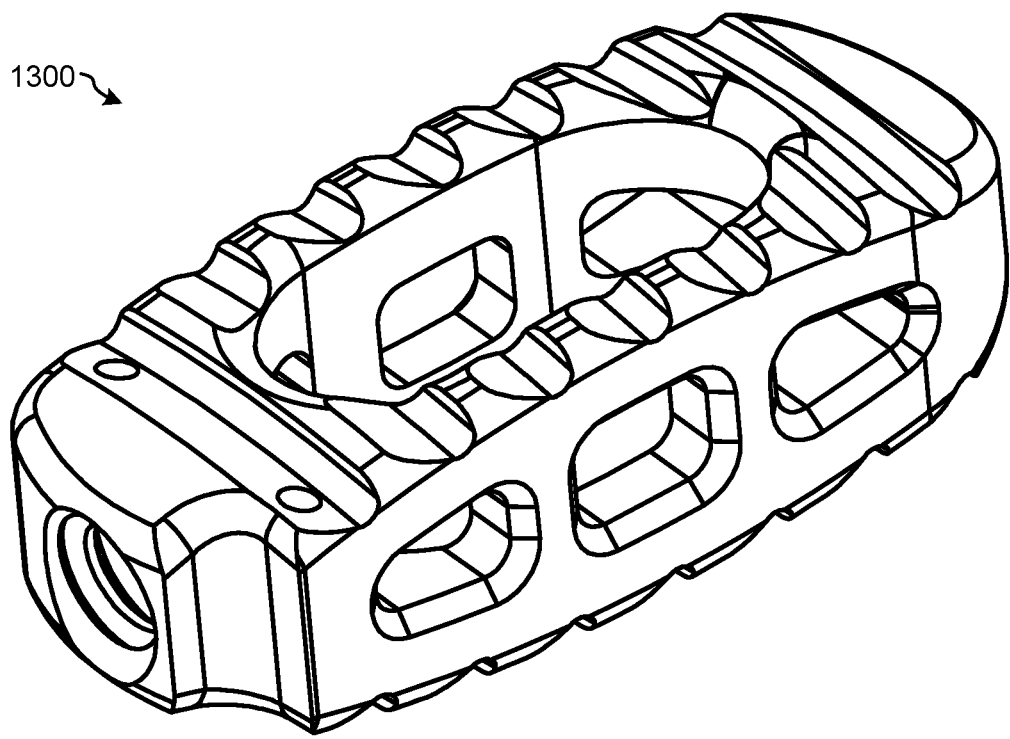
FIG. 13A is a perspective top view of a proximal end of an intervertebral spacer 1300, according to an embodiment of the present disclosure.
Figure 13B:
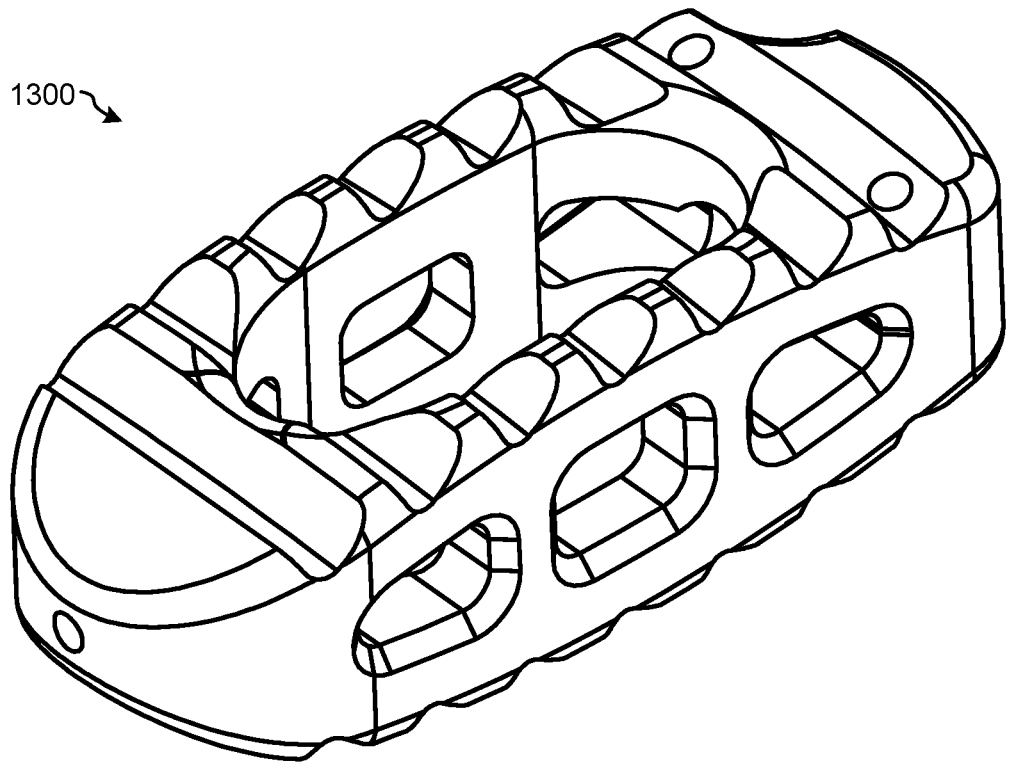
FIG. 13B is a perspective top view of a distal end of the intervertebral spacer 1300 of FIG. 13A.
Figure 13C:
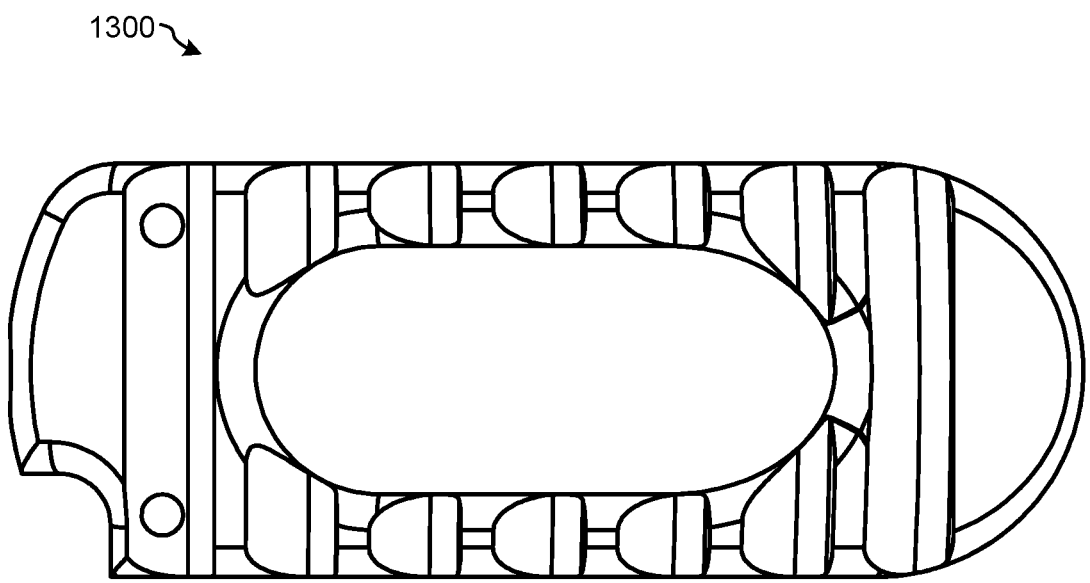
FIG. 13C is a top view of the intervertebral spacer 1300 of FIG. 13A.
Figure 13D:
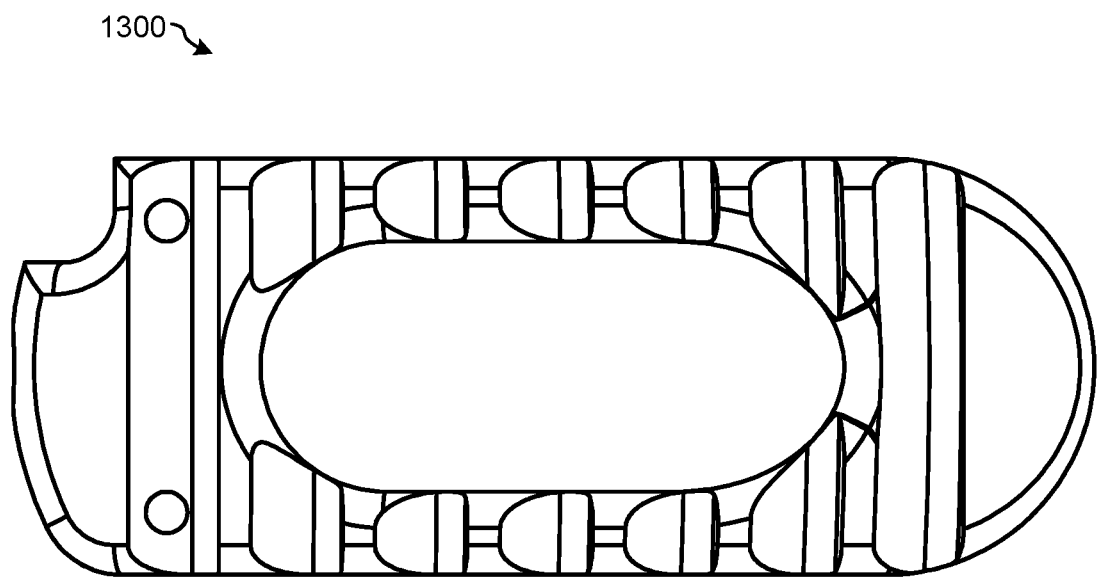
FIG. 13D is a bottom view of the intervertebral spacer 1300 of FIG. 13A.
Figure 13E:
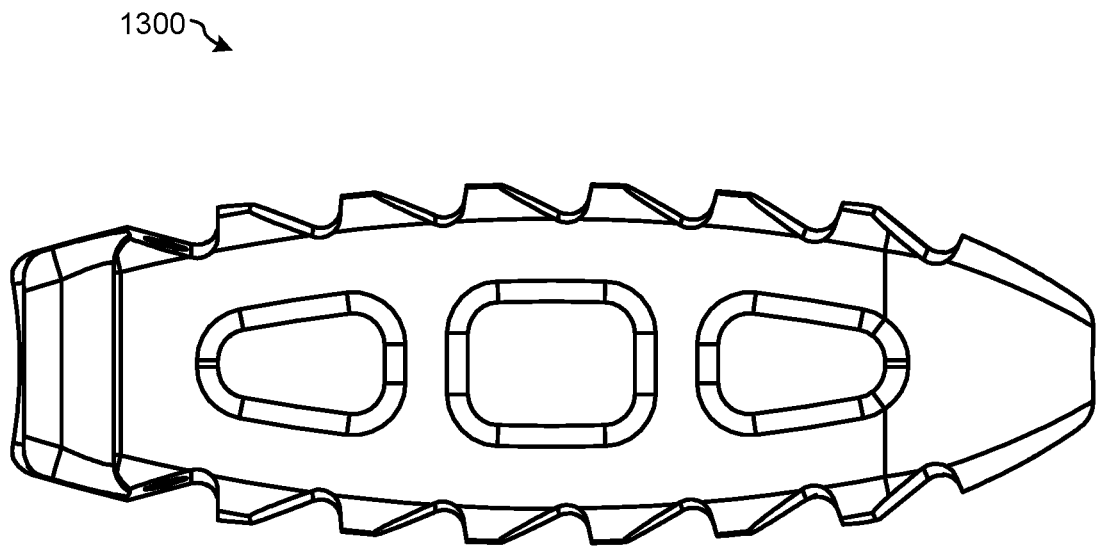
FIG. 13E illustrates a first side of the intervertebral spacer 1300 of FIG. 13A.
Figure 13F:
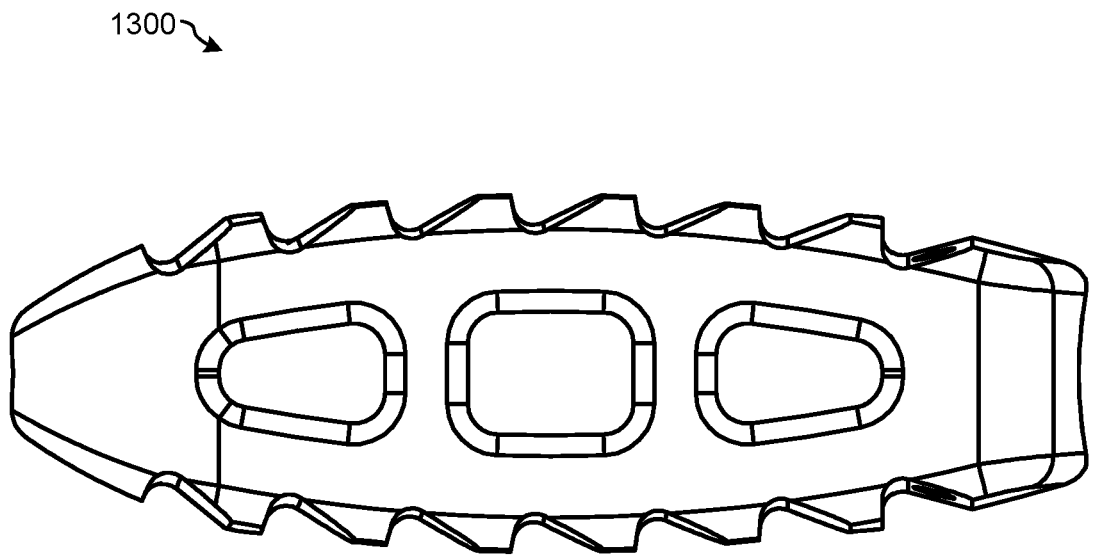
FIG. 13F illustrates a second side of the intervertebral spacer 1300 of FIG. 13A.
Figure 13G:
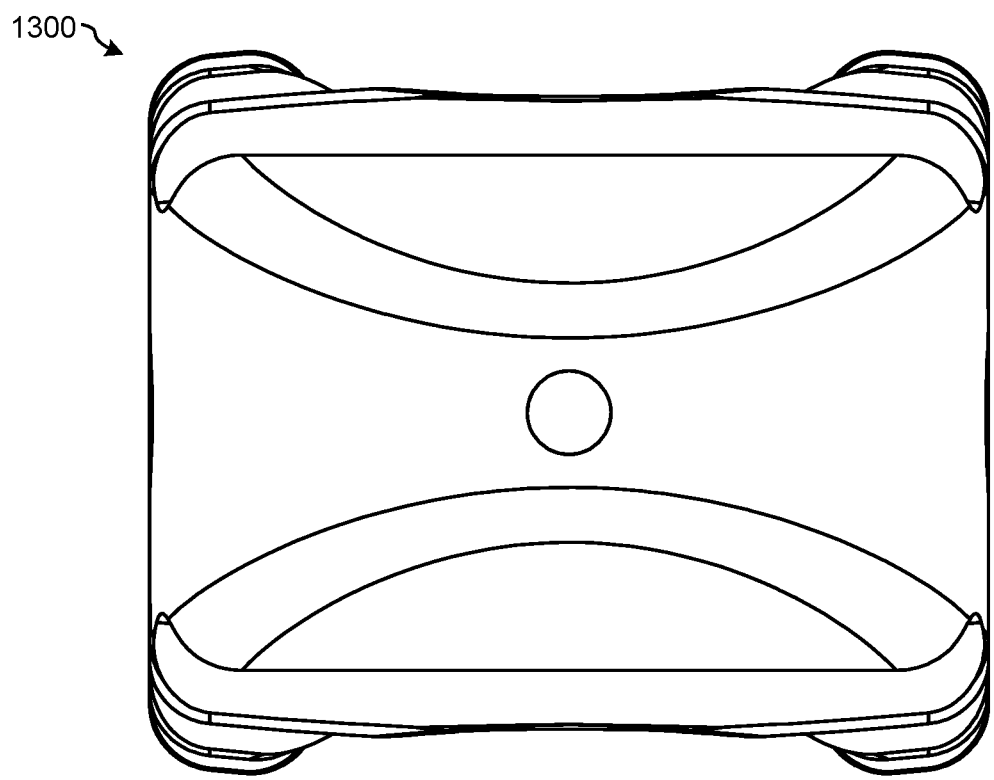
FIG. 13G illustrates the distal end of the intervertebral spacer 1300 of FIG. 13A.
Figure 13H:
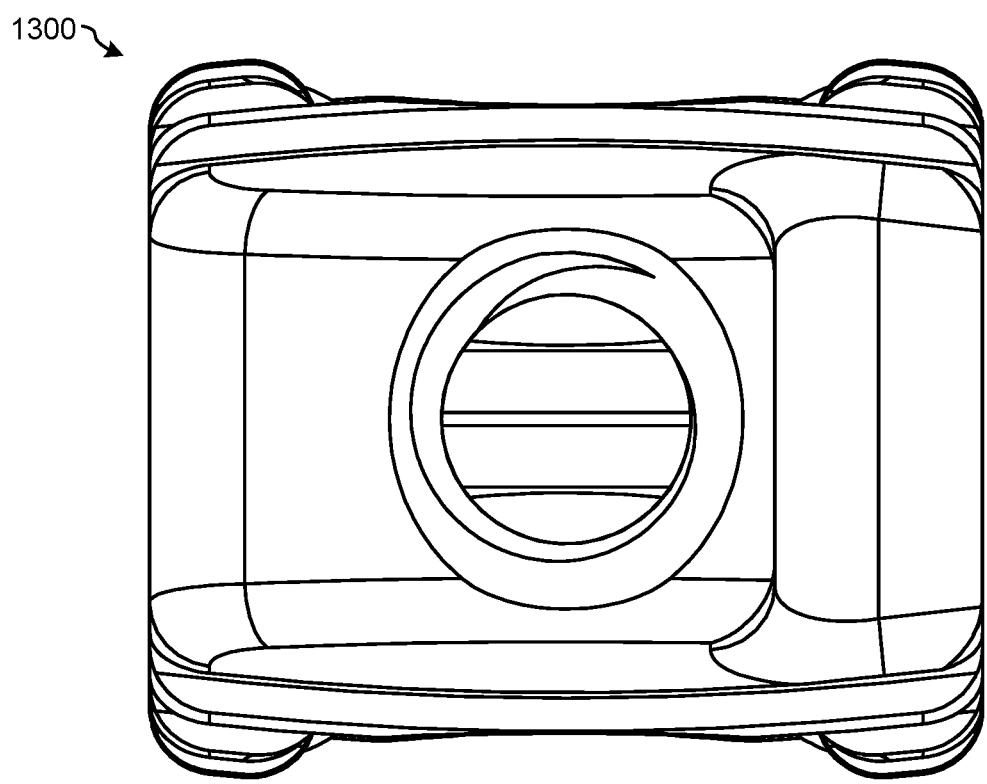
FIG. 13H illustrates the proximal end of the intervertebral spacer 1300 of FIG. 13A.
Figure 14A:
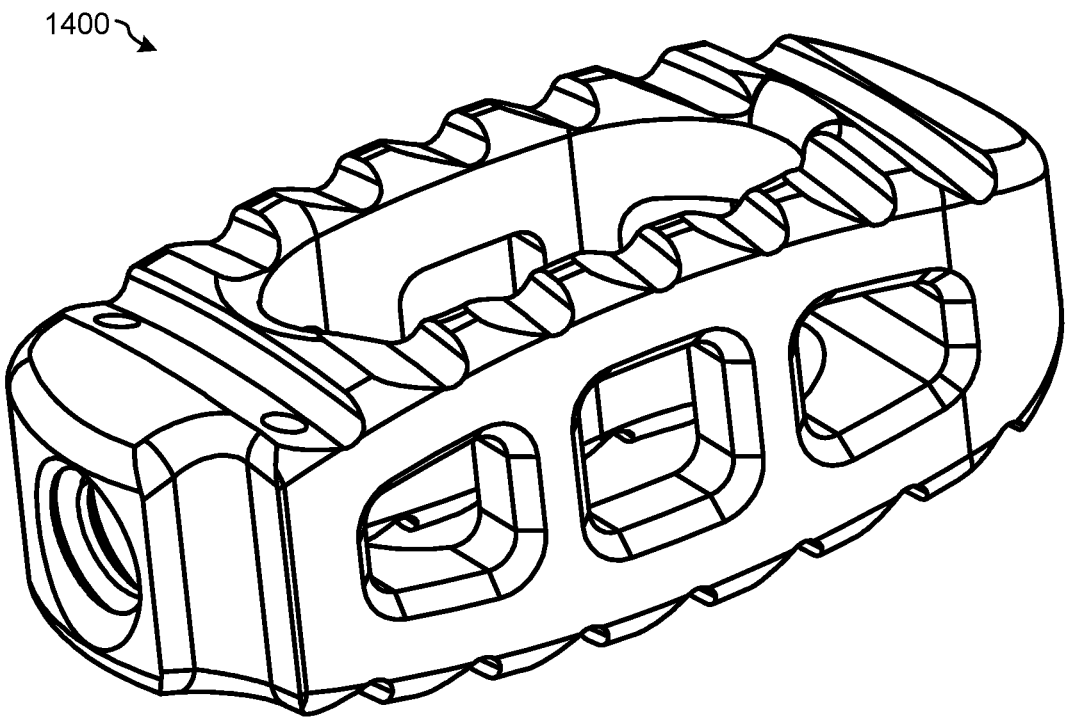
FIG. 14A is a perspective top view of a proximal end of an intervertebral spacer 1400, according to an embodiment of the present disclosure.
Figure 14B:
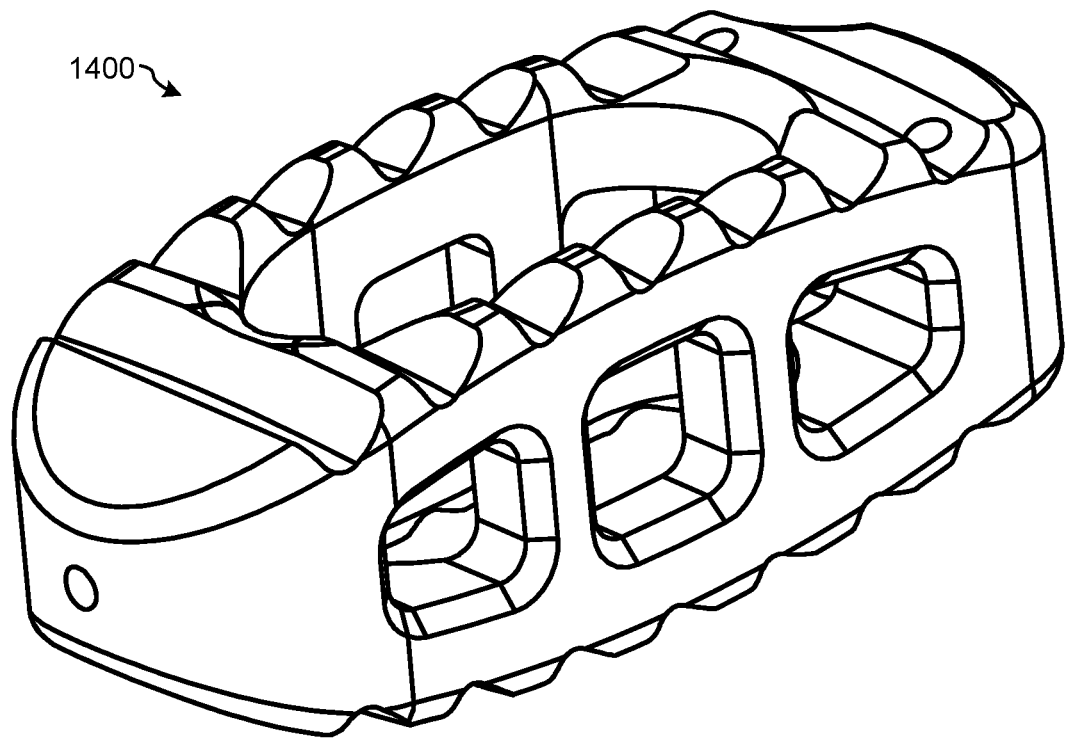
FIG. 14B is a perspective top view of a distal end of the intervertebral spacer 1400 of FIG. 14A.
Figure 14C:
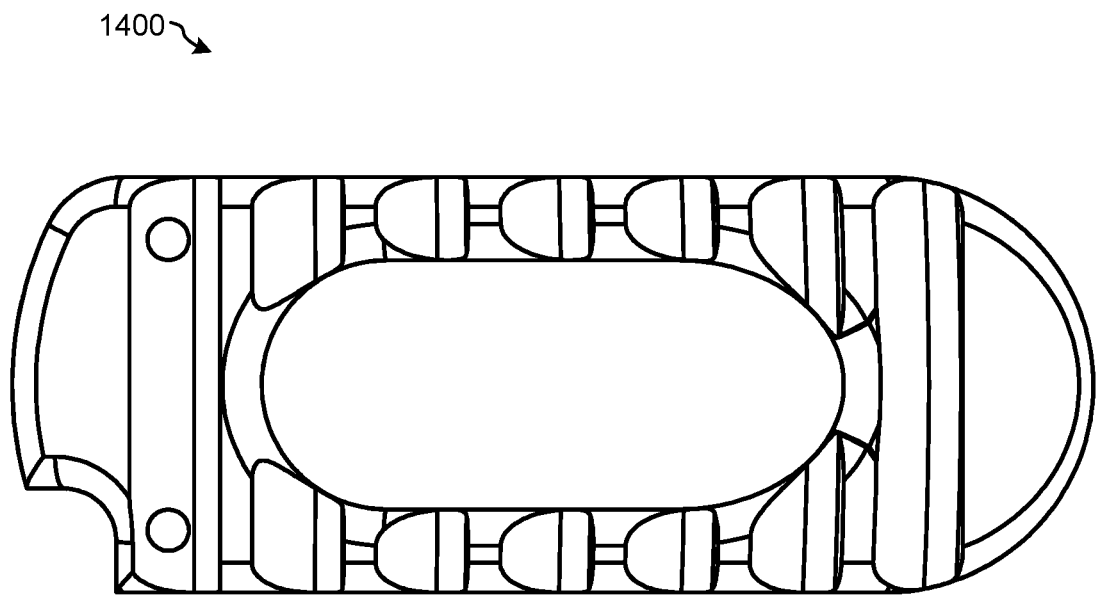
FIG. 14C is a top view of the intervertebral spacer 1400 of FIG. 14A.
Figure 14D:
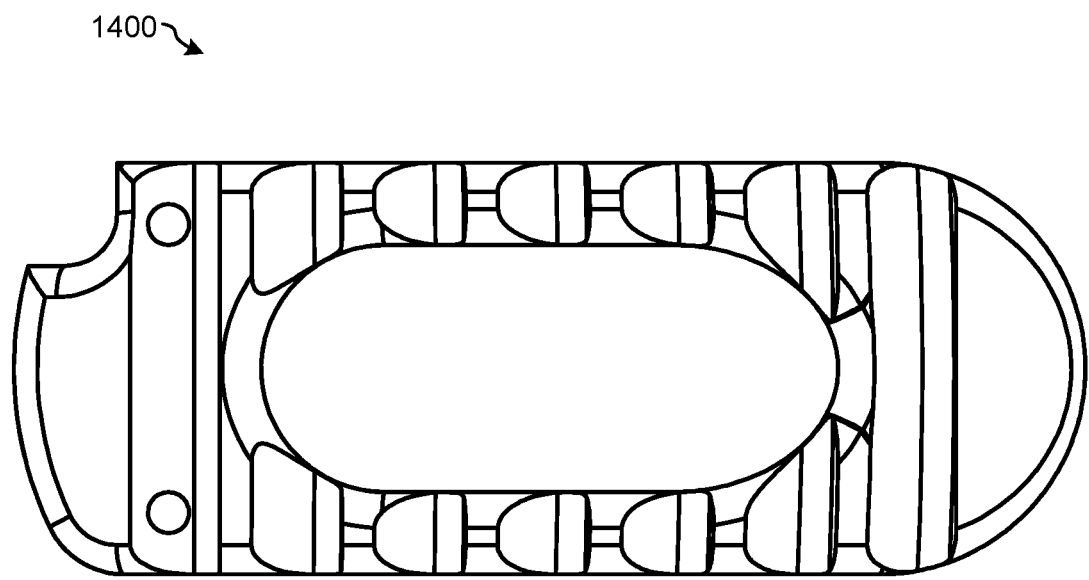
FIG. 14D is a bottom view of the intervertebral spacer 1400 of FIG. 14A.
Figure 14E:
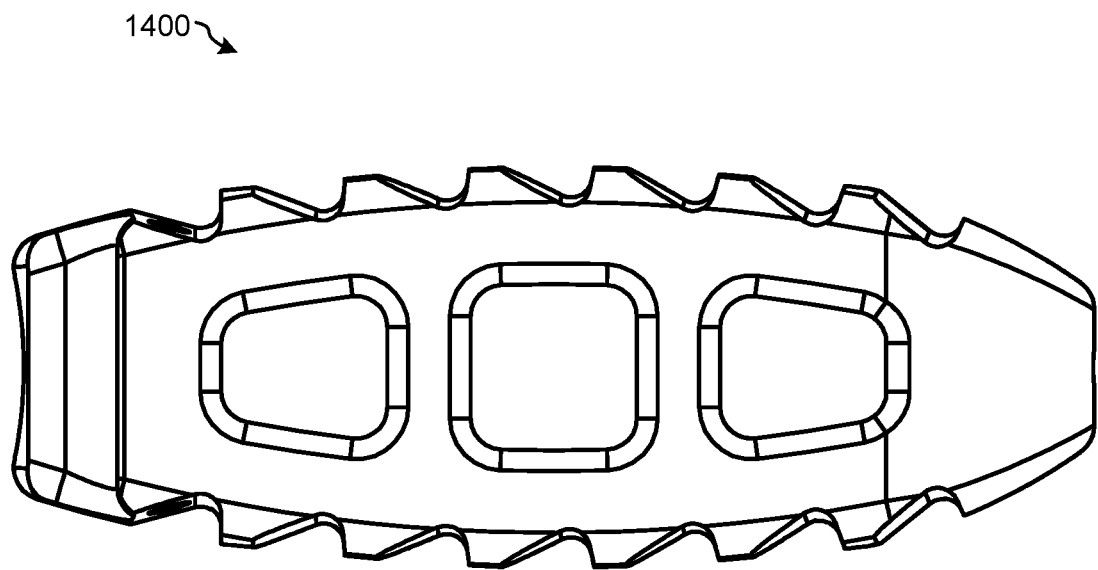
FIG. 14E illustrates a first side of the intervertebral spacer 1400 of FIG. 14A.
Figure 14F:
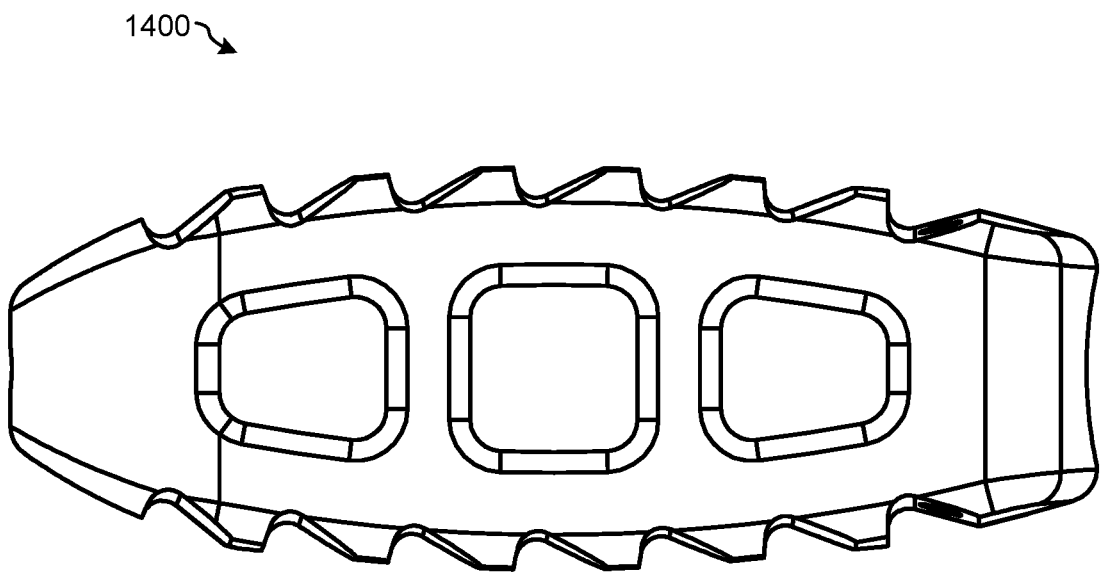
FIG. 14F illustrates a second side of the intervertebral spacer 1400 of FIG. 14A.
Figure 14G:
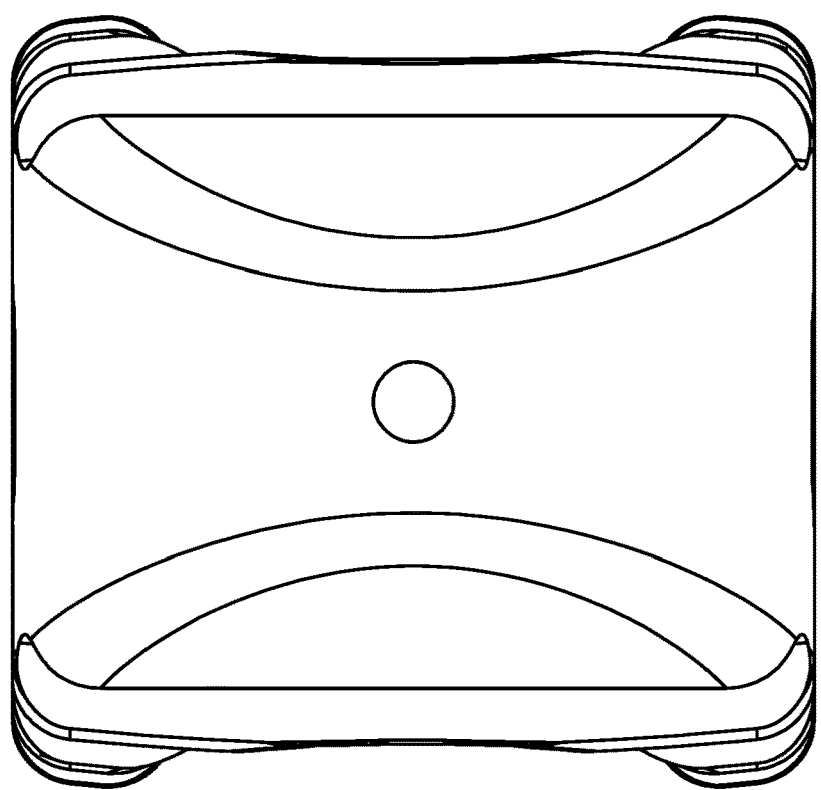
FIG. 14G illustrates the distal end of the intervertebral spacer 1400 of FIG. 14A.
Figure 14H:
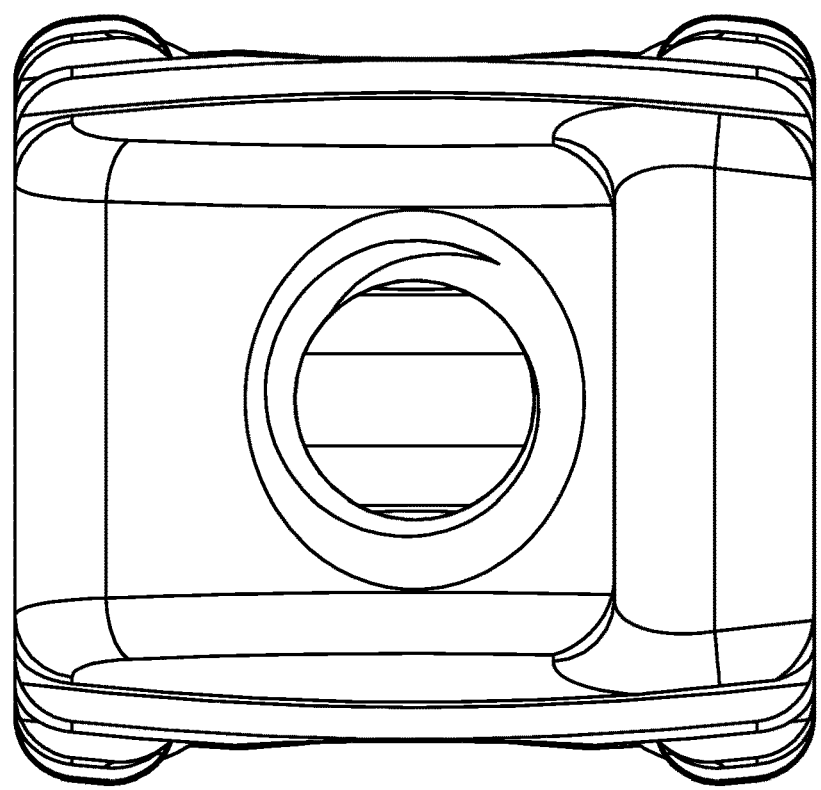
FIG. 14H illustrates the proximal end of the intervertebral spacer 1400 of FIG. 14A.
Figure 15A:
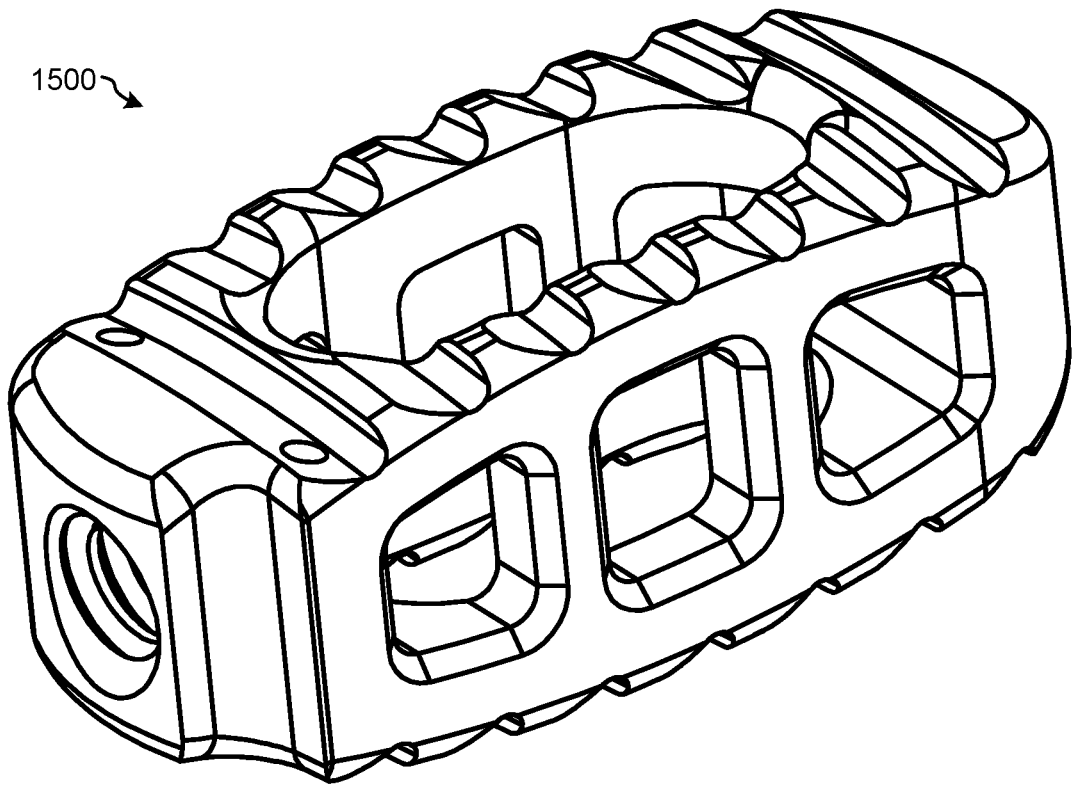
FIG. 15A is a perspective top view of a proximal end of an intervertebral spacer 1500, according to an embodiment of the present disclosure.
Figure 15B:
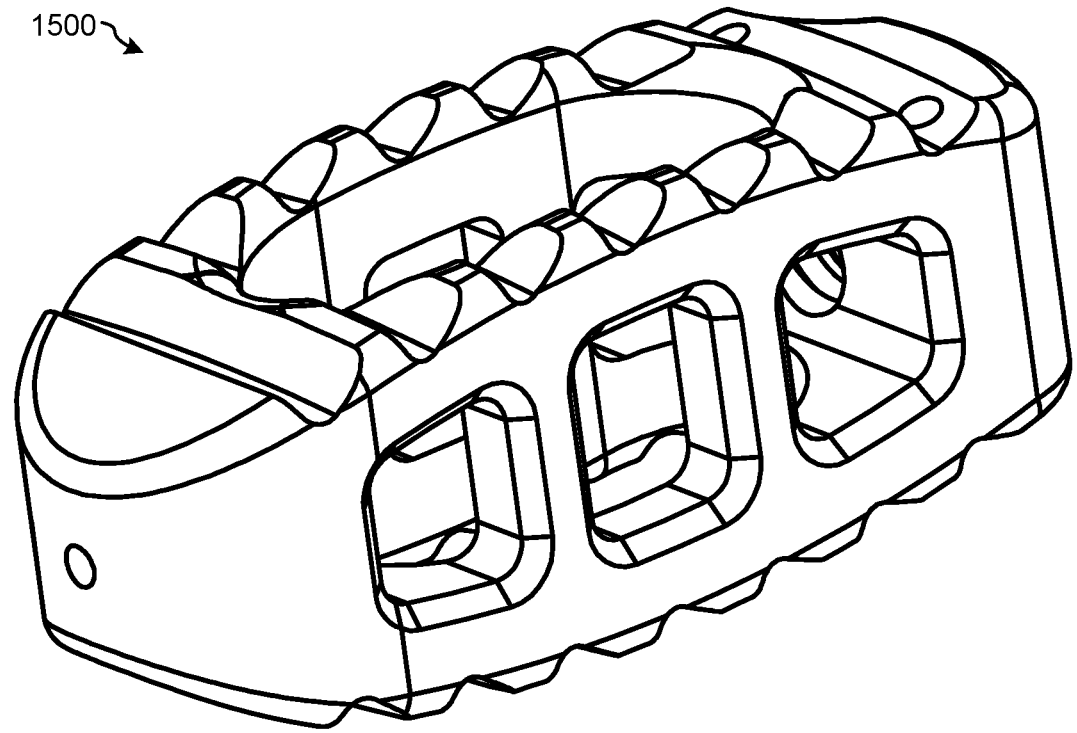
FIG. 15B is a perspective top view of a distal end of the intervertebral spacer 1500 of FIG. 15A.
Figure 15C:
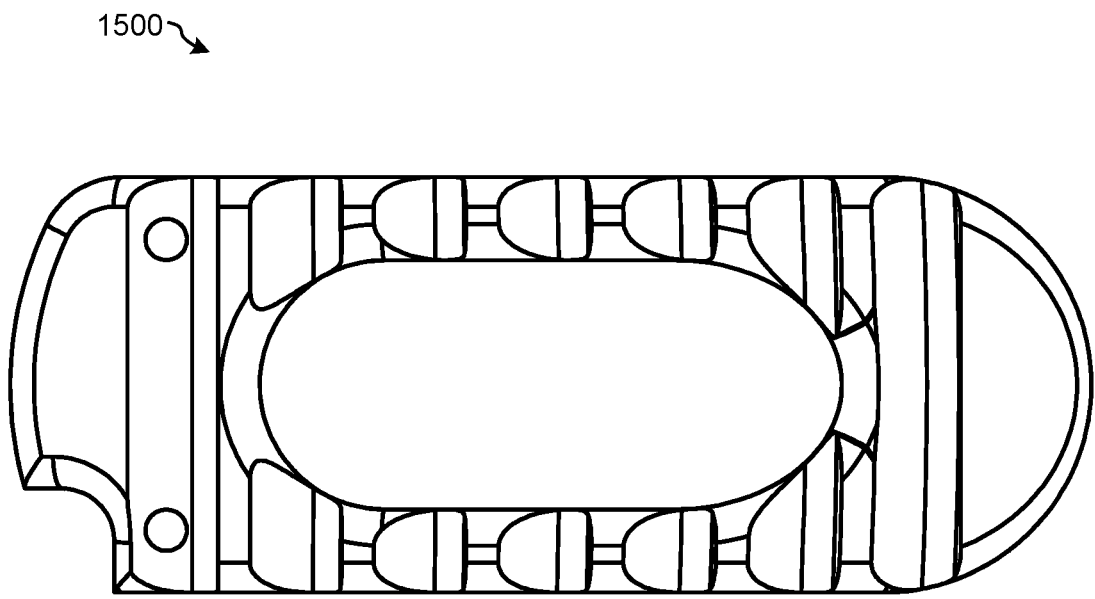
FIG. 15C is a top view of the intervertebral spacer 1500 of FIG. 15A.
Figure 15D:
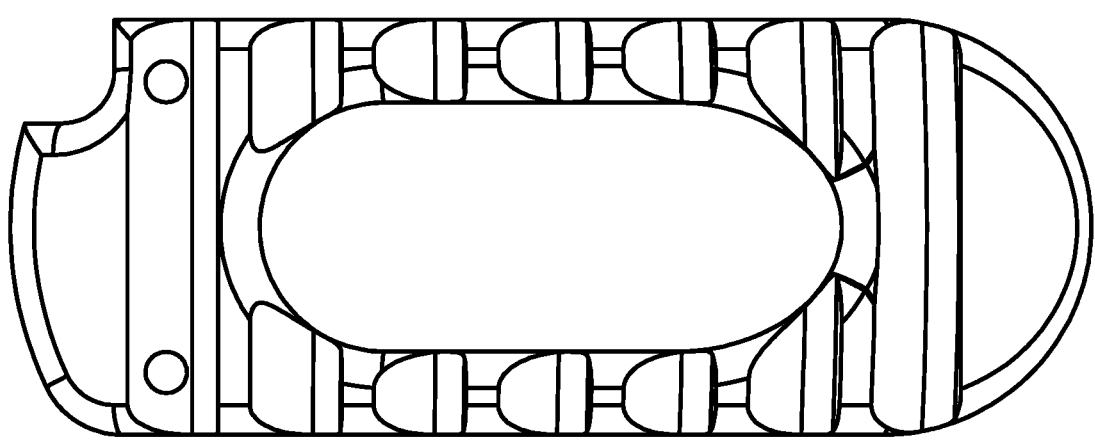
FIG. 15D is a bottom view of the intervertebral spacer 1500 of FIG. 15A.
Figure 15E:
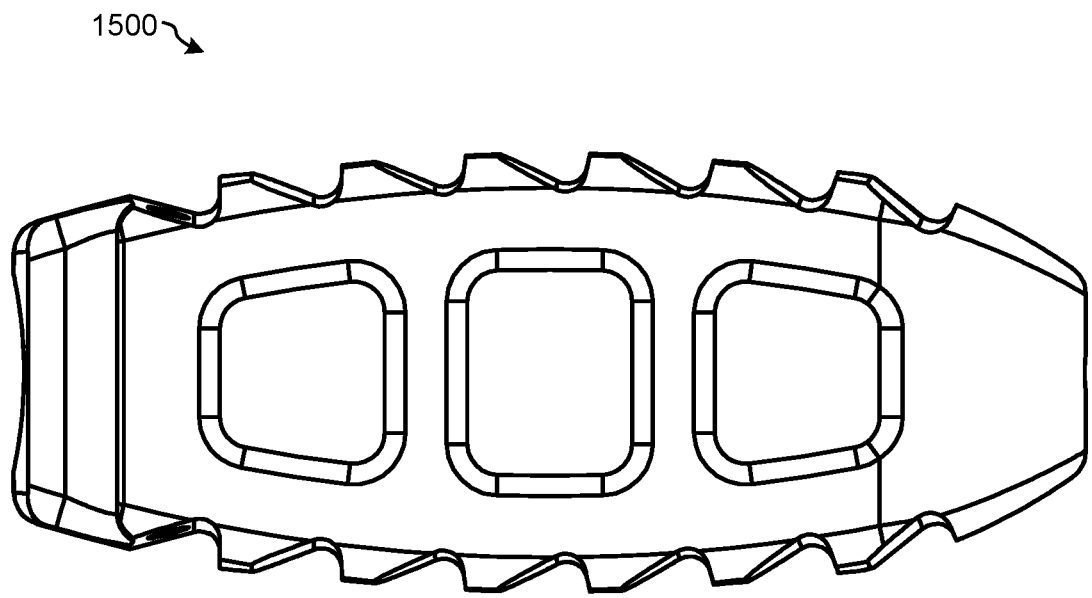
FIG. 15E illustrates a first side of the intervertebral spacer 1500 of FIG. 15A.
Figure 15F:
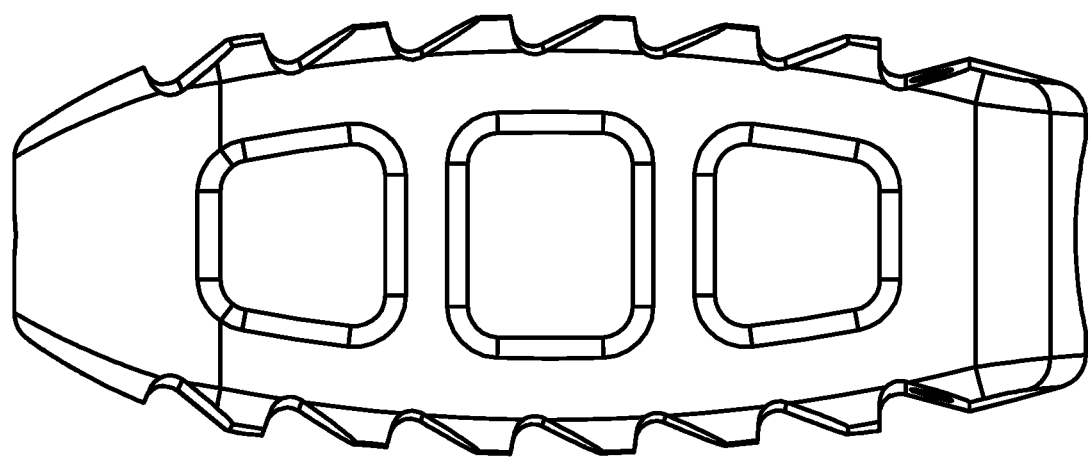
FIG. 15F illustrates a second side of the intervertebral spacer 1500 of FIG. 15A.
Figure 15G:
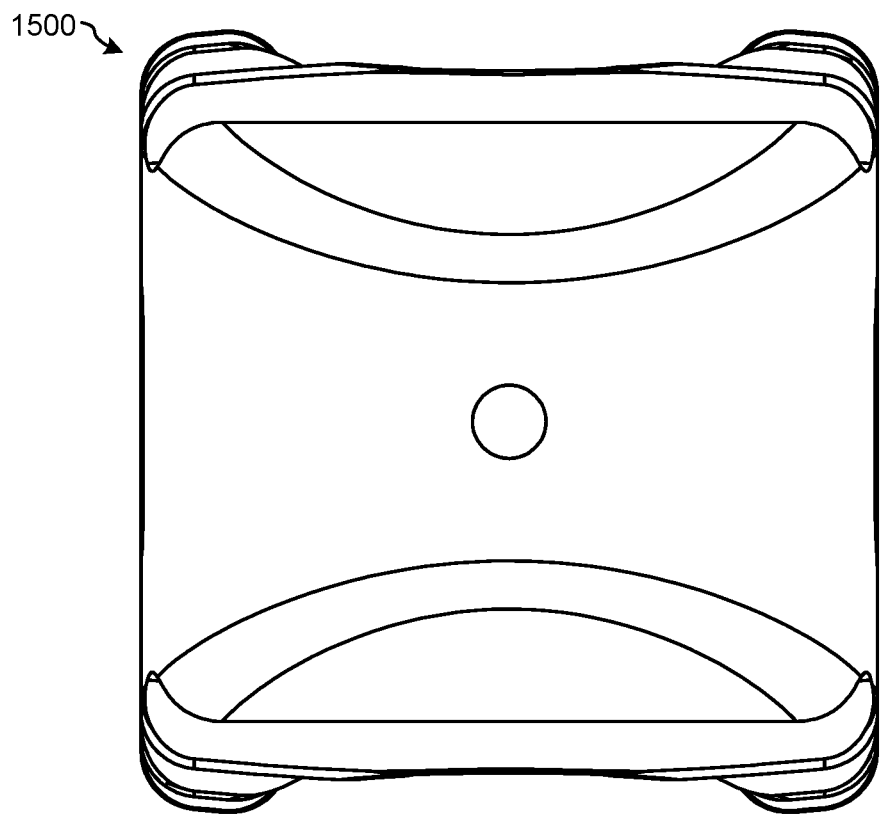
FIG. 15G illustrates the distal end of the intervertebral spacer 1500 of FIG. 15A.
Figure 15H:
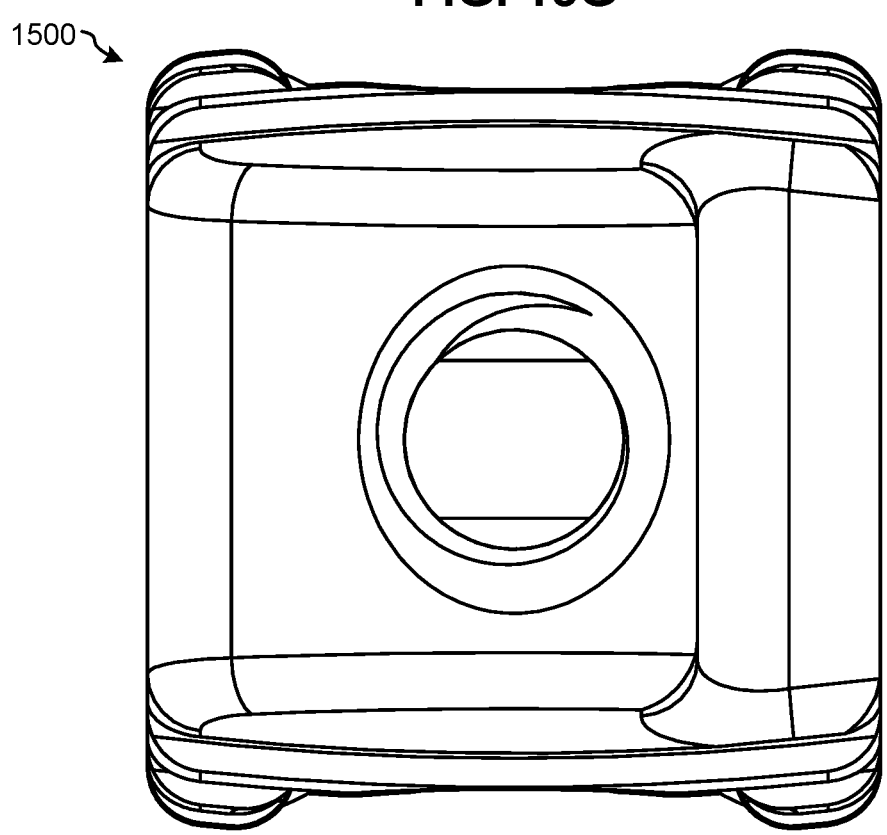
FIG. 15H illustrates the proximal end of the intervertebral spacer 1500 of FIG. 15A.
Figure 16A:
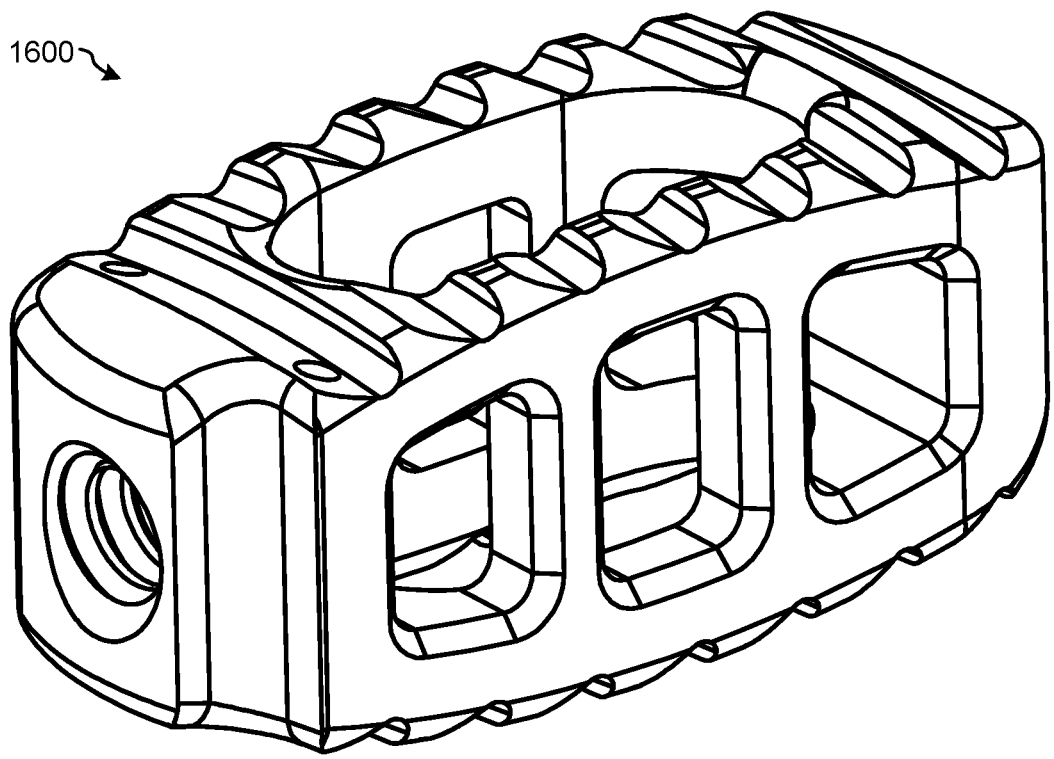
FIG. 16A is a perspective top view of a proximal end of an intervertebral spacer 1600, according to an embodiment of the present disclosure.
Figure 16B:
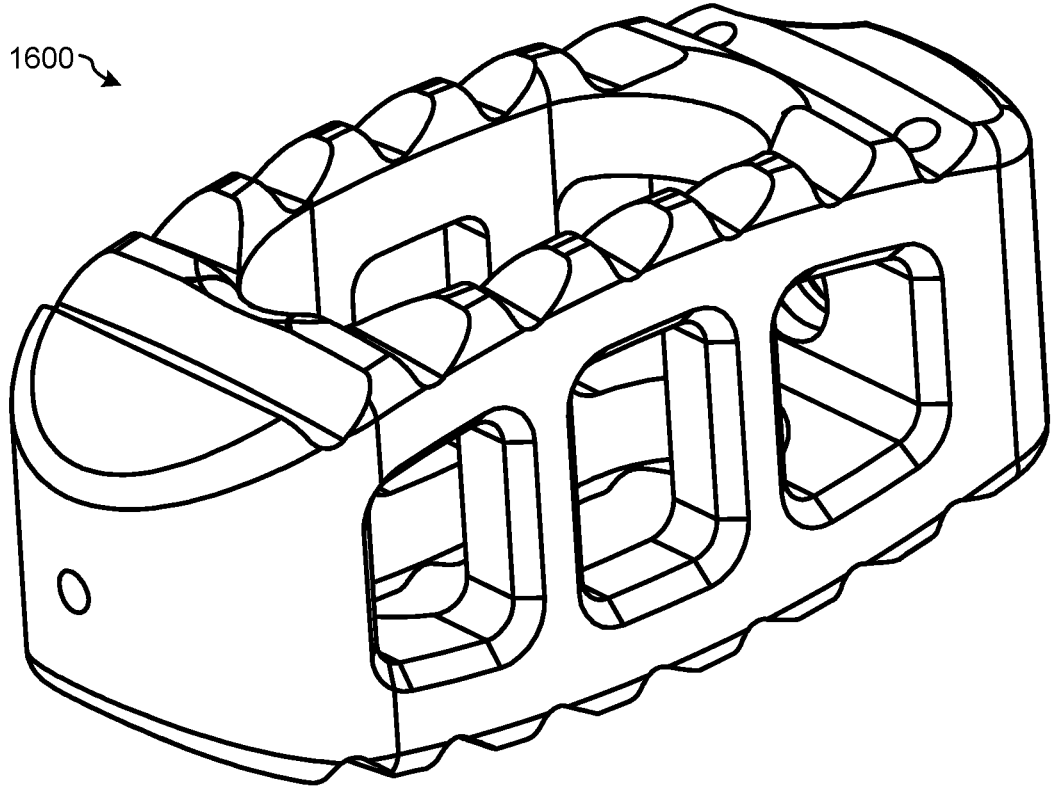
FIG. 16B is a perspective top view of a distal end of the intervertebral spacer 1600 of FIG. 16A.
Figure 16C:
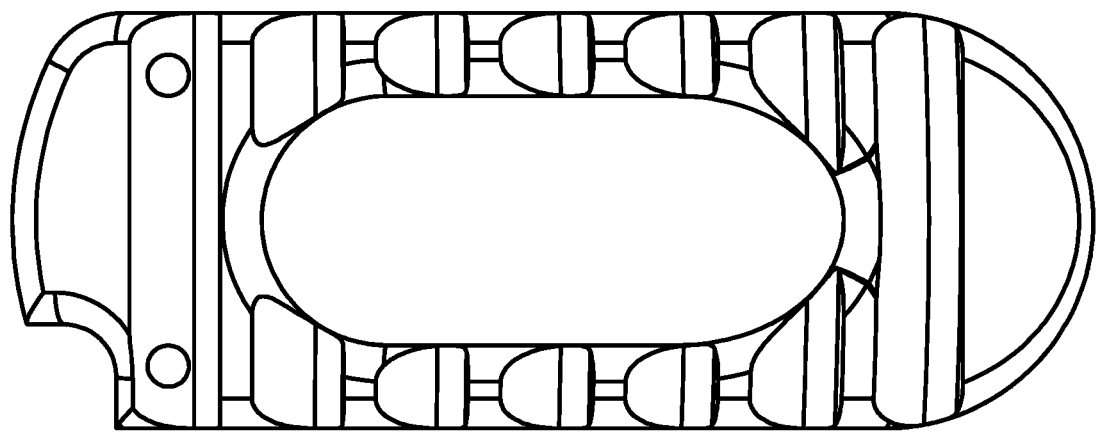
FIG. 16C is a top view of the intervertebral spacer 1600 of FIG. 16A.
Figure 16D:
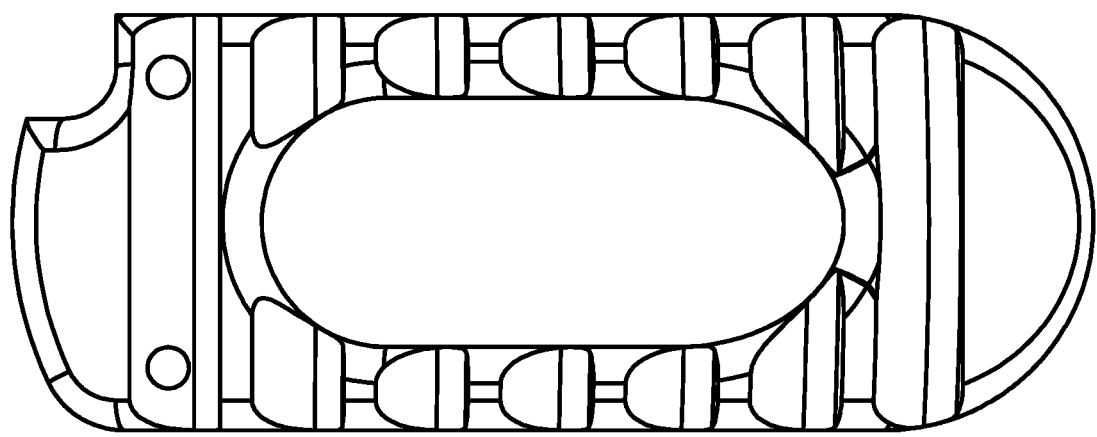
FIG. 16D is a bottom view of the intervertebral spacer 1600 of FIG. 16A.
Figure 16E:
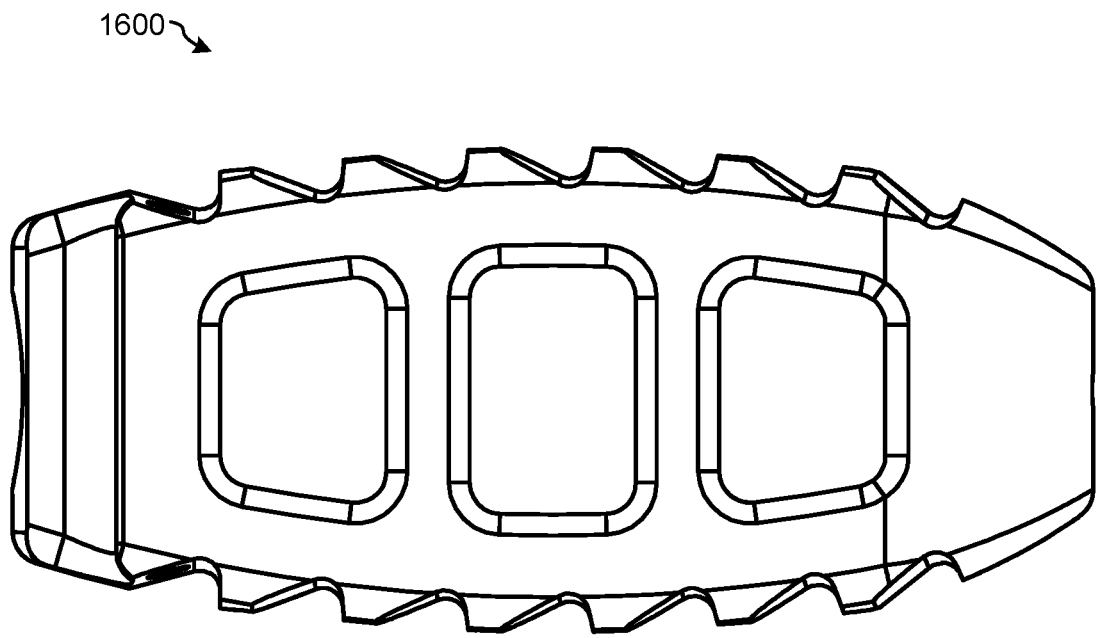
FIG. 16E illustrates a first side of the intervertebral spacer 1600 of FIG. 16A.
Figure 16F:
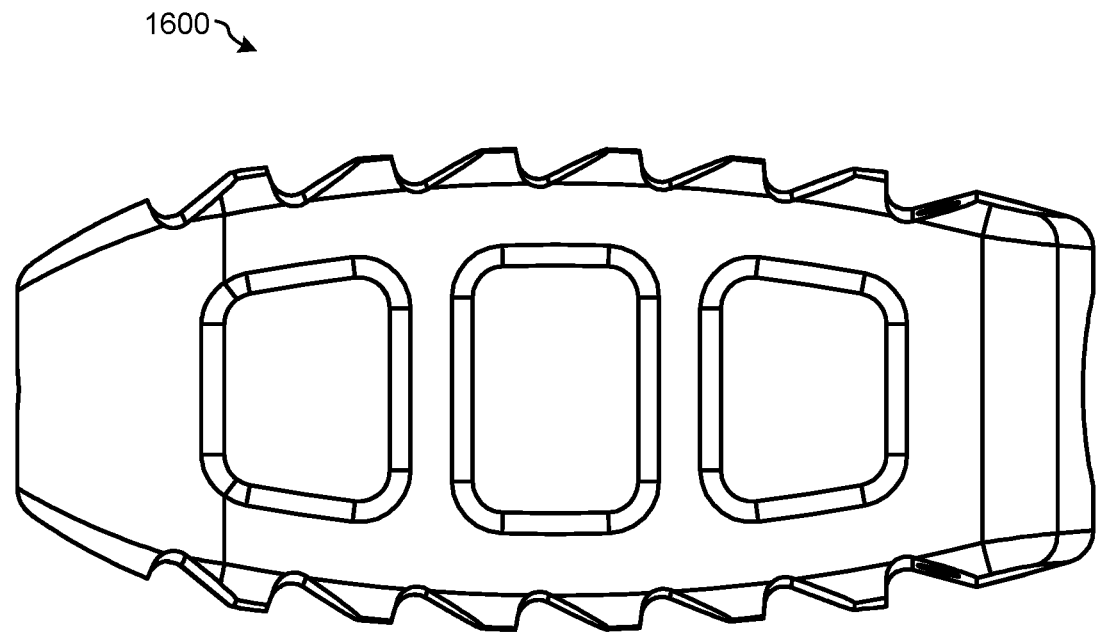
FIG. 16F illustrates a second side of the intervertebral spacer 1600 of FIG. 16A.
Figure 16G:
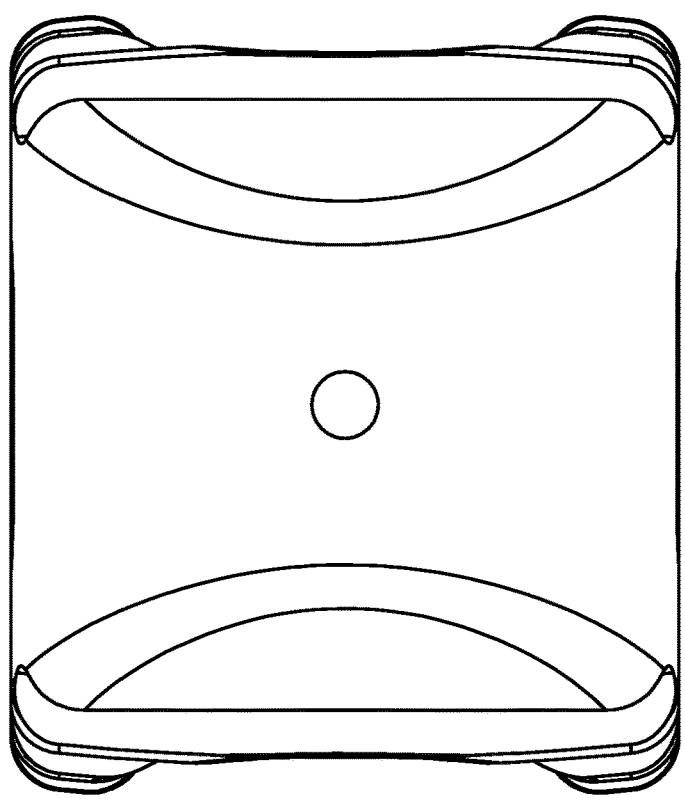
FIG. 16G illustrates the distal end of the intervertebral spacer 1600 of FIG. 16A.
Figure 16H:
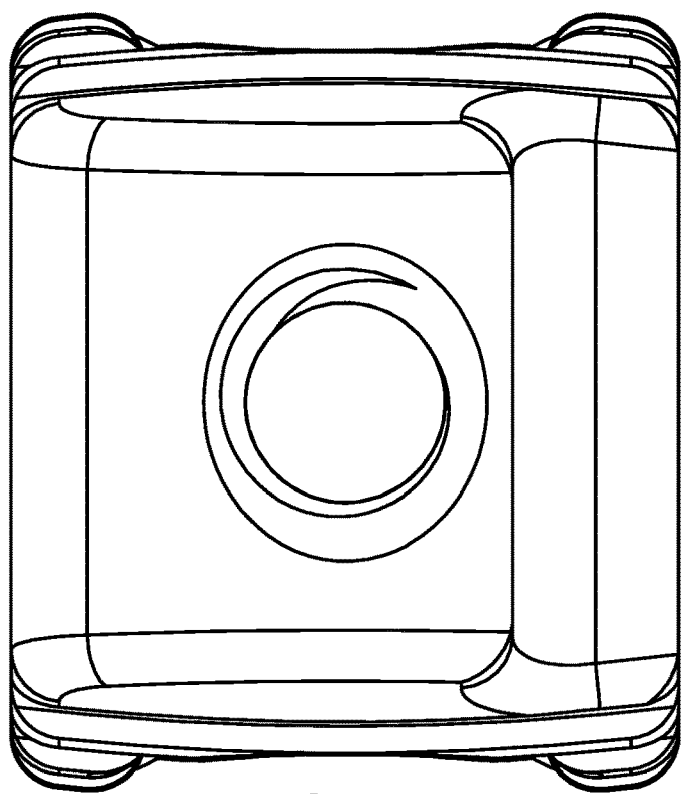
FIG. 16H illustrates the proximal end of the intervertebral spacer 1600 of FIG. 16A.
Figure 17A:
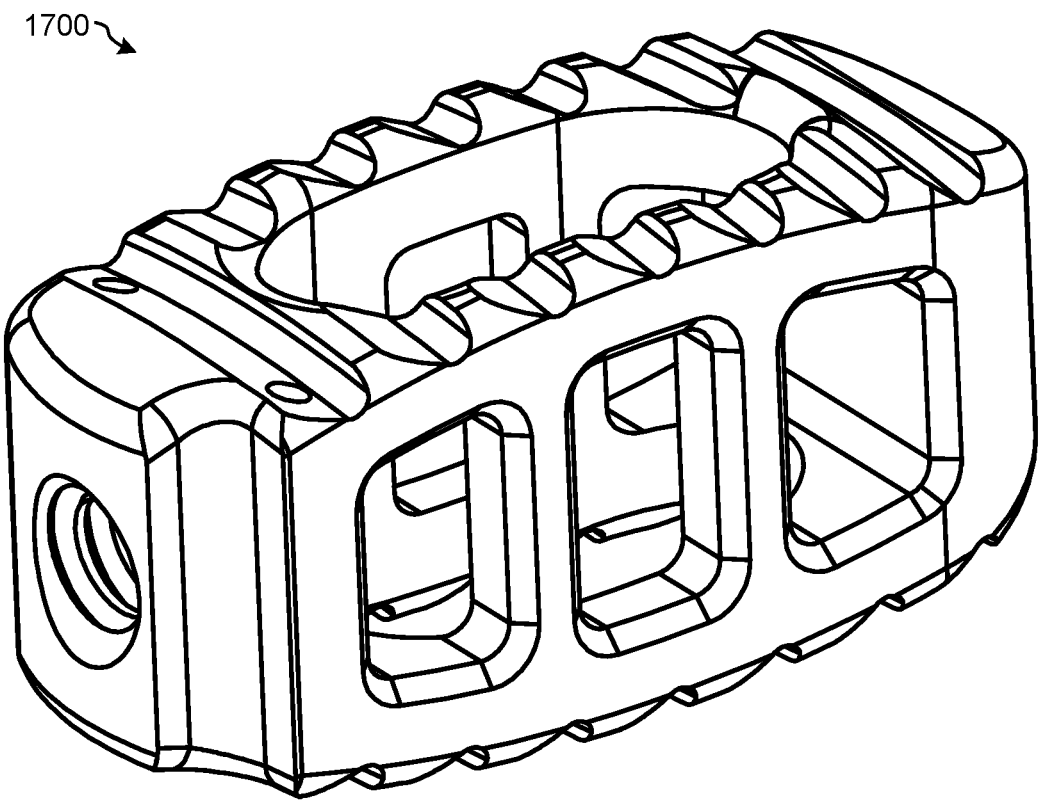
FIG. 17A is a perspective top view of a proximal end of an intervertebral spacer 1700, according to an embodiment of the present disclosure.
Figure 17B:
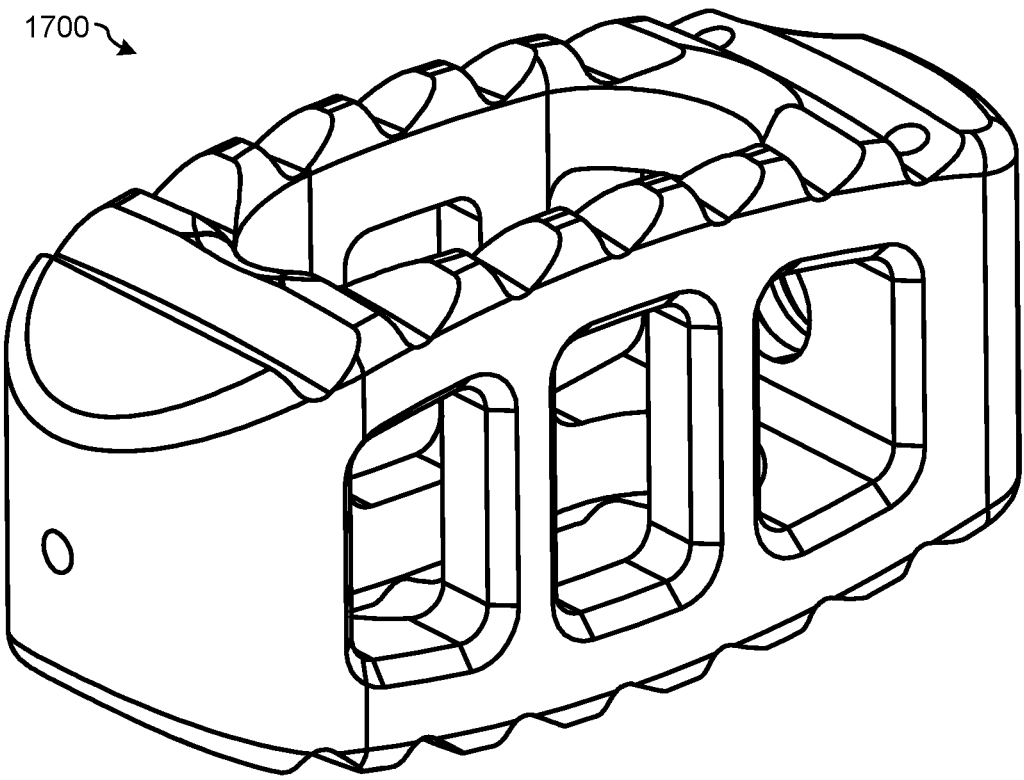
FIG. 17B is a perspective top view of a distal end of the intervertebral spacer 1700 of FIG. 17A.
Figure 17C:
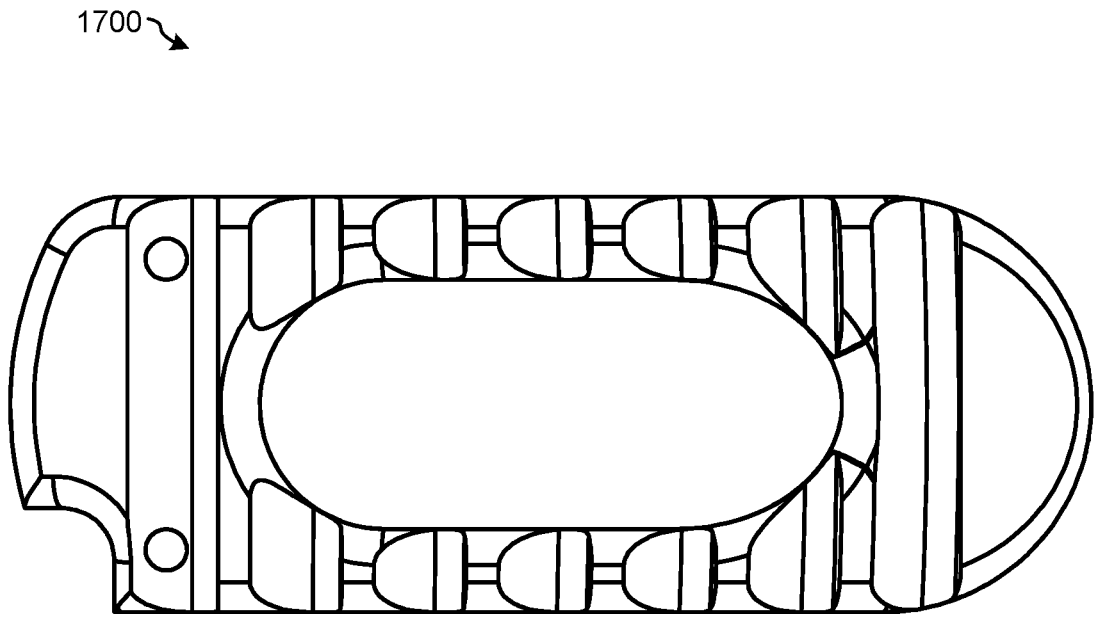
FIG. 17C is a top view of the intervertebral spacer 1700 of FIG. 17A.
Figure 17D:
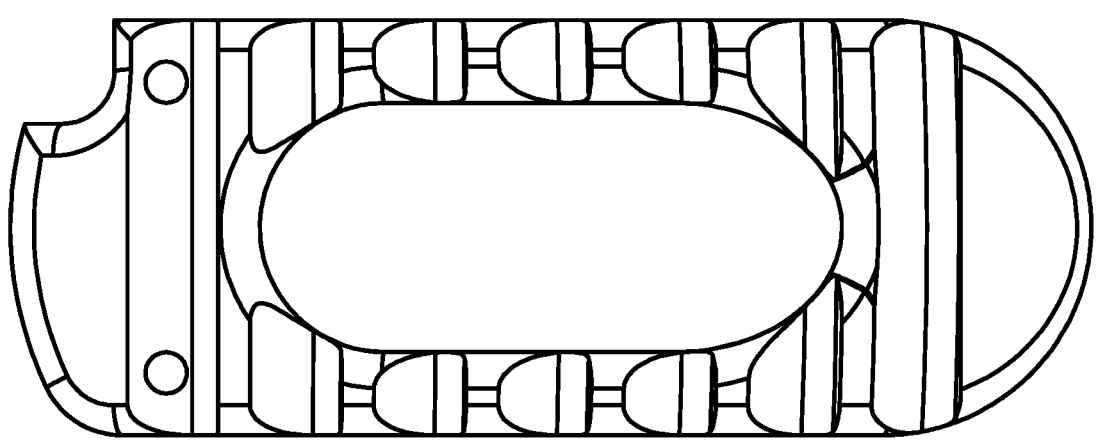
FIG. 17D is a bottom view of the intervertebral spacer 1700 of FIG. 17A.
Figure 17E:
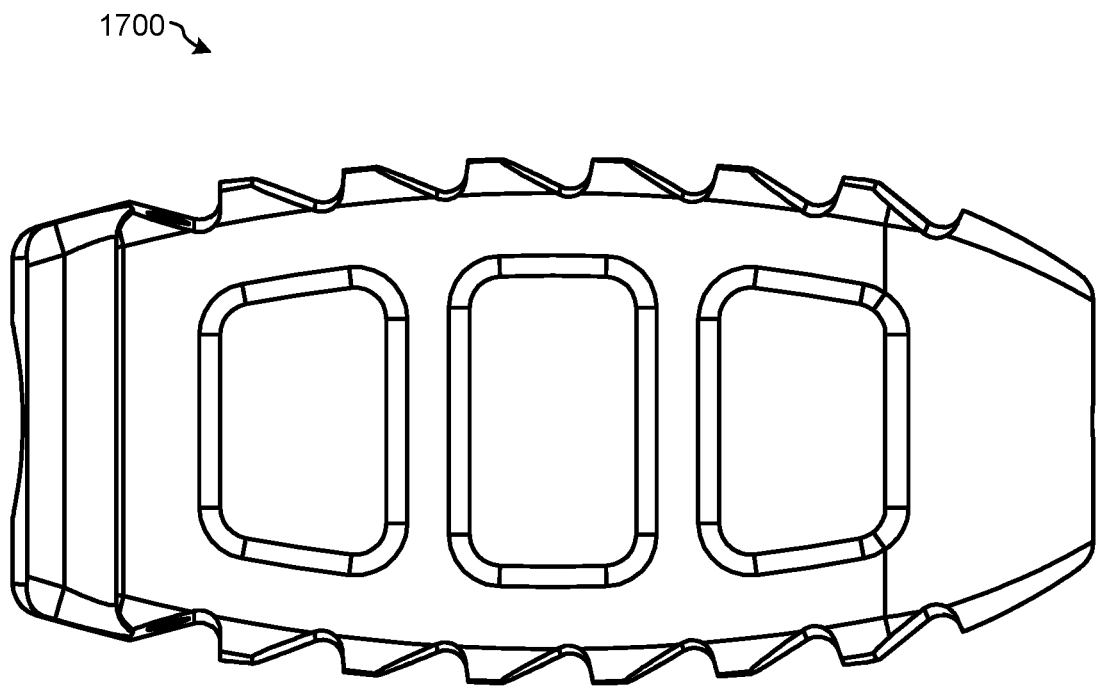
FIG. 17E illustrates a first side of the intervertebral spacer 1700 of FIG. 17A.
Figure 17F:
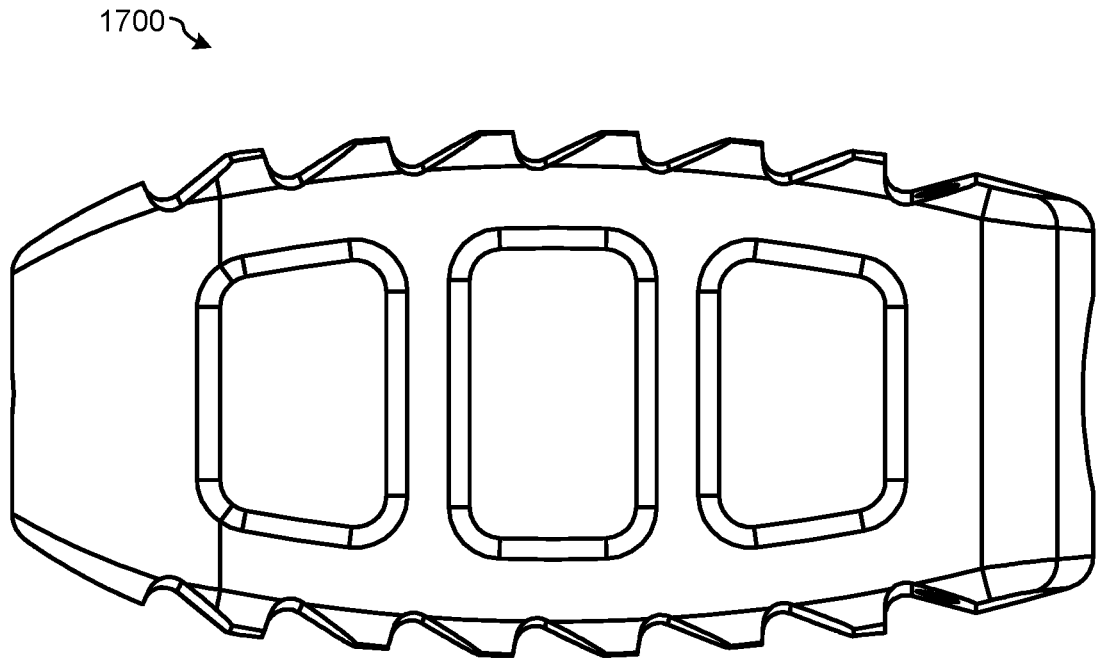
FIG. 17F illustrates a second side of the intervertebral spacer 1700 of FIG. 17A.
Figure 17G:
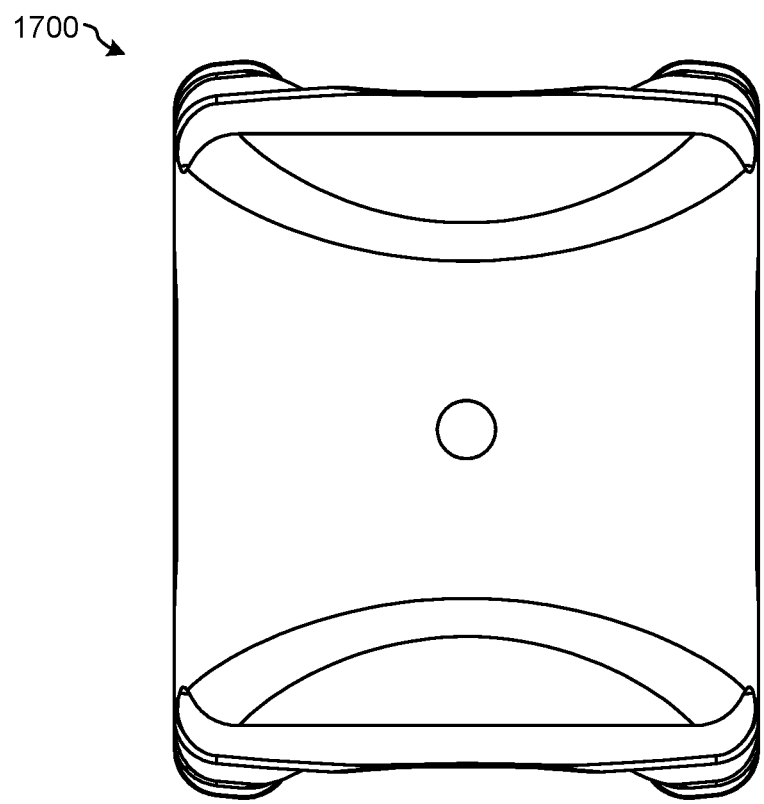
FIG. 17G illustrates the distal end of the intervertebral spacer 1700 of FIG. 17A.
Figure 17H:
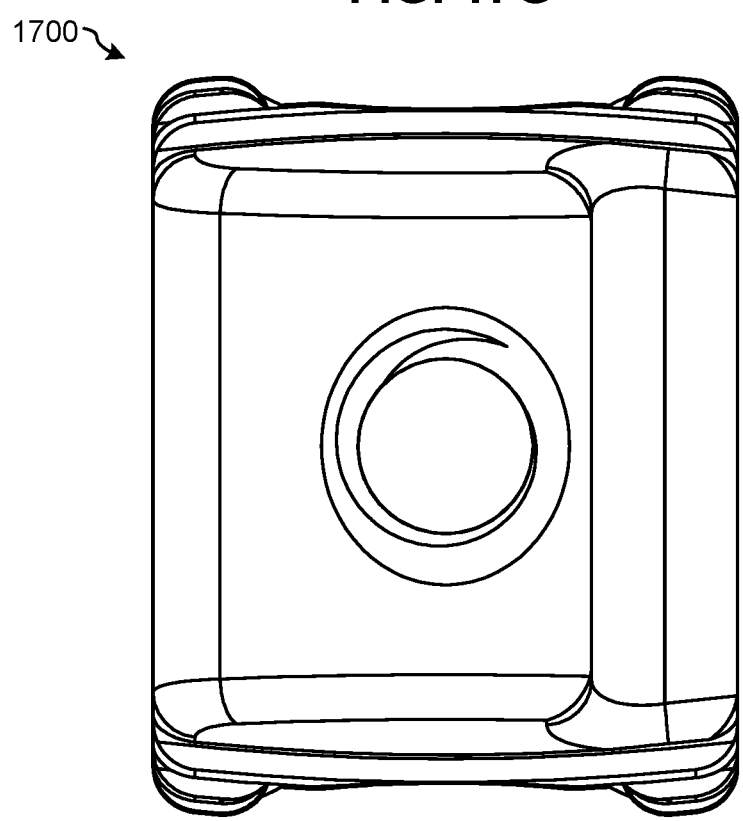
FIG. 17H illustrates the proximal end of the intervertebral spacer 1700 of FIG. 17A.
Figure 18A:
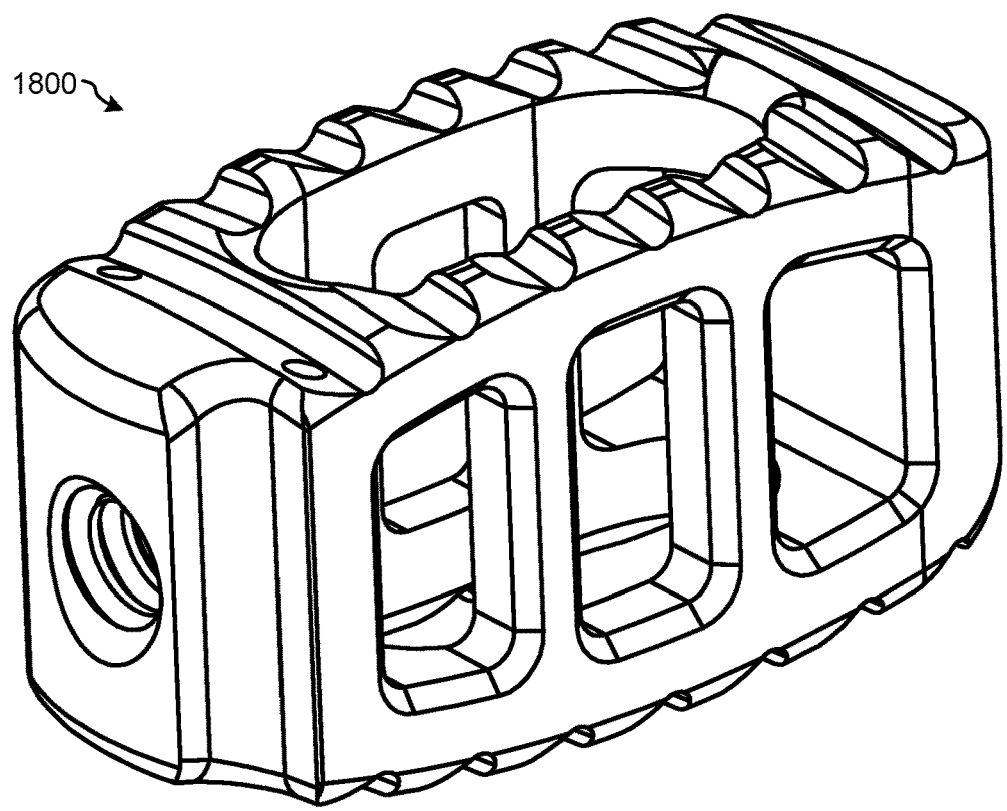
FIG. 18A is a perspective top view of a proximal end of an intervertebral spacer 1800, according to an embodiment of the present disclosure.
Figure 18B:
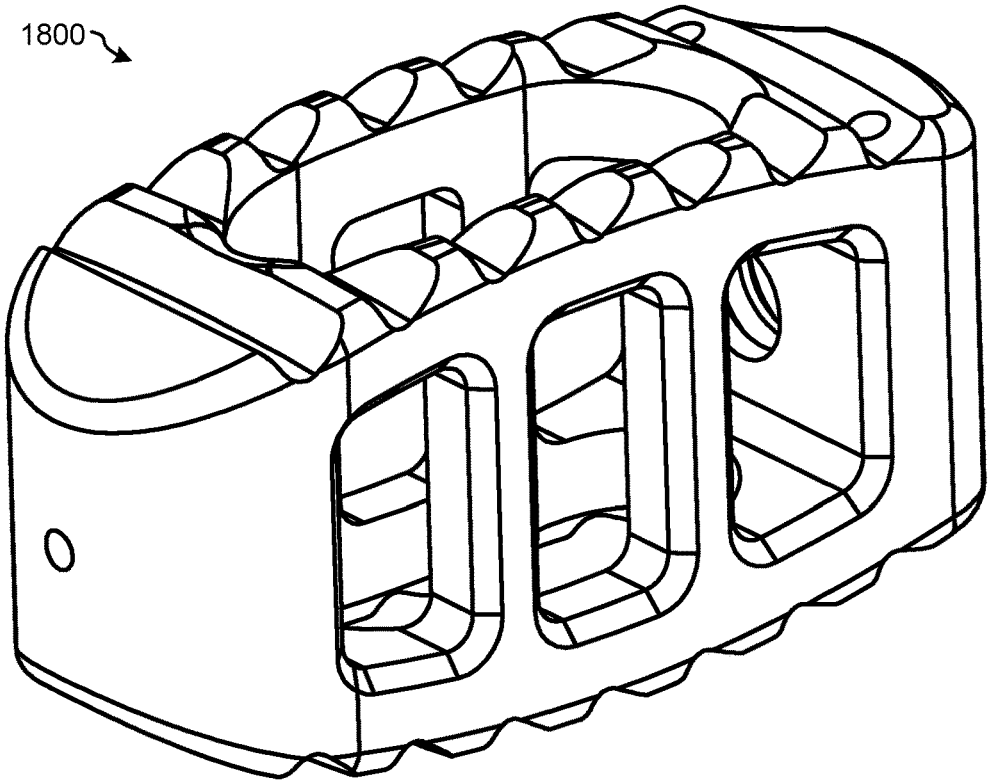
Figure 18C:
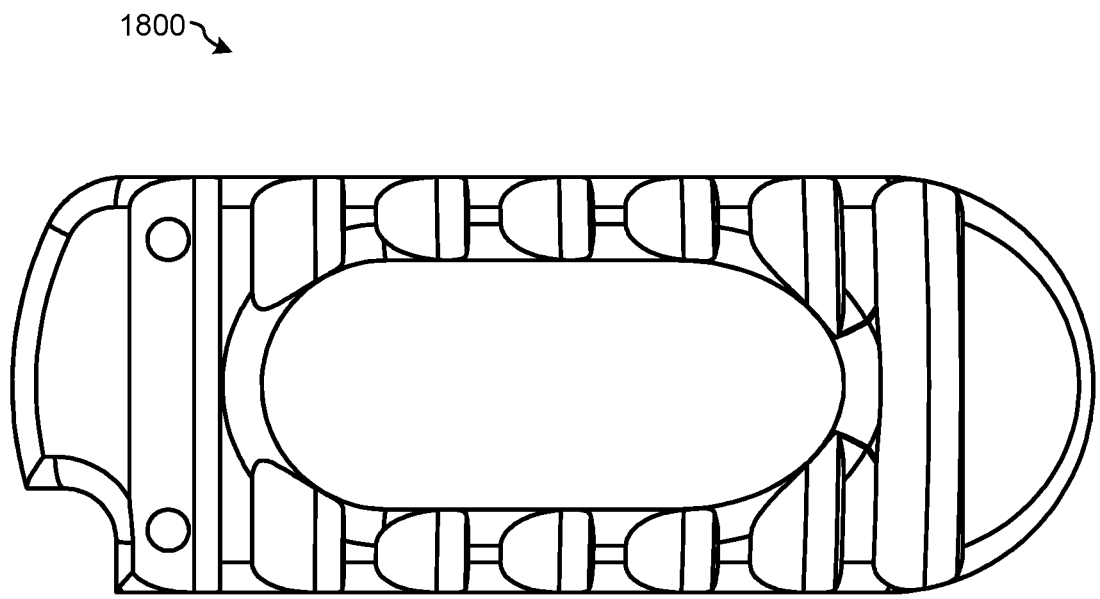
Figure 18D:
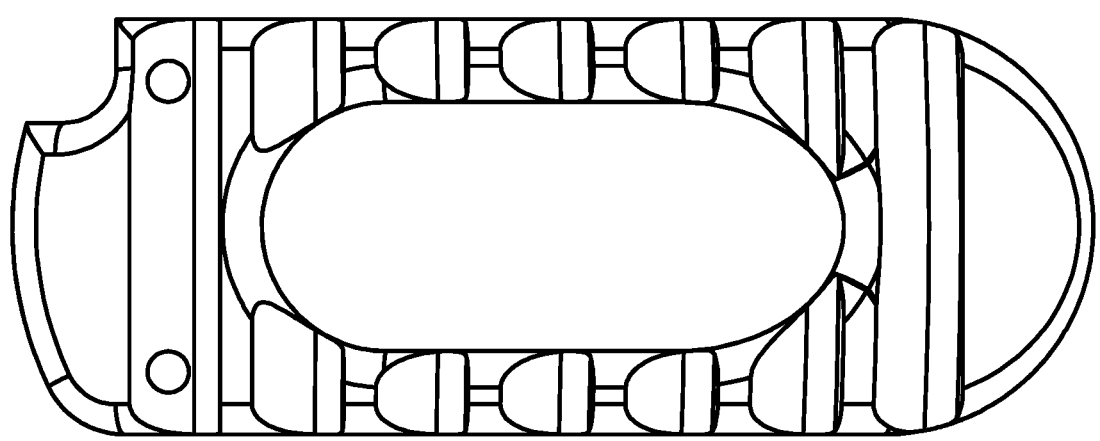
Figure 18E:
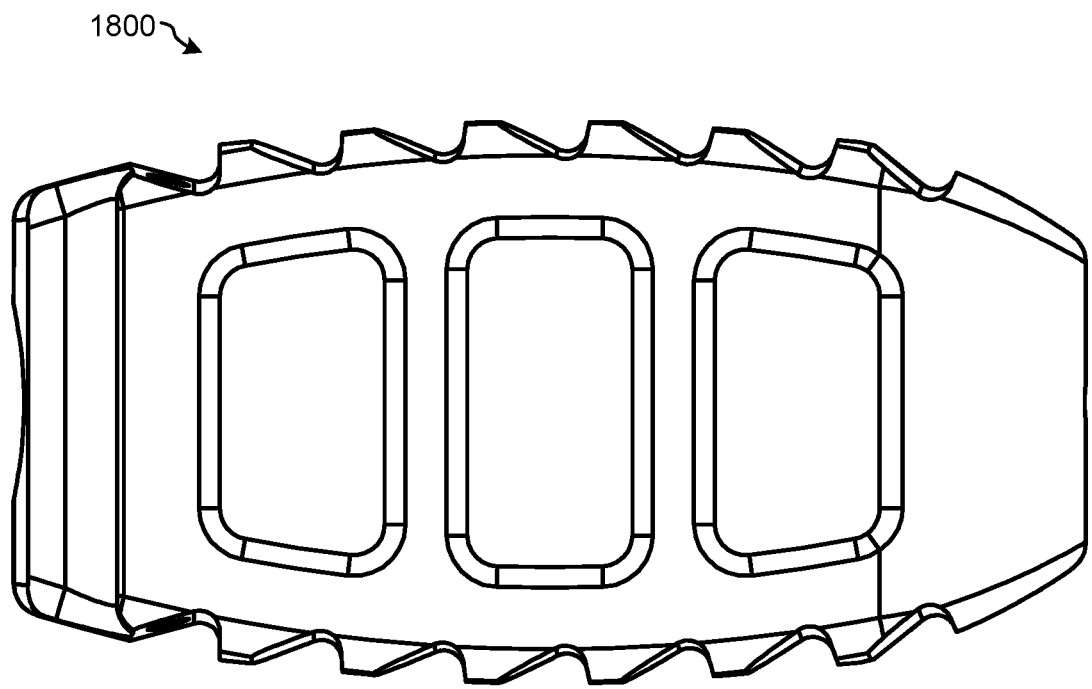
Figure 18F:
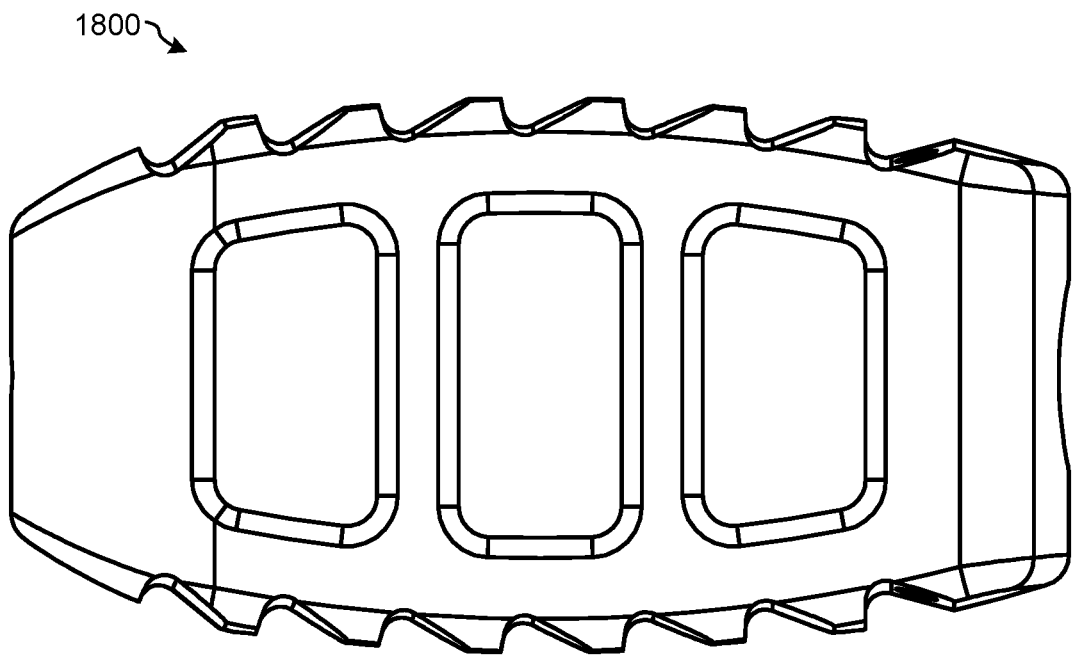
Figure 18G:
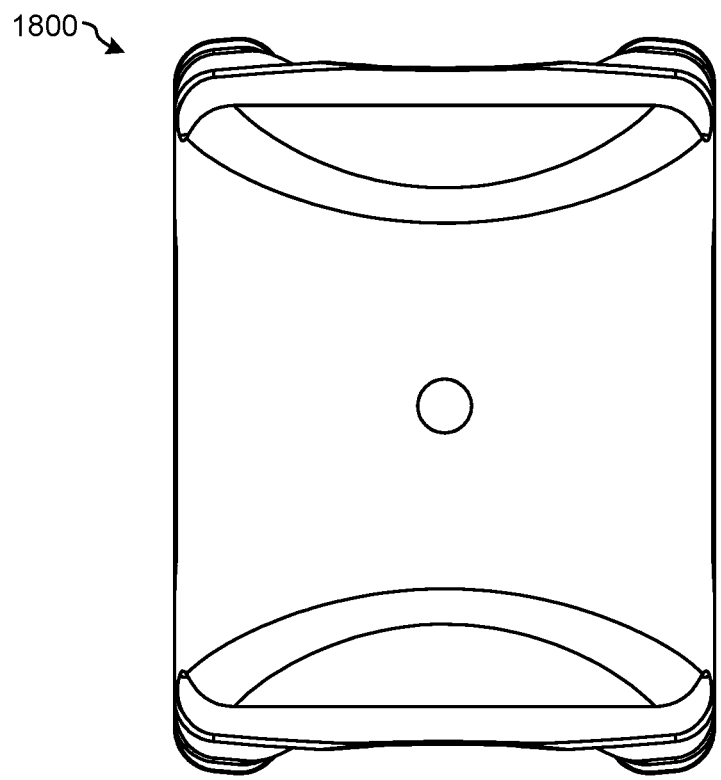
Figure 18H:
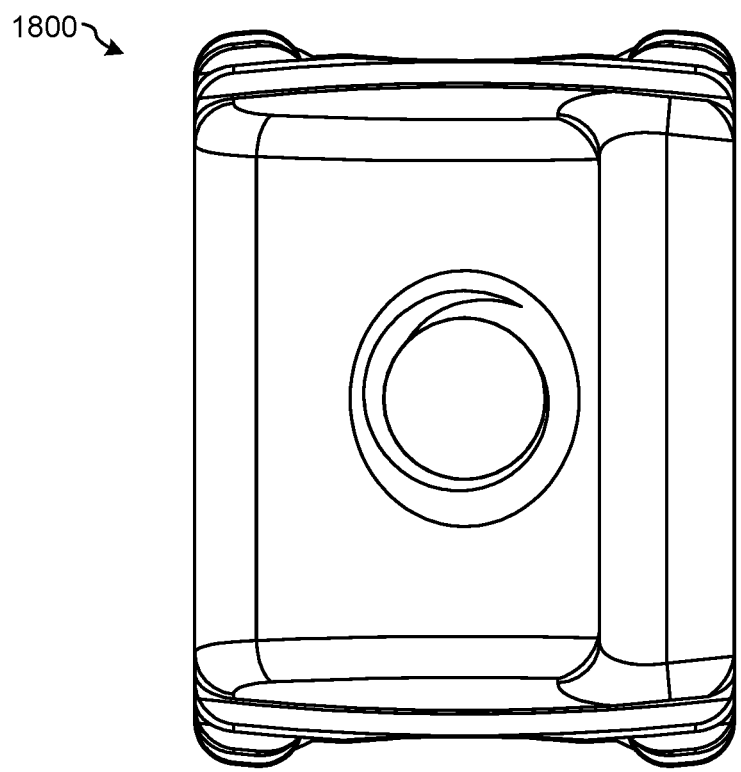

The intervertebral spacer 100 may also include one or more first marker apertures 150 and a second marker aperture 152. The one or more first marker apertures 150 may each be configured to receive a first radiopaque maker 200, as shown in FIGS. 2A and 2B. The second marker aperture 152 may be configured to receive a second radiopaque maker 300, as shown in FIGS. 3A and 3B. The first and second radiopaque makers 200, 300 may be made from any suitable radiopaque material, such as tantalum (as one non-limiting example). The first and second radiopaque makers 200, 300 may be respectively inserted into the first and second marker apertures 150, 152 in order to couple the first and second radiopaque makers 200, 300 to the intervertebral spacer 100, as can be seen in the exploded view shown in FIG. 4. In this manner, the first and second radiopaque makers 200, 300 may be used to verify whether or not the intervertebral spacer 100 has been correctly placed between adjacent vertebral bodies via a suitable x-ray imaging process, which may be performed intraoperatively and/or postoperatively.

FIGS. 5A-18H illustrate various views of differently sized intervertebral spacers, according to embodiments of the present disclosure. Specifically, FIGS. 5A-5H illustrate various views of an intervertebral spacer 500 having a height "H" (see FIG. 5E) of about 8 mm and a length "L" (see FIG. 5E) of about 22 mm; FIGS. 6A-6H illustrate various views of an intervertebral spacer 600 having a height of about 9 mm and a length of about 22 mm; FIGS. 7A-7H illustrate various views of an intervertebral spacer 700 having a height of about 10 mm and a length of about 22 mm; FIGS. 8A-8H illustrate various views of an intervertebral spacer 800 having a height of about 11 mm and a length of about 22 mm; FIGS. 9A-9H illustrate various views of an intervertebral spacer 900 having a height of about 12 mm and a length of about 22 mm; FIGS. 10A-10H illustrate various views of an intervertebral spacer 1000 having a height of about 13 mm and a length of about 22 mm; FIGS. 11A-11H illustrate various views of an intervertebral spacer 1100 having a height of about 14 mm and a length of about 22 mm; FIGS. 12A-12H illustrate various views of an intervertebral spacer 1200 having a height of about 8 mm and a length of about 26 mm; FIGS. 13A-13H illustrate various views of an intervertebral spacer 1300 having a height of about 9 mm and a length of about 26 mm; FIGS. 14A-14H illustrate various views of an intervertebral spacer 1400 having a height of about 10 mm and a length of about 26 mm; FIGS. 15A-15H illustrate various views of an intervertebral spacer 1500 having a height of about 11 mm and a length of about 26 mm; FIGS. 16A-16H illustrate various views of an intervertebral spacer 1600 having a height of about 12 mm and a length of about 26 mm; FIGS. 17A-17H illustrate various views of an intervertebral spacer 1700 having a height of about 13 mm and a length of about 26 mm; and FIGS. 18A-18H illustrate various views of an intervertebral spacer 1800 having a height of about 14 mm and a length of about 26 mm.

FIGS. 19A-21D illustrate various views of an inserter tool 1900 and its components, according to an embodiment of the present disclosure. Specifically, FIG. 19A is a perspective top view of a proximal end 1911 of the inserter tool 1900; FIG. 19B is a perspective top view of a distal end 1912 of the inserter tool 1900; FIG. 19C is a top view of the inserter tool 1900; FIG. 19D is a bottom view of the inserter tool 1900; FIG. 19E is a right side view of the inserter tool 1900; FIG. 19F is a left side view of the inserter tool 1900; FIG. 19G illustrates the distal end 1912 of the inserter tool 1900 with an extended inserter shaft tip 1943; FIG. 19H illustrates the distal end 1912 of the inserter tool 1900 with a retracted inserter shaft tip 1943; FIG. 20A is a perspective side view of the proximal end 1911 of a shroud 1910 of the inserter tool 1900; FIG. 20B is a perspective side view of the distal end 1912 of the shroud 1910; FIG. 20C is a close-up perspective view of the distal end 1912 of the shroud 1910 illustrating a cam lobe 1930; FIG. 20D is a close-up side view of the distal end 1912 of the shroud 1910 illustrating the cam lobe 1930; FIG. 21A is a perspective view of a proximal end 1941 of an inserter shaft 1940 of the inserter tool 1900; FIG. 21B is a perspective view of a distal end 1942 of the inserter shaft 1940; FIG. 21C is a close-up perspective view of the distal end 1942 of the inserter shaft 1940; and FIG. 21D is a close-up side view of the distal end 1942 of the inserter shaft 1940.

As shown in FIGS. 19A-21D, the inserter tool 1900 may generally comprise the shroud 1910, the inserter shaft 1940 (enclosed by the shroud 1910), a handle 1920 located toward the proximal end 1911 of the shroud 1910, and the cam lobe 1930 located at the distal end 1912 of the shroud 1910. The handle 1920 may be coupled to the shroud 1910 via a shroud stem 1916 (see FIGS. 20A and 20B) and the shroud 1910 may generally extend between the handle 1920 and the cam lobe 1930.

As shown in FIGS. 21A-21D, the inserter shaft 1940 may be coupled to a knob 1945 at its proximal end 1941 and have the inserter shaft tip 1943 at its distal end 1942. The knob 1945 may be accessible through a window 1914 formed in the shroud 1910 (see FIGS. 20A and 20B). The knob 1945 may be translated distally with respect to the shroud 1910 (as indicated by arrow 1901 shown in FIG. 19E) to extend the inserter shaft tip 1943 from the distal end 1912 of the shroud 1910 through the inserter shaft aperture 1918 (see FIG. 20C). The knob 1945 may also be translated proximally with respect to the shroud 1910 (as indicated by arrow 1902 shown in FIG. 19F) to retract the inserter shaft tip 1943 into the distal end 1912 of the shroud 1910.

As shown in FIGS. 21C-21D, the inserter shaft tip 1943 may have a conical shape that is configured to engage the chamfered surface 142 formed in the intervertebral spacer 100, as will be discussed in more detail below with respect to FIGS. 22A-26. The inserter shaft 1940 may also include threading 1944 formed along the inserter shaft 1940 proximate the inserter shaft tip 1943. In this manner, the inserter shaft 1940 may be removably couplable to the intervertebral spacer 100 by rotating the inserter shaft 1940 relative to the intervertebral spacer 100 to engage the threading 1944 of the inserter shaft 1940 (i.e., first threading) with the threading 144 formed in the intervertebral spacer 100 (i.e., second threading).

As shown in FIGS. 20C-20D, the cam lobe 1930 may comprise a complementarily shaped convex cam lobe surface 1931 having a second radius of curvature 1932 that is substantially equal to the first radius of curvature 121 shown in FIGS. 1C and 1D. However, it will be understood that in other embodiments, the cam lobe 1930 may alternatively comprise a concave surface that is complementarily shaped to a convex cam surface formed in a suitable intervertebral spacer (not shown).

In this application, surfaces that are "complementary" or "complementarily shaped" are surfaces that are shaped to follow similar pathways. In some embodiments, complementarily shaped surfaces may be concave and convex, respectively, Further, in some exemplary embodiment, complementarily shaped surfaces may have arcuate shapes. The radii of curvature of complementarily shaped surfaces may be similar, for example, with the surface having a concave curvature having a radius of curvature slightly larger than the radius of curvature of the convex surface. However, complementary surfaces, or complementarily shaped surfaces, need not, in all embodiments, be concave and convex (respectively), arcuate, or possessed of similar radii of curvature.

In at least one embodiment, the cam lobe 1930 may be located closer to the top of the shroud 1910 above a distal surface 1919. In this embodiment, the distal surface 1919 of the shroud 1910 may be concave. However, it will also be understood that in other embodiments (not shown), the cam lobe 1930 may be located closer to the bottom of the shroud 1910 below a distal surface of the shroud 1910, and the distal surface of the shroud 1910 may be at least partially concave, convex, and/or straight.

FIGS. 22A-26 illustrate various spinal fusion systems including an intervertebral spacer 100 and an inserter tool 1900 during various stages of operation. Specifically, FIG. 22A illustrates a spinal fusion system 2200 prior to assembly; FIG. 22B illustrates the spinal fusion system 2200 after assembly; FIG. 23 illustrates a spinal fusion system 2300 with the intervertebral spacer 100 partially rotated via a first force 1951; FIG. 24 illustrates a spinal fusion system 2400 with the intervertebral spacer 100 partially rotated via the first force 1951 and a second force 1952; FIG. 25 illustrates a spinal fusion system 2500 with the intervertebral spacer 100 fully rotated via the first force 1951; and FIG. 26 illustrates a spinal fusion system 2600 with the intervertebral spacer 100 fully rotated via the first force 1951 and the second force 1952.

FIGS. 22A and 22B illustrate how the intervertebral spacer 100 may be removably coupled to the inserter tool 1900. This may be accomplished by aligning the cam surface 120 with the cam lobe 1930, moving the cam surface 120 into engagement with the complimentarily shaped cam lobe 1930 (see arrow 1950 in FIG. 22A), and engaging the threading 1944 of the inserter shaft 1940 with the threading 144 of the intervertebral spacer 100 to removably couple the intervertebral spacer 100 to the inserter shaft 1940 (and thus the inserter tool 1900), as shown in FIG. 22B.

FIGS. 23 and 25 illustrate how the cam surface 120 of the intervertebral spacer 100 is rotatable against the complementary cam lobe surface 1931 of the cam lobe 1930 coupled to the inserter tool 1900, such that a first force 1951 causes the intervertebral spacer 100 to pivot, relative to the inserter tool 1900, about the pivot point 125 associated with the cam surface 120. In these embodiments, the cam lobe 1930 is configured to impart the first force 1951 to the cam surface 120 as the inserter tool 1900 is pushed distally, causing the intervertebral spacer 100 to pivot about the pivot point 125 associated with the cam surface 120. As previously discussed, frictional forces may act upon the superior and inferior surfaces 101, 102 of the intervertebral spacer 100 when it is inserted between two vertebral bodies. In this manner, the frictional forces imparted on the intervertebral spacer 100 by the vertebral bodies may act to oppose the first force 1951 and help facilitate rotation of the intervertebral spacer 100 as it is inserted between the vertebral bodies.

FIGS. 24 and 26 show how the chamfered surface 142 of the intervertebral spacer 100 is configured to receive a second force 1952 from the inserter shaft tip 1943 to further aid the first force 1951 in pivoting the intervertebral spacer 100 about the pivot point 125 associated with the cam surface 120. This may be accomplished by pushing the inserter shaft 1940 distally, causing the inserter shaft tip 1943 to engage the chamfered surface 142 of the intervertebral spacer 100 and pivot the intervertebral spacer 100 about the pivot point 125 associated with the cam surface 120. In a similar manner, the frictional forces imparted on the intervertebral spacer 100 by the vertebral bodies may act to oppose both of the first and second forces 1951, 1952 and help facilitate rotation of the intervertebral spacer 100 as it is inserted between the vertebral bodies.

FIGS. 27A-27C illustrate an example implantation process 2700 for an intervertebral spacer 100 relative to a vertebral body 2710, according to one embodiment of the present disclosure. Specifically, FIG. 27A illustrates the intervertebral spacer 100 inserted into the disc space above the vertebral body 2710 during a transforaminal insertion procedure; FIG. 27B illustrates rotation of the intervertebral spacer 100 relative to the vertebral body 2710 via one or more of the processes described above with respect to FIGS. 23-26; and FIG. 27C illustrates final placement of the intervertebral spacer 100 relative to the vertebral body 2710 with the inserter tool 1900 decoupled from the intervertebral spacer 100 and removed from the surgical site.

FIGS. 28A and 28B illustrate another example implantation process 2800 for one or more intervertebral spacers 100 relative to a vertebral body 2810, according to another embodiment of the present disclosure. Specifically, FIG. 28A illustrates one intervertebral spacer 100 inserted into the disc space above the vertebral body 2810 during a posterior insertion procedure, with the aid of a tool 3000 providing distraction during the insertion process, and FIG. 28B illustrates final placement of two intervertebral spacers 100 relative to the vertebral body 2810.

FIG. 29 illustrates a flowchart of a method 2900 for inserting an intervertebral spacer between two vertebral bodies of a patient, according to an embodiment of the present disclosure. In general, the method 2900 may include the use of an intervertebral spacer comprising a cam surface and an inserter tool that comprises a complimentarily shaped cam lobe configured to engage the cam surface and permit selective rotation of the intervertebral spacer relative to the inserter tool. The inserter tool may also comprise an inserter shaft with first threading and the intervertebral spacer may additionally comprises an aperture with second threading. The inserter shaft further comprise an inserter shaft tip and the intervertebral spacer may also comprise a chamfered surface proximate the aperture.

The method 2900 may begin with a step 2910 in which the cam surface of the intervertebral spacer may be aligned with the complimentarily shaped cam lobe of the inserter tool.

Once the cam surface of the intervertebral spacer has been aligned with the complimentarily shaped cam lobe of the inserter tool, the method 2900 may proceed to a step 2920 in which the cam surface may be moved into engagement with the complimentarily shaped cam lobe and the first threading of the inserter shaft may be engaged with the second threading of the intervertebral spacer to removably couple the intervertebral spacer to the inserter shaft.

Once the intervertebral spacer has been removably coupled to the inserter shaft, the method 2900 may proceed to a step 2930 in which the intervertebral spacer may be inserted between the two vertebral bodies of the patient.

Alternatively, or in addition thereto, once the intervertebral spacer has been inserted between the two vertebral bodies of the patient, the method 2900 may proceed to a step 2940 in which a first force may be applied to the cam surface with the complimentarily shaped cam lobe to cause the intervertebral spacer to pivot, relative to the inserter tool, about a pivot point associated with the cam surface.

Alternatively, or in addition thereto, the method 2900 may proceed to a step 2950 in which a second force may be applied to the chamfered surface with the inserter shaft tip to aid the first force in pivoting the intervertebral spacer about the pivot point associated with the cam surface.

Alternatively, or in addition thereto, the method 2900 may proceed to a step 2960 in which the first threading of the inserter shaft may be disengaged with the second threading of the intervertebral spacer, the inserter shaft may be removed from the patient, and the method 2900 may end.

Any methods disclosed herein comprise one or more steps or actions for performing the described method. One or more of the method steps and/or actions may be omitted from and of the methods disclosed herein. Moreover, any of the method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the systems, methods, and devices disclosed herein.

What is claimed is:

1. An intervertebral spacer comprising:
    a superior surface configured to engage a superior vertebral body;
    an inferior surface configured to engage an inferior vertebral body; and
    a peripheral wall extending from the superior surface to the inferior surface, the peripheral wall comprising:
        a distal end; and
        a proximal end comprising a cam surface that is rotatable against a complementary cam lobe surface of an inserter tool such that a first force causes the intervertebral spacer to pivot, relative to the inserter tool, about a pivot point associated with the cam surface;
    wherein:
        the intervertebral cage extends along an axis from the proximal end to the distal end; and
        the cam surface is concave and is shaped to permit withdrawal of the cam lobe surface parallel to the axis and nonparallel to the axis.

2. The intervertebral spacer of claim 1, wherein the cam surface comprises a concave surface having a first radius of curvature, the concave surface configured to receive a cam lobe comprising a complementarily shaped convex surface having a second radius of curvature that is substantially equal to the first radius of curvature.

3. The intervertebral spacer of claim 1 further comprising:
    an aperture formed in the proximal end of the intervertebral spacer; and
    a chamfered surface proximate the aperture,
    wherein the chamfered surface is configured to receive a second force from an inserter shaft tip to aid the first force in pivoting the intervertebral spacer about the pivot point associated with the cam surface.

4. The intervertebral spacer of claim 1, wherein the peripheral wall further comprises:
    a first side extending from the proximal end to the distal end; and
    a second side extending from the proximal end to the distal end,
    wherein the cam surface is located closer to the first side of the intervertebral spacer than the second side of the intervertebral spacer.

5. The intervertebral spacer of claim 4, wherein:
    the cam surface comprises a first radius of curvature that is substantially equal to a second radius of curvature of the cam lobe surface;
    the superior surface of the intervertebral spacer comprises a third radius of curvature extending from the proximal end of the intervertebral spacer to the distal end of the intervertebral spacer; and
    the inferior surface of the intervertebral spacer comprises a fourth radius of curvature extending from the proximal end of the intervertebral spacer to the distal end of the intervertebral spacer that is substantially equal to the third radius of curvature.

6. The intervertebral spacer of claim 4, wherein:
    the superior surface of the intervertebral spacer comprises a fifth radius of curvature extending from the first side of the intervertebral spacer to the second side of the intervertebral spacer; and
    the inferior surface of the intervertebral spacer comprises a sixth radius of curvature extending from the first side of the intervertebral spacer to the second side of the intervertebral spacer that is substantially equal to the fifth radius of curvature.

7. A spinal fusion system comprising:
    an intervertebral spacer comprising:
        a superior surface configured to engage a superior vertebral body;
        an inferior surface configured to engage an inferior vertebral body;
        a peripheral wall extending from the superior surface to the inferior surface, the peripheral wall comprising:
            a distal end; and
            a proximal end shaped to define:
                an aperture; and
                a cam surface that is rotatable against a complementary cam lobe surface such that a first force causes the intervertebral spacer to pivot about a pivot point associated with the cam surface; and
    an inserter tool comprising:
        a shroud having a proximal end and a distal end;
        a handle located toward the proximal end of the shroud; and
        a cam lobe located at the distal end of the shroud, the shroud extending between the handle and the cam lobe;
    wherein:
        the cam lobe is configured to impart the first force to the cam surface that causes the intervertebral spacer to pivot about the pivot point associated with the cam surface;
        the inserter tool further comprises an inserter shaft comprising a distal end having an inserter shaft tip;
        the inserter shaft further comprises first threading formed along the inserter shaft proximate the inserter shaft tip;
        the intervertebral spacer further comprises second threading formed within the aperture;
        the inserter shaft is configured to translate proximally and distally relative to the shroud, and
        the inserter shaft is removably couplable to the intervertebral spacer by rotating the inserter shaft relative to the intervertebral spacer to engage the first threading with the second threading to prevent rotation of the cam surface on the cam lobe.

8. The spinal fusion system of claim 7, wherein the intervertebral spacer further comprises a chamfered surface proximate the aperture, wherein the chamfered surface is configured to receive a second force from the inserter shaft tip to aid the first force in pivoting the intervertebral spacer about the pivot point associated with the cam surface.

9. The spinal fusion system of claim 7, wherein:
    the cam surface comprises a concave surface having a first radius of curvature; and
    the cam lobe comprises a complementarily shaped convex surface having a second radius of curvature that is substantially equal to the first radius of curvature.

10. The spinal fusion system of claim 9, wherein the peripheral wall further comprises:
a first side extending from the proximal end to the distal end; and
a second side extending from the proximal end to the distal end;
wherein the cam surface is located closer to the first side of the intervertebral spacer than the second side of the intervertebral spacer.

11. The spinal fusion system of claim 10, wherein:
the superior surface of the intervertebral spacer comprises a third radius of curvature extending from the proximal end of the intervertebral spacer to the distal end of the intervertebral spacer; and
the inferior surface of the intervertebral spacer comprises a fourth radius of curvature extending from the proximal end of the intervertebral spacer to the distal end of the intervertebral spacer that is substantially equal to the third radius of curvature.

12. The spinal fusion system of claim 10, wherein:
the superior surface of the intervertebral spacer comprises a fifth radius of curvature extending from the first side of the intervertebral spacer to the second side of the intervertebral spacer; and
the inferior surface of the intervertebral spacer comprises a sixth radius of curvature extending from the first side of the intervertebral spacer to the second side of the intervertebral spacer that is substantially equal to the fifth radius of curvature.

13. The intervertebral spacer of claim 1, wherein the intervertebral cage extends along a straight axis from the proximal end to the distal end.

14. The intervertebral spacer of claim 1, wherein the cam surface comprises an arcuate shape extending along an arc of 90° or less.

15. The spinal fusion system of claim 7, wherein the cam surface is displaced from the aperture.

16. The spinal fusion system of claim 7, wherein the intervertebral spacer is formed as a single piece.

17. The spinal fusion system of claim 9, wherein:
the intervertebral cage extends along an axis from the proximal end to the distal end; and
the cam surface is shaped to permit withdrawal of the cam lobe surface along a direction parallel to the axis.

18. The spinal fusion system of claim 17, wherein the cam surface comprises an arcuate shape extending along an arc of 90° or less.

19. An intervertebral spacer comprising:
a superior surface configured to engage a superior vertebral body;
an inferior surface configured to engage an inferior vertebral body; and
a peripheral wall extending from the superior surface to the inferior surface, the peripheral wall comprising:
a distal end; and
a proximal end comprising a cam surface that is rotatable against a complementary cam lobe surface of an inserter tool such that a first force causes the intervertebral spacer to pivot, relative to the inserter tool, about a pivot point associated with the cam surface;
wherein the cam surface is concave and comprises an arcuate shape extending along an arc of 90° or less.

20. The intervertebral spacer of claim 19, wherein:
the cam surface comprises a concave surface having a first radius of curvature, the concave surface configured to receive a cam lobe comprising a complementarily shaped convex surface having a second radius of curvature that is substantially equal to the first radius of curvature;
the peripheral wall further comprises:
a first side extending from the proximal end to the distal end; and
a second side extending from the proximal end to the distal end;
wherein the cam surface is located closer to the first side of the intervertebral spacer than the second side of the intervertebral spacer;
the superior surface of the intervertebral spacer comprises a third radius of curvature extending from the proximal end of the intervertebral spacer to the distal end of the intervertebral spacer;
the inferior surface of the intervertebral spacer comprises a fourth radius of curvature extending from the proximal end of the intervertebral spacer to the distal end of the intervertebral spacer that is substantially equal to the third radius of curvature;
the superior surface of the intervertebral spacer comprises a fifth radius of curvature extending from the first side of the intervertebral spacer to the second side of the intervertebral spacer; and
the inferior surface of the intervertebral spacer comprises a sixth radius of curvature extending from the first side of the intervertebral spacer to the second side of the intervertebral spacer that is substantially equal to the fifth radius of curvature.

21. An intervertebral spacer comprising:
a superior surface configured to engage a superior vertebral body;
an inferior surface configured to engage an inferior vertebral body; and
a peripheral wall extending from the superior surface to the inferior surface, the peripheral wall comprising:
a distal end; and
a proximal end comprising a cam surface that is rotatable against a complementary cam lobe surface of an inserter tool such that a first force causes the intervertebral spacer to pivot, relative to the inserter tool, about a pivot point associated with the cam surface;
wherein:
the intervertebral cage extends along an axis from the proximal end to the distal end;
the cam surface is concave and is shaped to permit withdrawal of the cam lobe surface along a direction parallel to the axis; and
the cam surface is configured to function independently of any other feature on the intervertebral spacer such that the first force, alone, urges the intervertebral spacer to pivot relative to the inserter tool.

22. The intervertebral spacer of claim 21, wherein the cam surface comprises a concave surface having a first radius of curvature, the concave surface configured to receive a cam lobe comprising a complementarily shaped convex surface having a second radius of curvature that is substantially equal to the first radius of curvature.

23. The intervertebral spacer of claim 21, further comprising:
an aperture formed in the proximal end of the intervertebral spacer; and
a chamfered surface proximate the aperture,
wherein the chamfered surface is configured to receive a second force from an inserter shaft tip to aid the first force in pivoting the intervertebral spacer about the pivot point associated with the cam surface.

24. The intervertebral spacer of claim 21, wherein the peripheral wall further comprises:
- a first side extending from the proximal end to the distal end; and
- a second side extending from the proximal end to the distal end,
- wherein the cam surface is located closer to the first side of the intervertebral spacer than the second side of the intervertebral spacer.

* * * * *